US009779167B2

(12) United States Patent
Kusumoto et al.

(10) Patent No.: US 9,779,167 B2
(45) Date of Patent: Oct. 3, 2017

(54) MANAGEMENT SYSTEM FOR SKIN CONDITION MEASUREMENT ANALYSIS INFORMATION AND MANAGEMENT METHOD FOR SKIN CONDITION MEASUREMENT ANALYSIS INFORMATION

(71) Applicant: HITACHI MAXELL, LTD., Ibaraki-shi, Osaka (JP)

(72) Inventors: Fumie Kusumoto, Ibaraki (JP); Masashi Yoshimura, Ibaraki (JP); Eiji Sakata, Ibaraki (JP); Hironobu Nagano, Ibaraki (JP); Kenji Matsuoka, Ibaraki (JP); Kengo Miura, Ibaraki (JP)

(73) Assignee: HITACHI MAXELL, LTD., Osaka (JP)

( * ) Notice: Subject to any disclaimer, the term of this patent is extended or adjusted under 35 U.S.C. 154(b) by 289 days.

(21) Appl. No.: 14/379,086

(22) PCT Filed: Feb. 15, 2013

(86) PCT No.: PCT/JP2013/053763
§ 371 (c)(1),
(2) Date: Aug. 15, 2014

(87) PCT Pub. No.: WO2013/122233
PCT Pub. Date: Aug. 22, 2013

(65) Prior Publication Data
US 2015/0186518 A1 Jul. 2, 2015

(30) Foreign Application Priority Data

Feb. 15, 2012 (JP) .................. 2012-030020
Dec. 4, 2012 (JP) .................. 2012-265857

(51) Int. Cl.
*G06F 17/30* (2006.01)
*A61B 5/00* (2006.01)
(Continued)

(52) U.S. Cl.
CPC ...... *G06F 17/30864* (2013.01); *A61B 5/0022* (2013.01); *A61B 5/14532* (2013.01);
(Continued)

(58) Field of Classification Search
CPC ..... A61B 5/441; A61B 5/14532; A61B 5/442; A61B 5/443; H04L 67/10; H04L 67/42
See application file for complete search history.

(56) References Cited

U.S. PATENT DOCUMENTS 7,324,668 B2 * 1/2008 Rubinstenn .......... A45D 44/005
382/118
9,202,069 B2 * 12/2015 Nyman ................. G06F 21/604
(Continued)

FOREIGN PATENT DOCUMENTS

EP     1 297 782 A1   4/2003
JP    A-2001-338187   12/2001
(Continued)

OTHER PUBLICATIONS

International Search Report issued in International Patent Application No. PCT/JP2013/053763 dated Jun. 4, 2013.
(Continued)

*Primary Examiner* — Chirag R Patel
(74) *Attorney, Agent, or Firm* — Oliff PLC

(57) ABSTRACT

Service can be offered free of charge and the cost of a skin condition measuring device can be reduced by effectively using data on the occasion of obtaining an analysis result by transmitting measurement data by the skin condition measuring device to a server of a company providing a service of analyzing the measurement data. When a request is made from a contractor client to acquire data registered in a measurement data database, authentication is executed based on a contractor ID input from the contractor client. Additionally, when the measurement data database is searched from a contractor database based on the contractor ID, a search level and an access level are obtained. The contractor client is permitted to search the measurement data database within a range of the search level and the access level.

45 Claims, 38 Drawing Sheets

(51) Int. Cl.
*A61B 5/145* (2006.01)
*G06Q 30/06* (2012.01)
*G01N 21/17* (2006.01)
*H04L 29/08* (2006.01)
*H04L 29/06* (2006.01)
*G06F 19/00* (2011.01)

(52) U.S. Cl.
CPC ............ *A61B 5/441* (2013.01); *A61B 5/442* (2013.01); *A61B 5/4836* (2013.01); *G01N 21/17* (2013.01); *G06F 17/30557* (2013.01); *G06F 19/3418* (2013.01); *G06Q 30/0631* (2013.01); *H04L 67/10* (2013.01); *H04L 67/42* (2013.01); *G01N 2021/1765* (2013.01)

(56) References Cited

U.S. PATENT DOCUMENTS

| | | |
|---|---|---|
| 2006/0031094 A1 | 2/2006 | Cohen et al. |
| 2007/0064989 A1* | 3/2007 | Chhibber ............... A61B 5/442 382/128 |
| 2008/0162189 A1 | 7/2008 | Hamano et al. |
| 2010/0185064 A1 | 7/2010 | Bandic et al. |
| 2011/0301441 A1* | 12/2011 | Bandic ................ A61B 5/0059 600/306 |

FOREIGN PATENT DOCUMENTS

| | | |
|---|---|---|
| JP | A-2002-15068 | 1/2002 |
| JP | A-2002-132794 | 5/2002 |
| JP | A-2002-366651 | 12/2002 |
| JP | A-2003-91583 | 3/2003 |
| JP | A-2004-354207 | 12/2004 |
| JP | A-2005-56165 | 3/2005 |
| JP | A-2005-148797 | 6/2005 |
| JP | A-2006-202069 | 8/2006 |
| JP | A-2011-232892 | 11/2011 |
| KR | 20030070868 A | 9/2003 |

OTHER PUBLICATIONS

Written Opinion issued in International Patent Application No. PCT/JP2013/053763 dated Jun. 4, 2013.
Sep. 23, 2015 Extended Search Report issued in European Patent Application No. 13748845.8.
Jul. 28, 2015 Office Action issued in Japanese Patent Application No. 2013-558762.

* cited by examiner

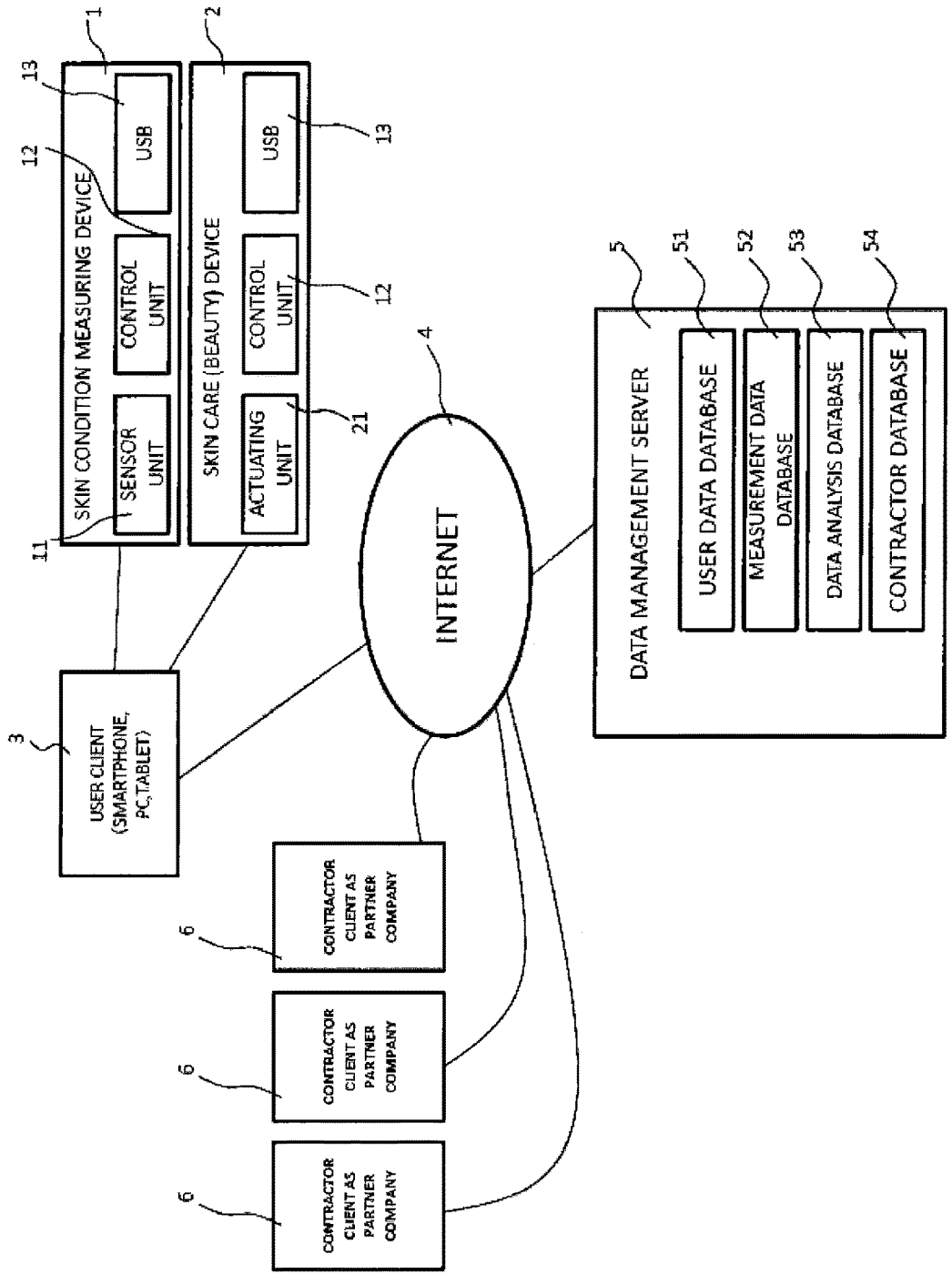
[Fig. 1]

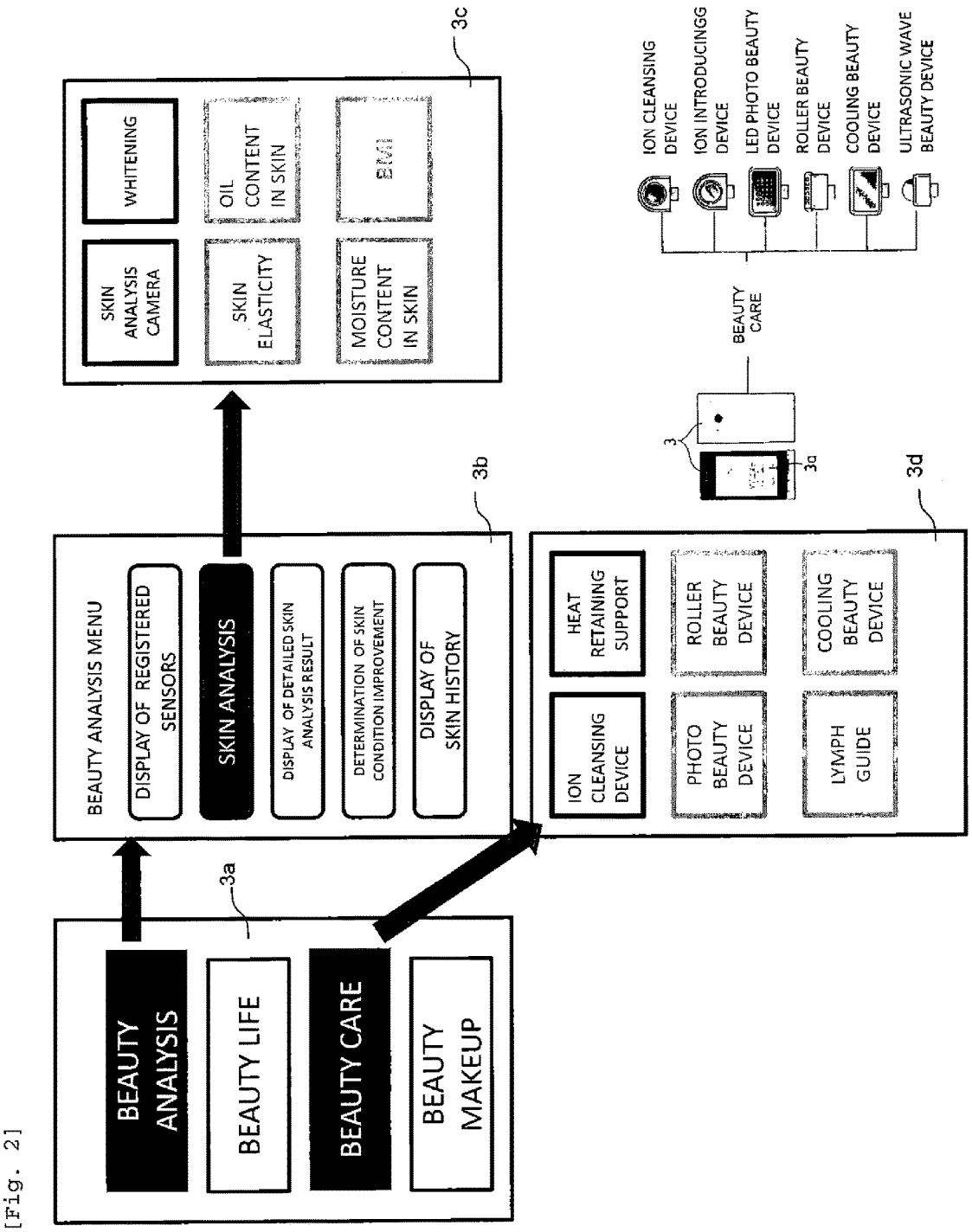
[Fig. 2]

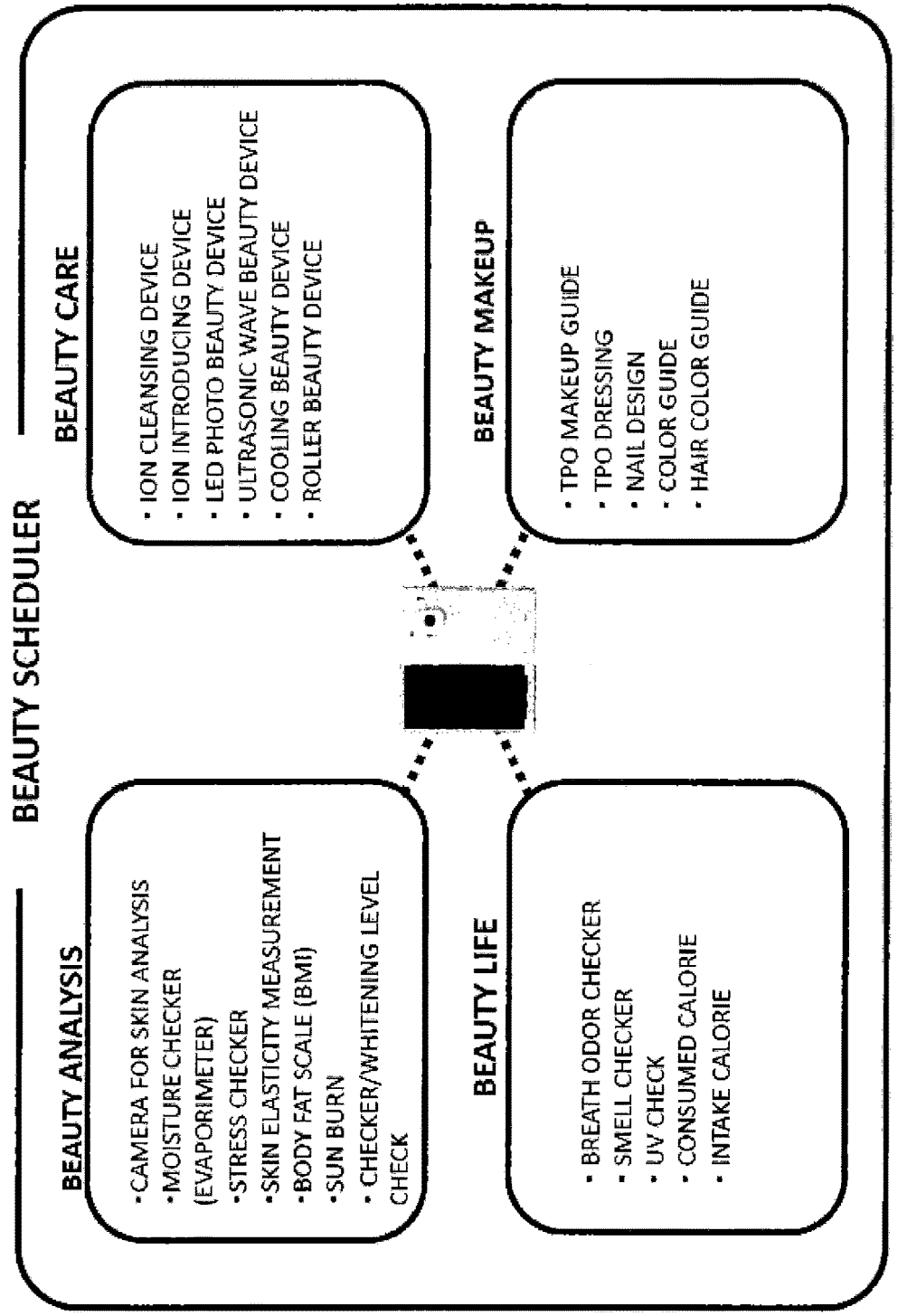
[Fig. 3]

[Fig. 4]
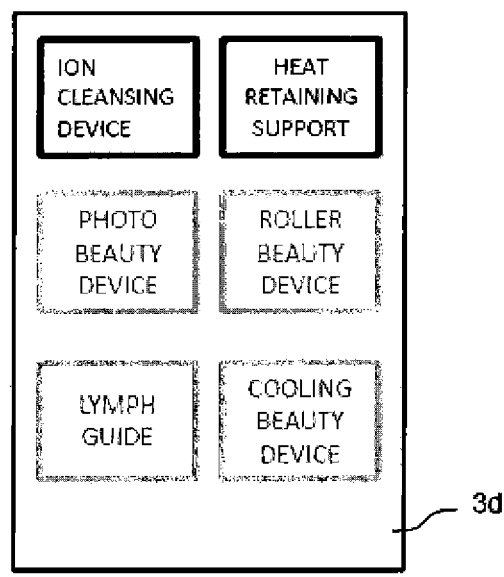

[Fig. 5]
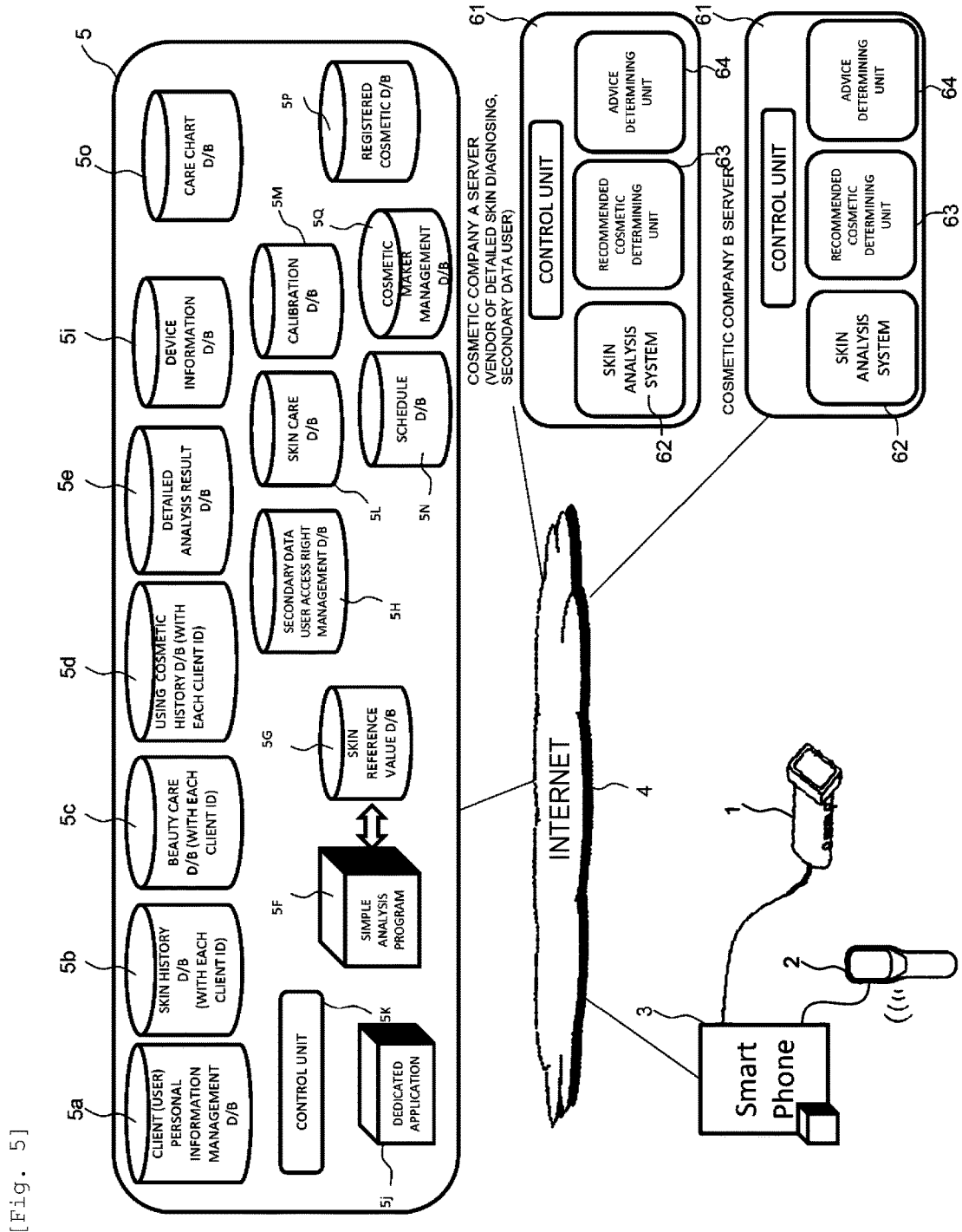

[Fig. 6]
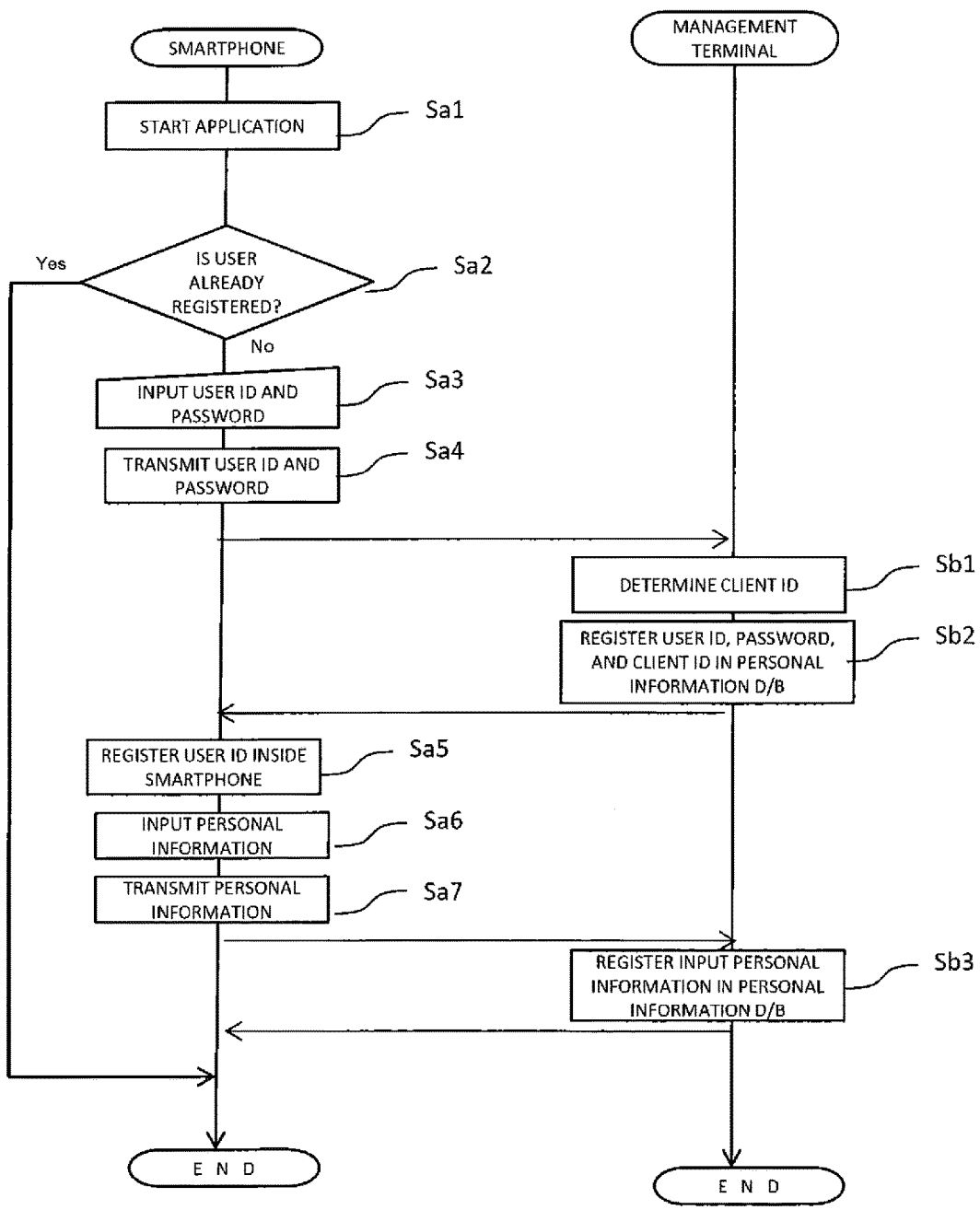

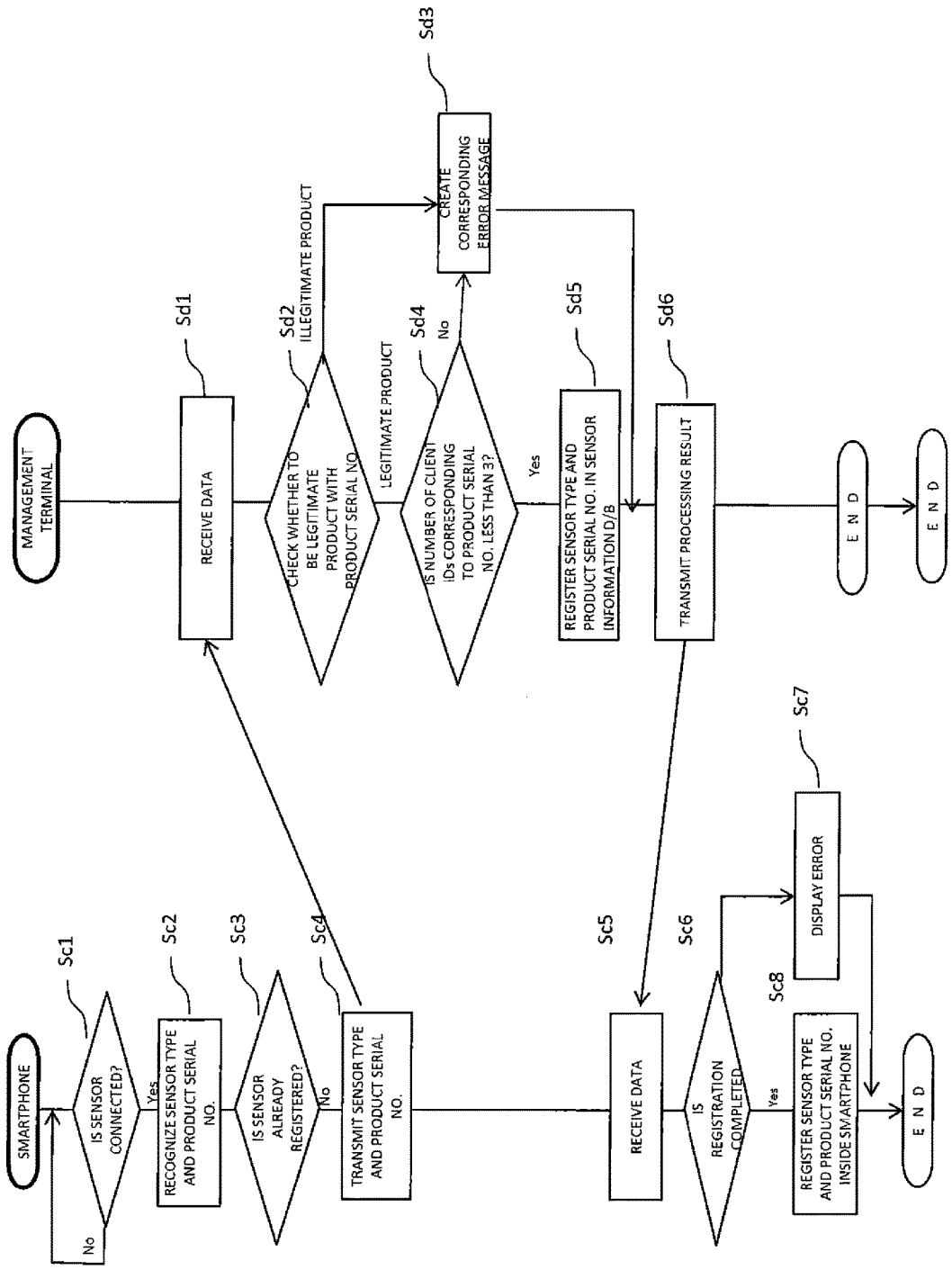
[Fig. 7]

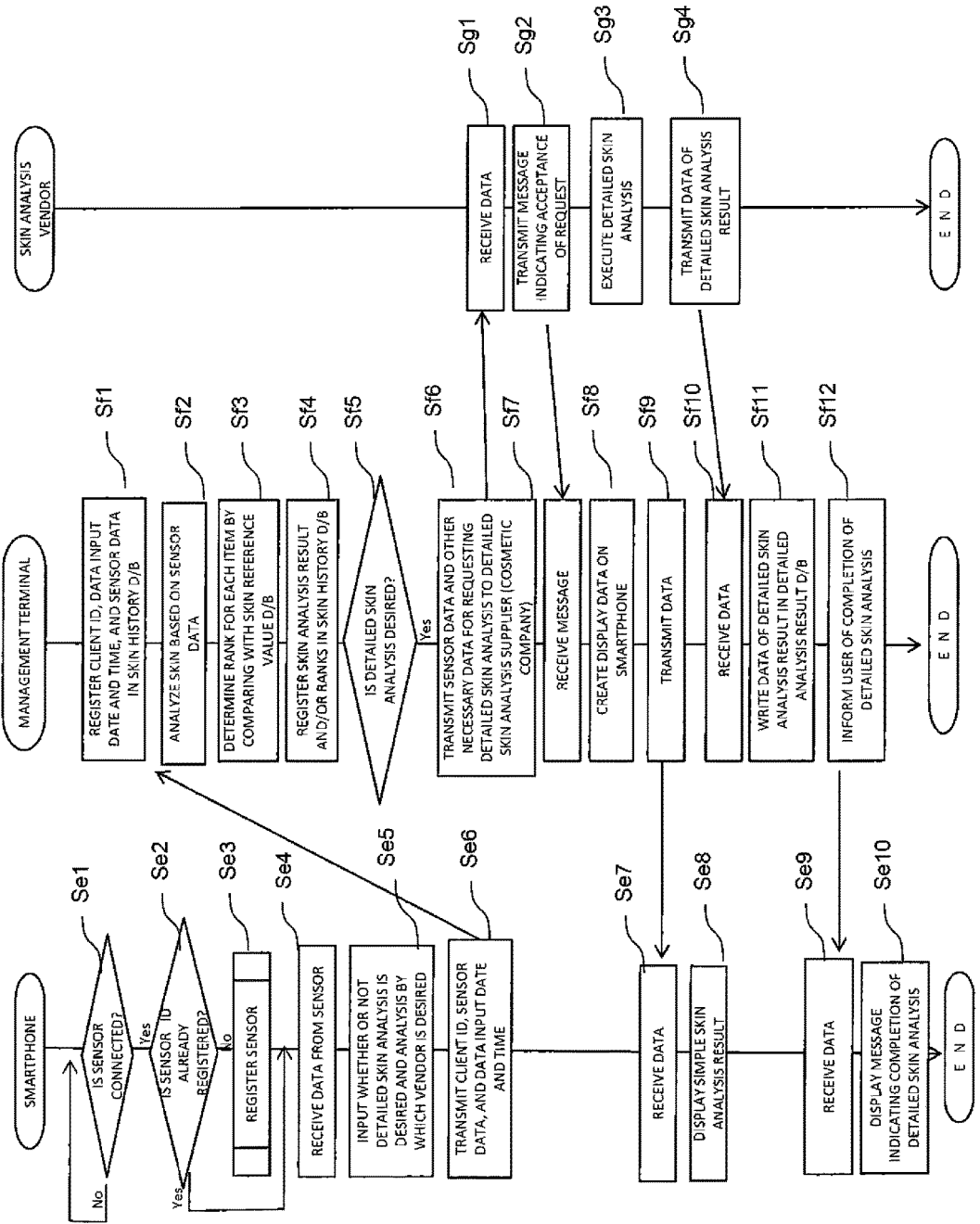
[Fig. 8]

[Fig. 9]
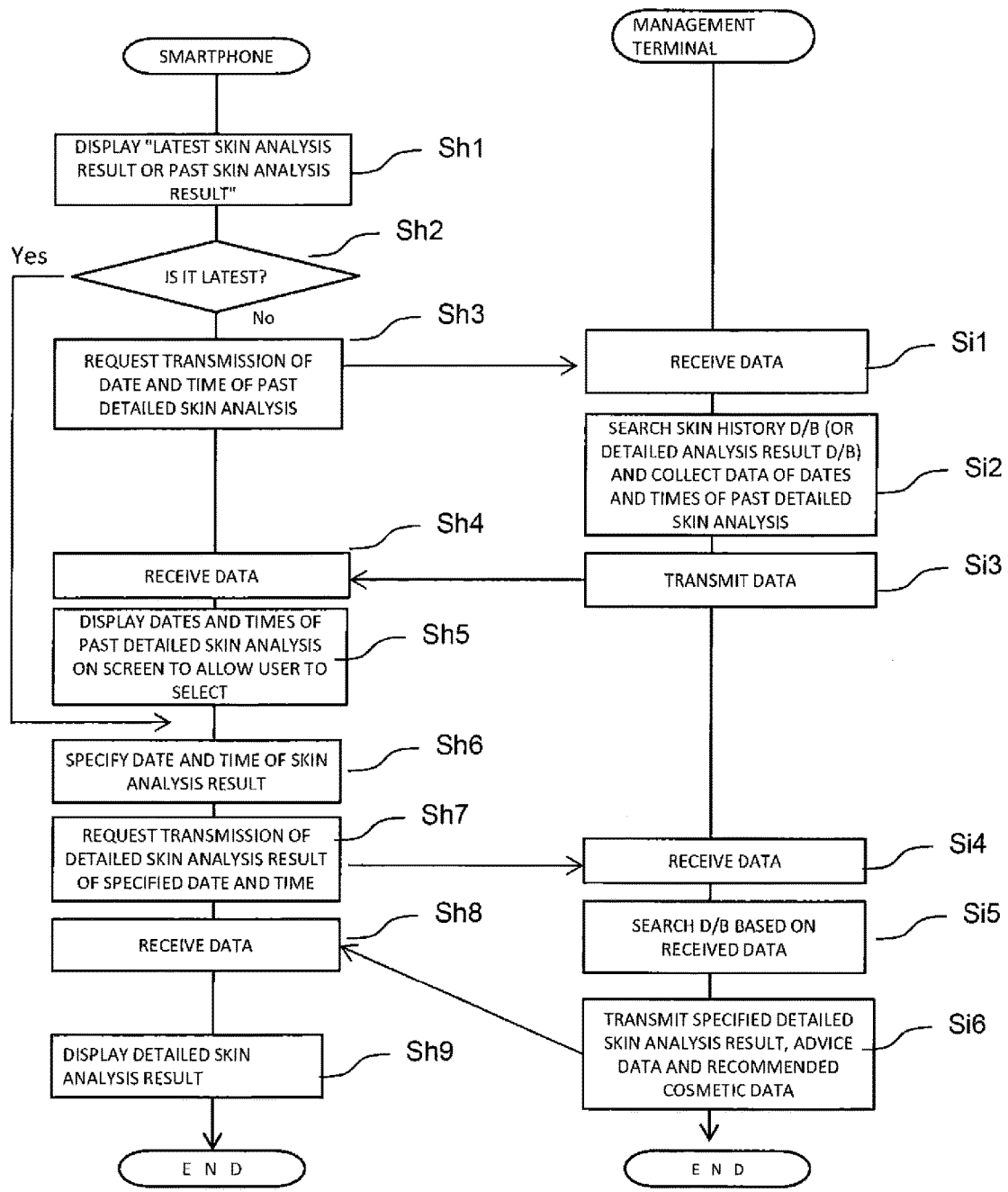

[Fig. 10]
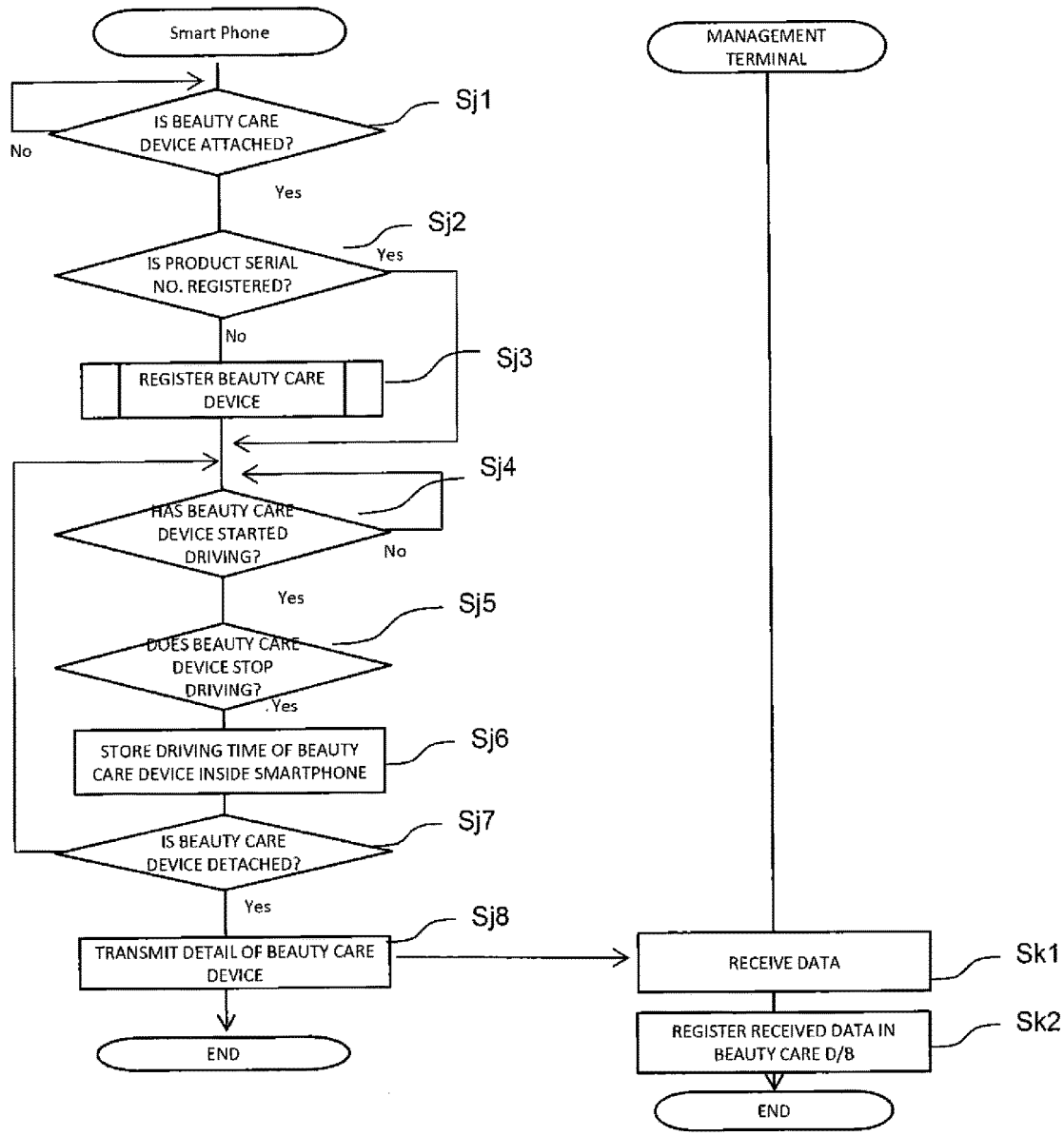

[Fig. 11]
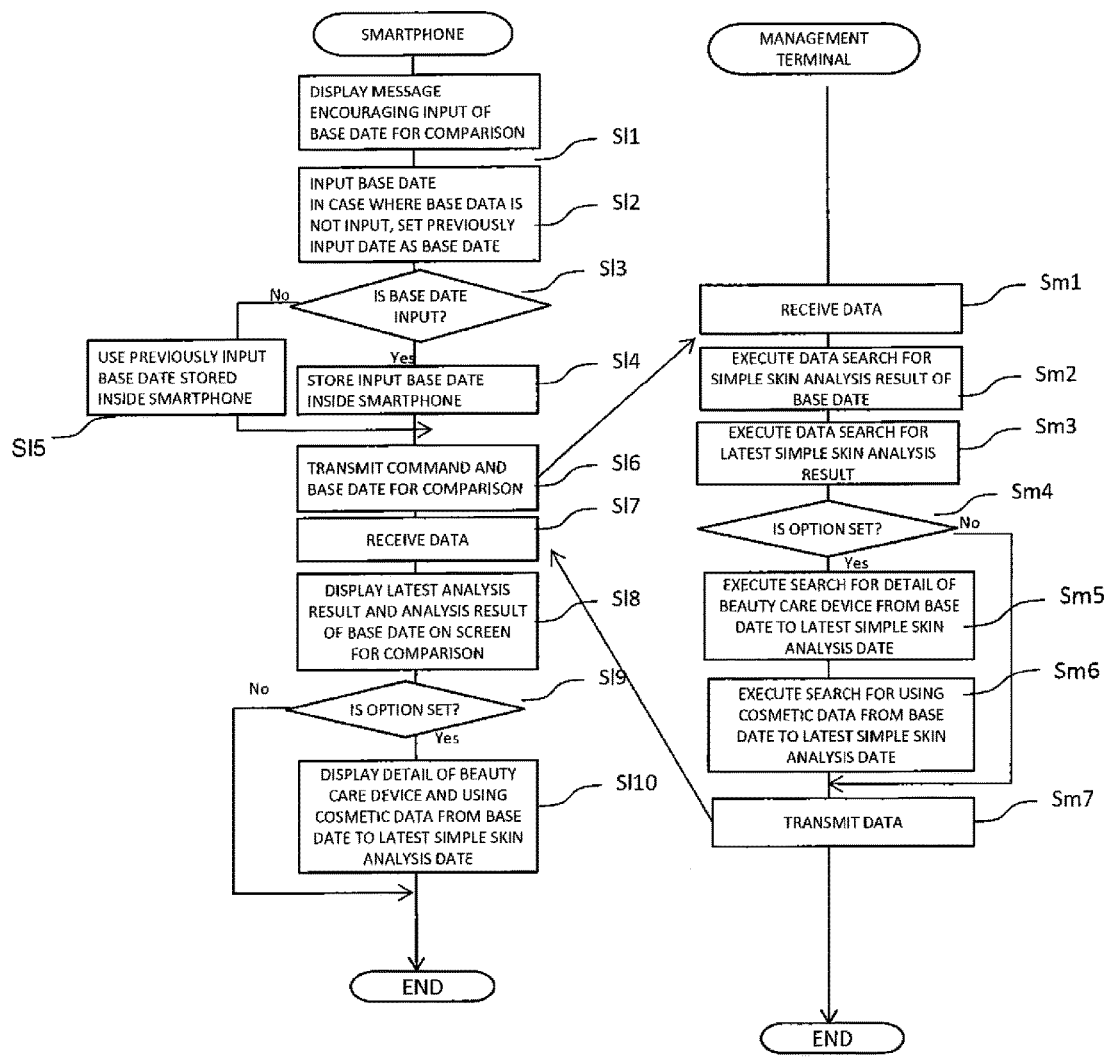

[Fig. 12]
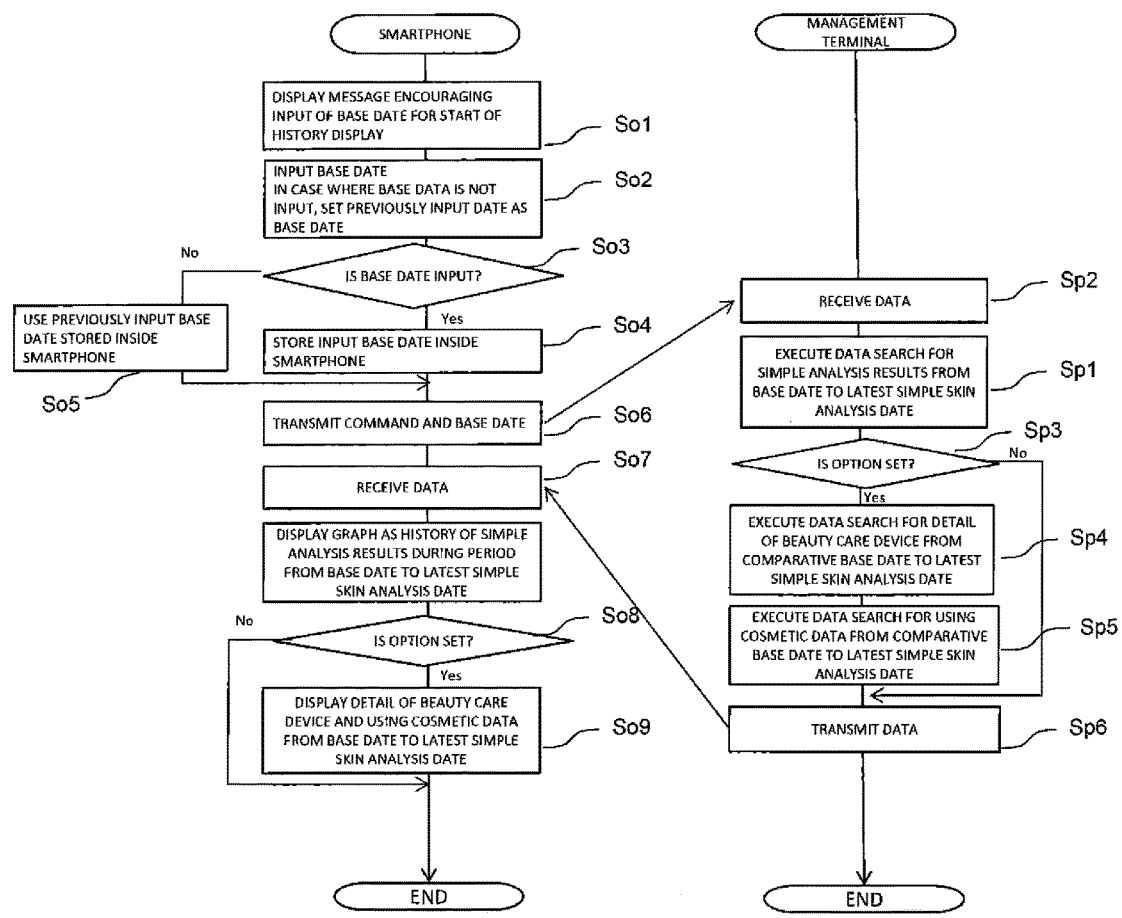

[Fig. 13]
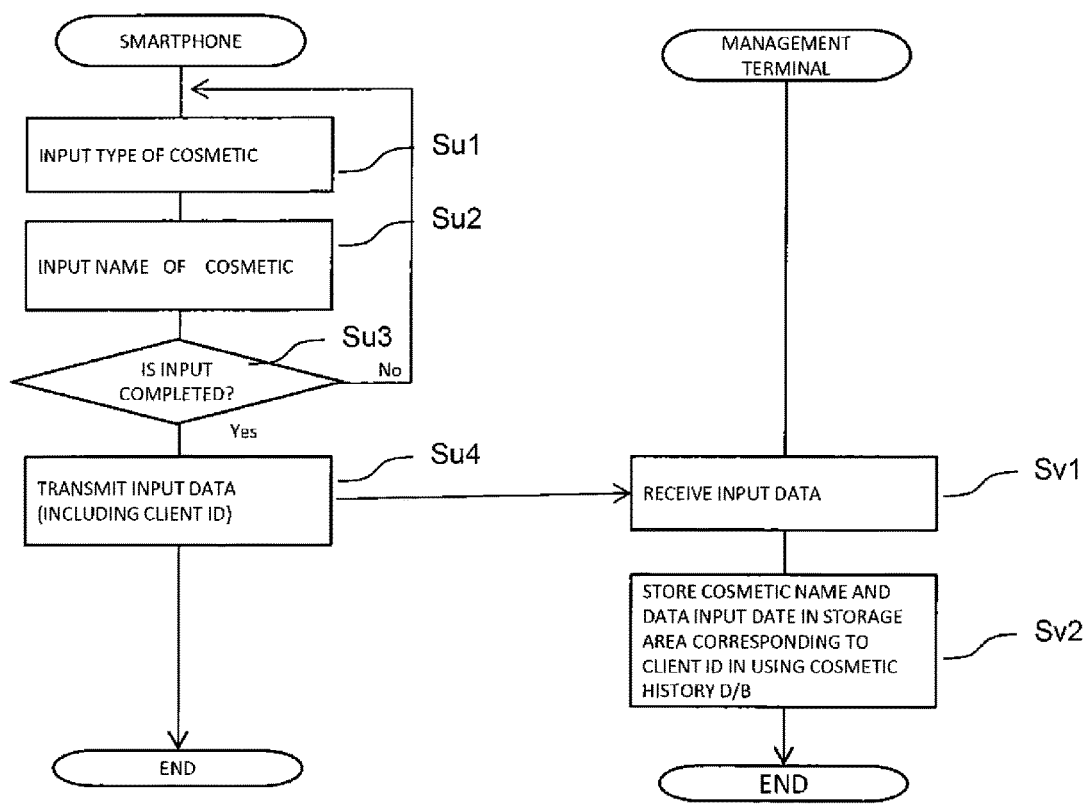

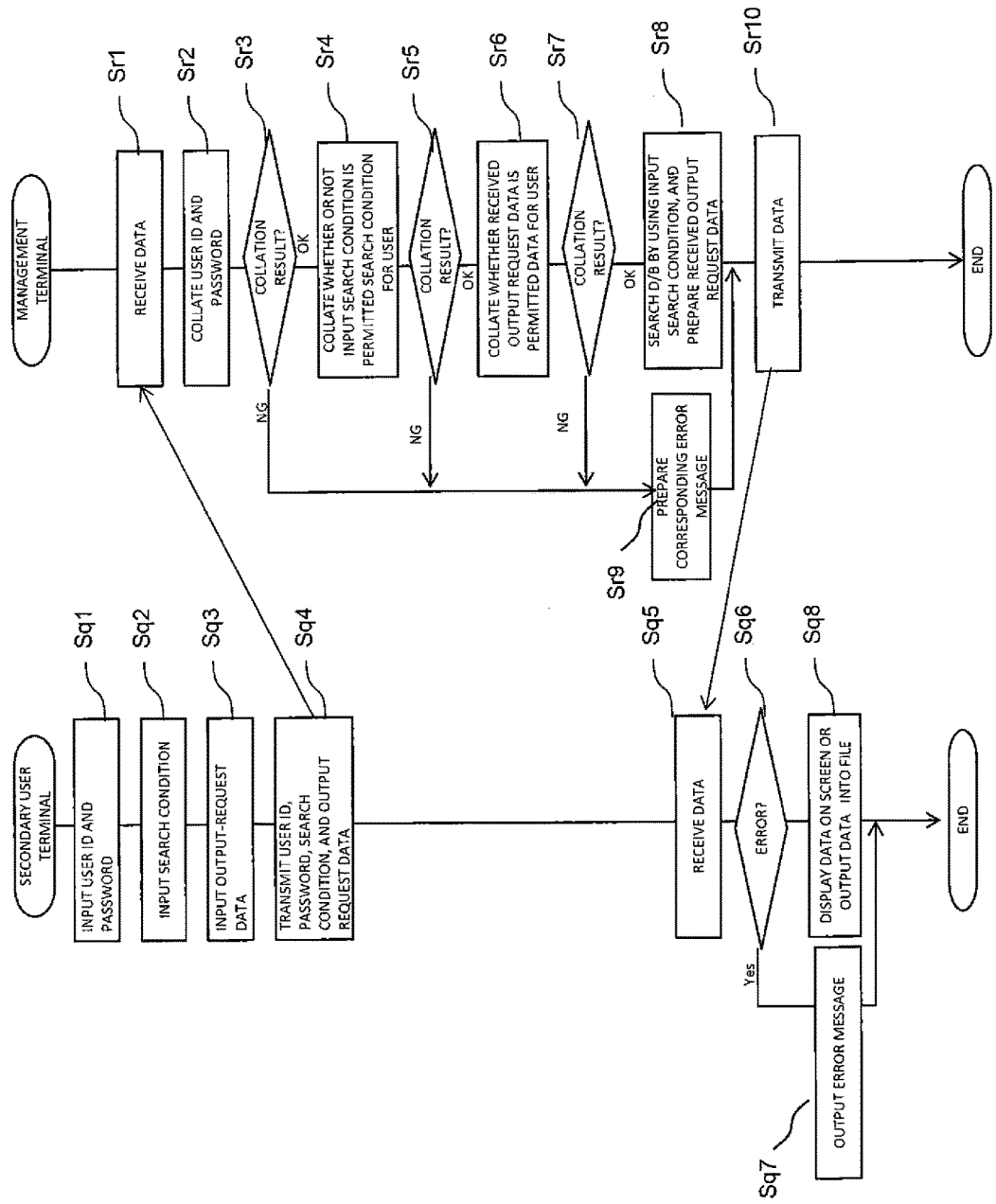
[Fig. 14]

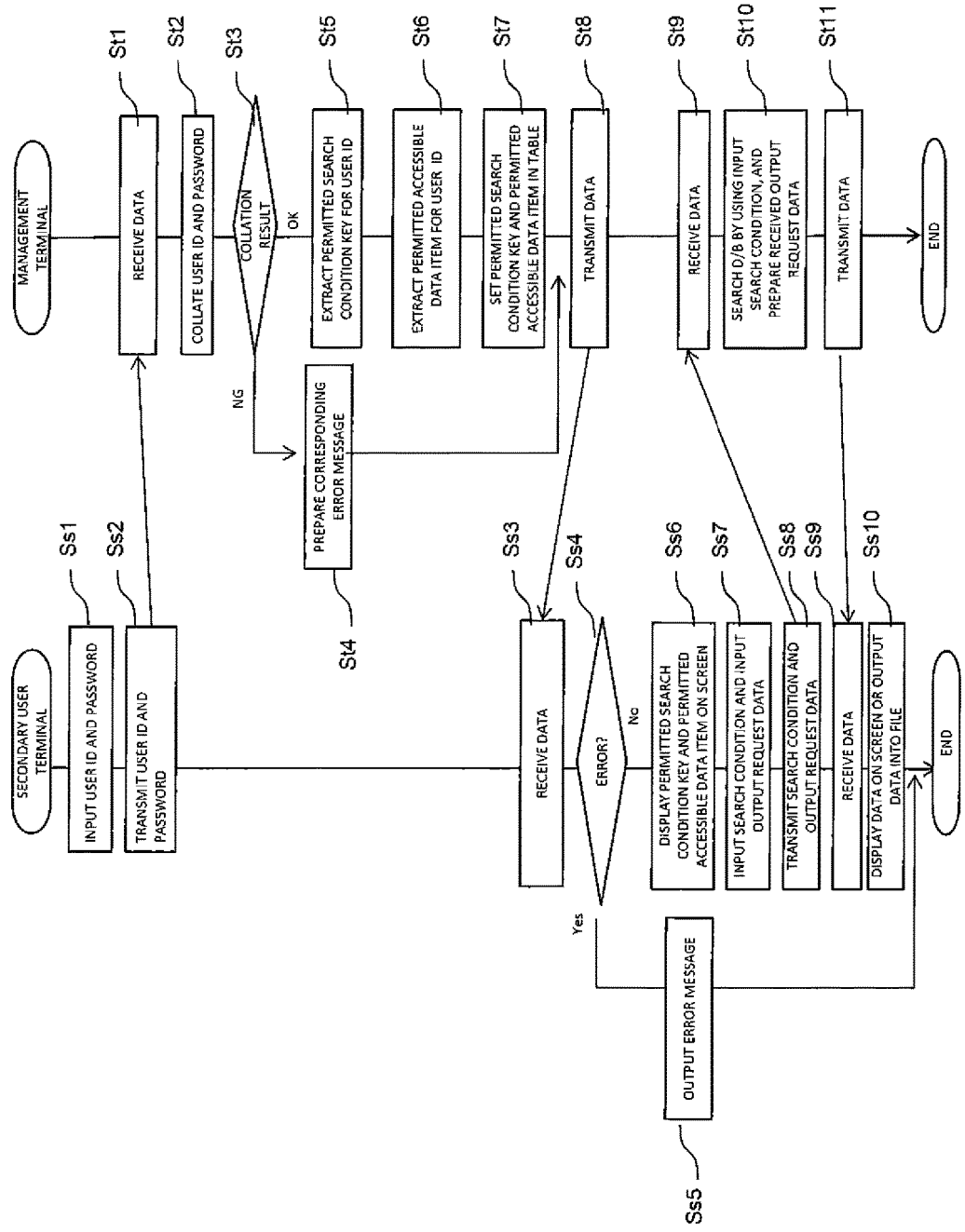
[Fig. 15]

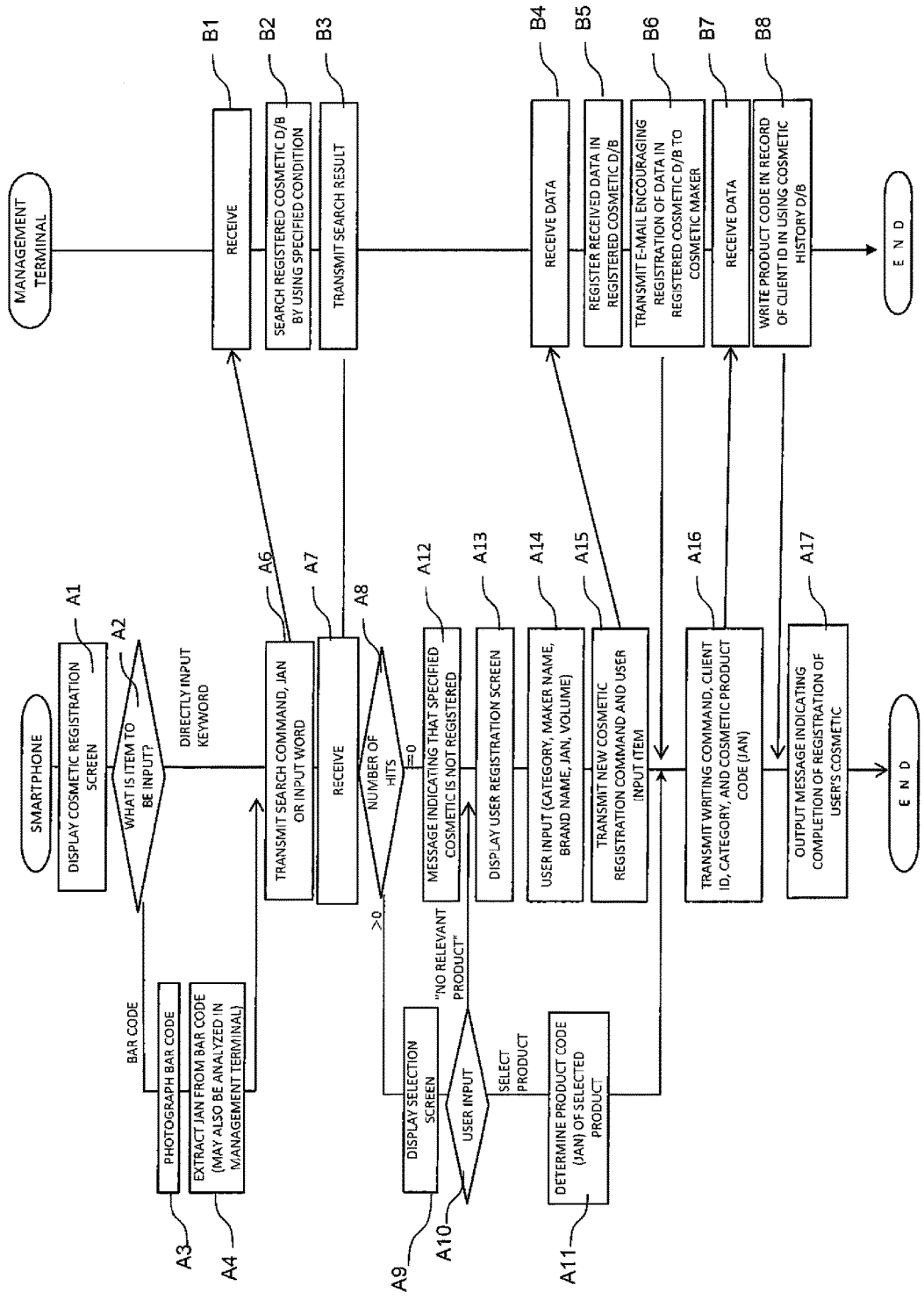
[Fig. 16]

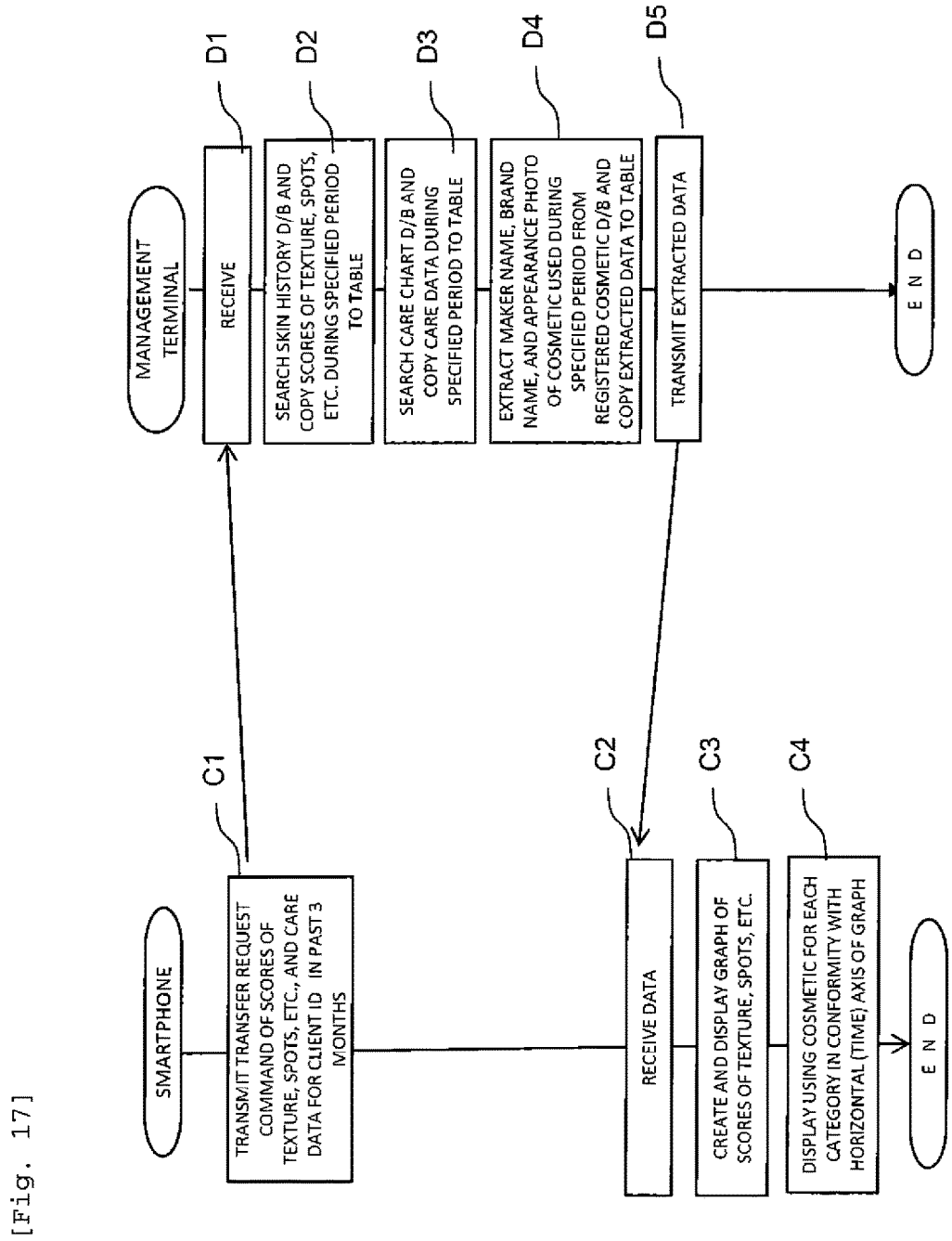
[Fig. 17]

[Fig. 18]
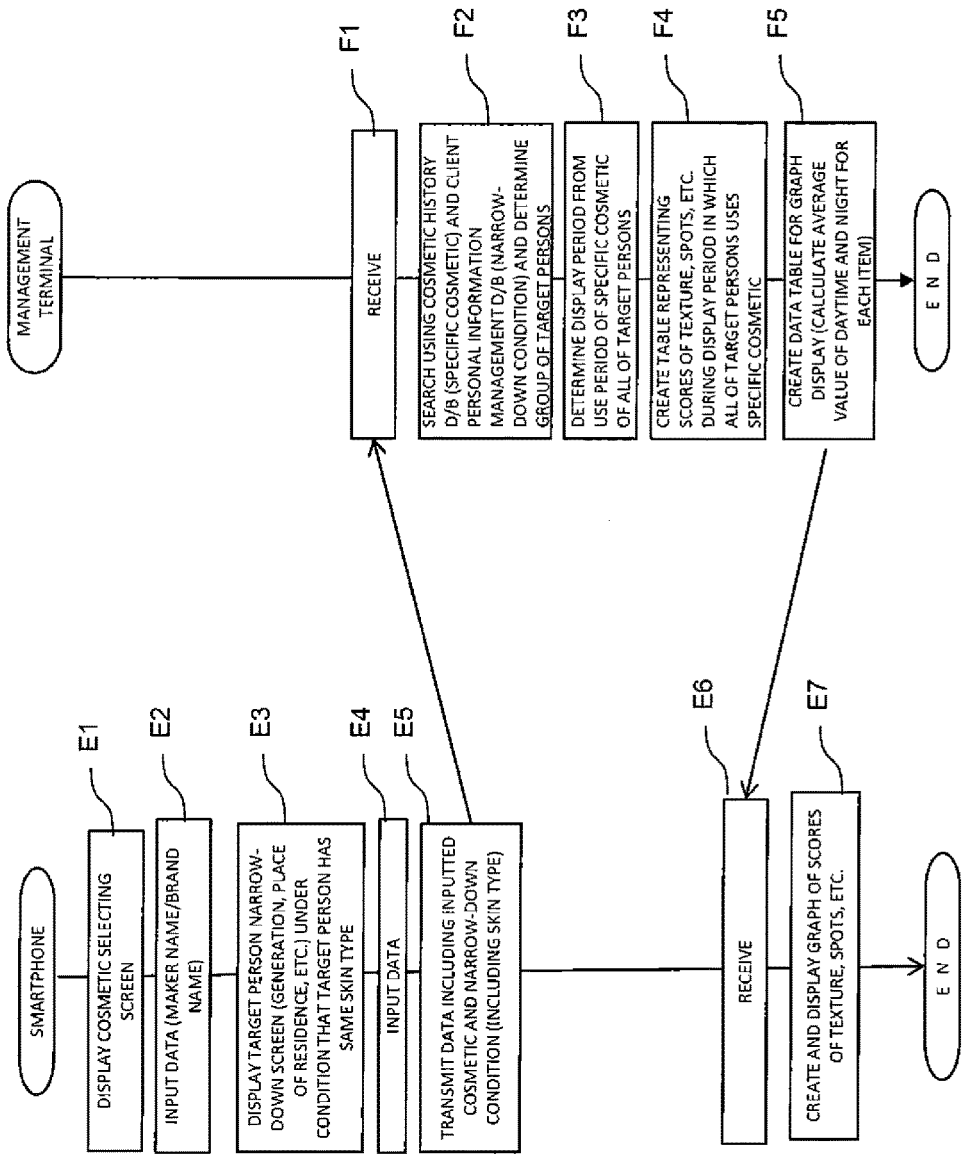

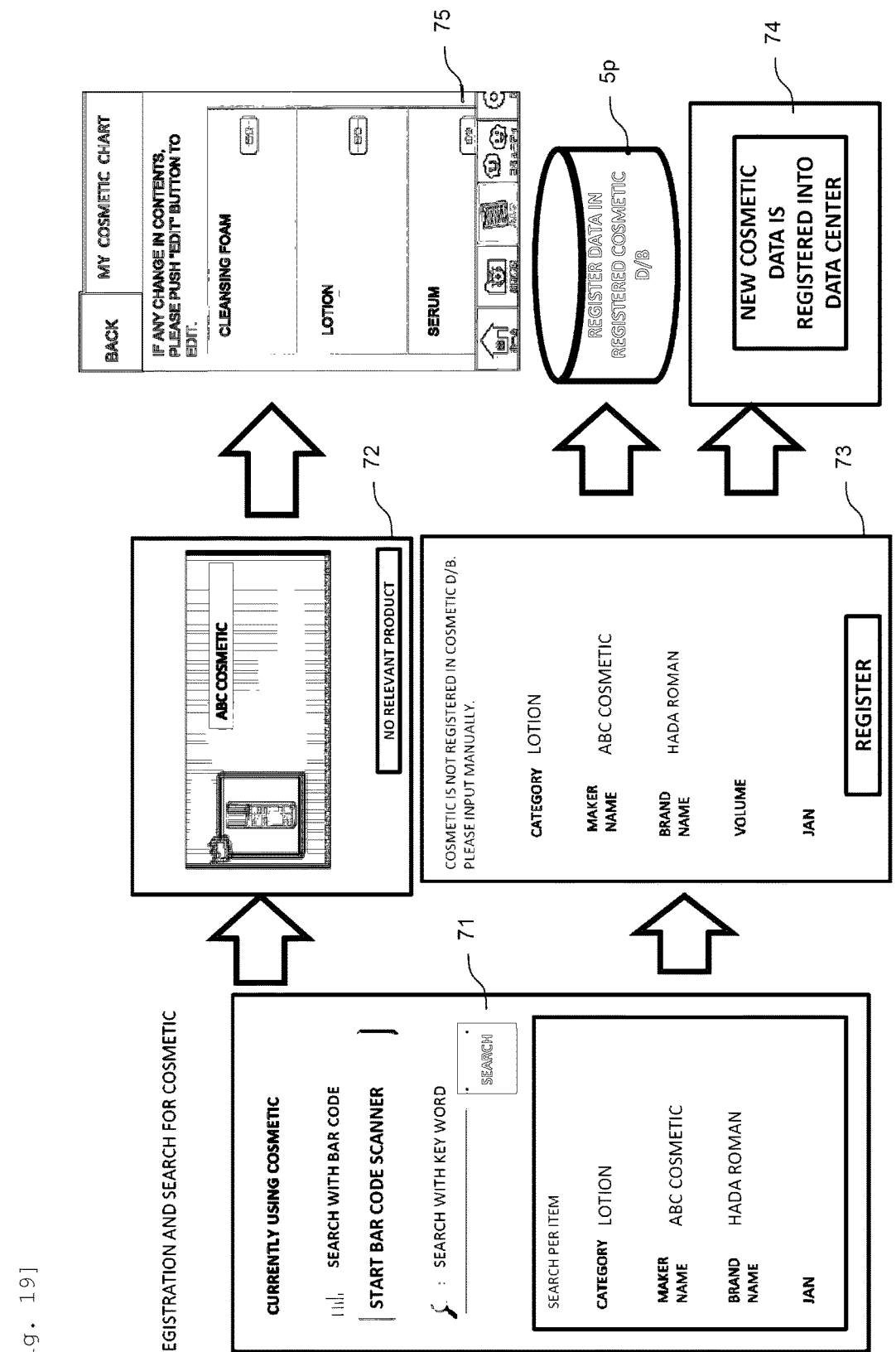

[Fig. 20]

INPUT TODAY'S CARE

| FACIAL WASH | MAKEUP REMOVER |
|---|---|
| MAKER NAME: XXX<br>PRODUCT NAME: abc ✓<br>VOLUME: 100 ml | MAKER NAME: PPPP<br>PRODUCT NAME: vvv ✓<br>VOLUME: 200 ml |

| LOTION | MILKY LOTION |
|---|---|
| MAKER NAME: SS<br>PRODUCT NAME: SSP ✓<br>VOLUME: 120 ml | MAKER NAME: SS<br>PRODUCT NAME: SSVP ☐<br>VOLUME: 100 ml |

| CREAM | SERUM |
|---|---|
| MAKER NAME: PPP<br>PRODUCT NAME: PAPA ☐<br>VOLUME: 100 ml | MAKER NAME: KE<br>PRODUCT NAME: KECC ✓<br>VOLUME: 100 ml |

WHITENING LOTION
MAKER NAME: PPP
PRODUCT NAME: PA ☐
VOLUME: 100 ml

REGISTER?
OK

76

SCHEDULER

2012  9
| Sun | Mon | Tue | Wed | Thu | Fri | Sat |
|---|---|---|---|---|---|---|
| 26 | 27 | 28 | 29 | 30 | 31 | 1 |
| 2 | 3 | 4 | 5 | 6 | 7 | 8 |
| 9 | 10 | 11 | 12 | 13 | 14 | 15 |
| 16 | 17 | 18 | 19 | 20 | 21 | 22 |
| 23 | 24 | 25 | 26 | 27 | 28 | 29 |
| 30 | | | | | | 6 |

77

CARE CONDITIONS DISPLAY SCREEN

| CARE | MORNING | NIGHT |
|---|---|---|
| FACIAL WASH | abc | Abc |
| MAKEUP REMOVER | - | vvvv |
| LOTION | SSSP | SSSP |
| MILKY LOTION | SSVP | - |
| CREAM | - | PAPAPA |
| SERUM | KECC | KECC |

78

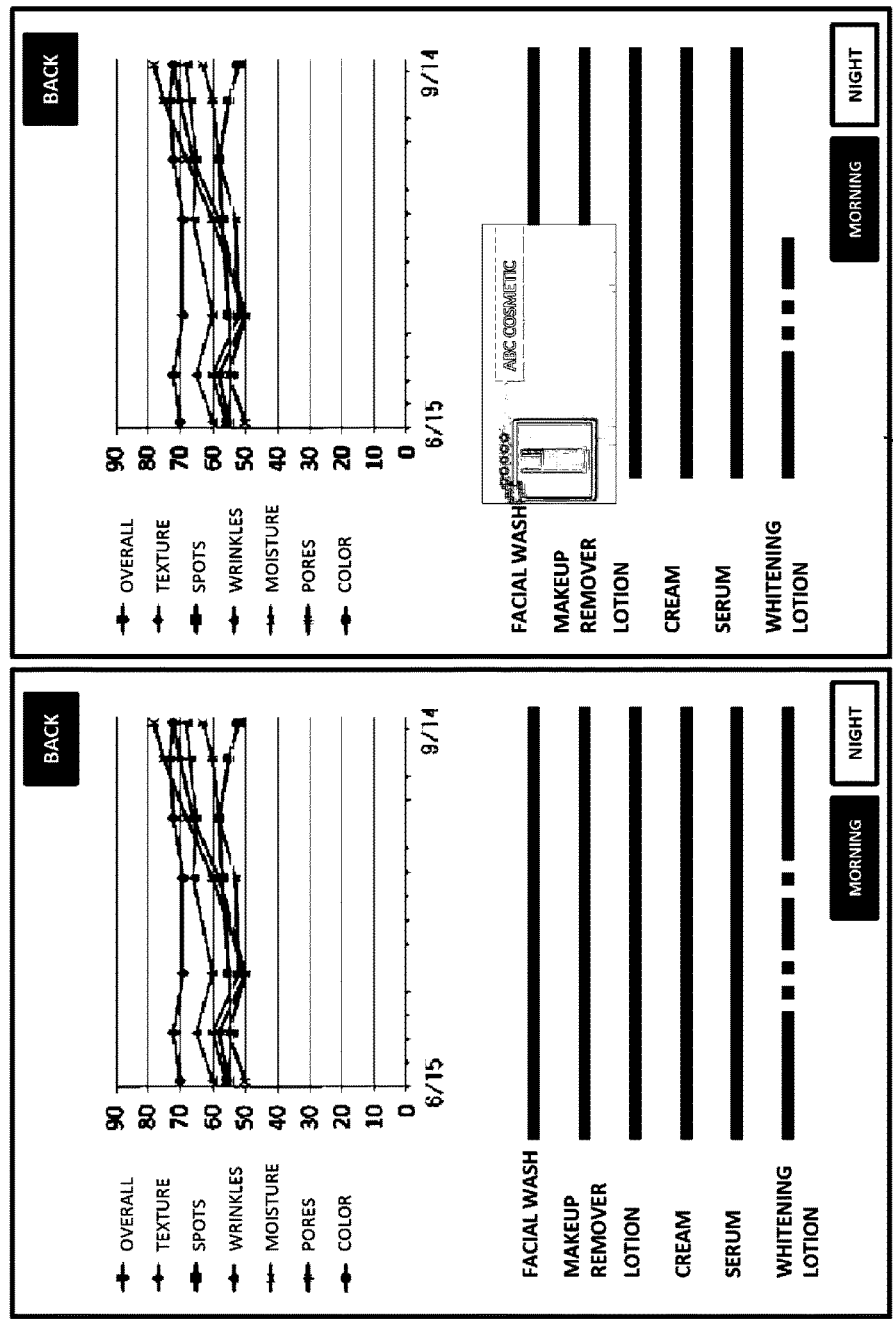
[Fig. 21]

[Fig. 22]

| TODAY'S 2012.11.8 | | | PAST RESULT 2012.4.8 ▼ | | |
|---|---|---|---|---|---|
| TIME | ☀ | ☾ | TIME | ☀ | ☾ |
| TEXTURE | | | TEXTURE | | |
| SPOTS | ○ | ○ | SPOTS | ◯ | ◯ |
| SKIN TYPE | NORMAL | NORMAL | SKIN TYPE | DRY | DRY |
| TEXTURE | 70 | 71 | TEXTURE | 65 | 60 |
| SPOTS | 75 | 75 | SPOTS | 70 | 68 |
| MOISTURE | 70 | 70 | MOISTURE | 58 | 55 |
| WRINKLES | 70 | 70 | WRINKLES | 70 | 70 |
| PORES | 65 | 58 | PORES | 60 | 60 |
| COLOR | 58 | 58 | COLOR | 65 | 65 |
| TODAY'S ADVICE | | | PAST ADVICE | | |

81

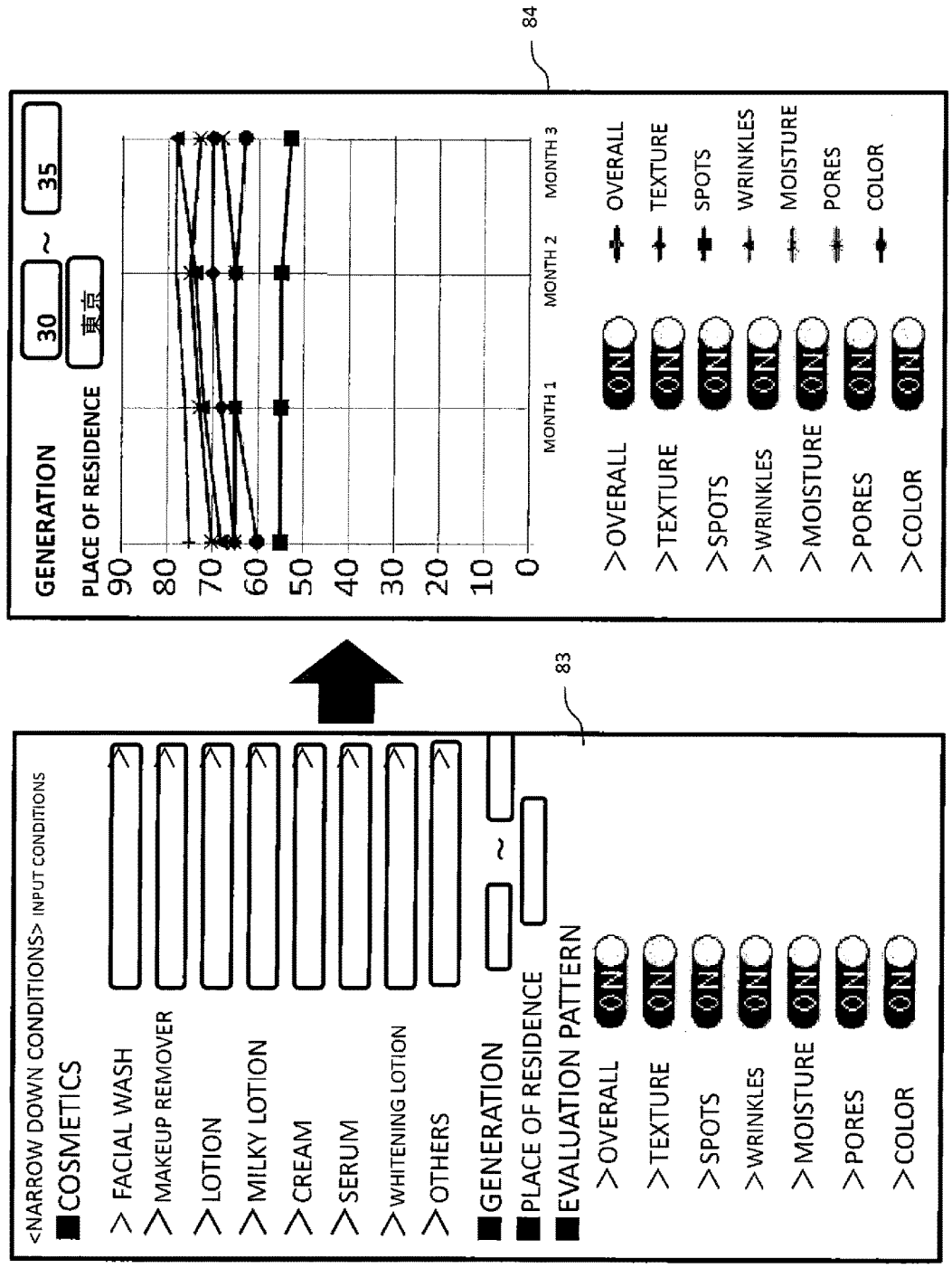
[Fig. 23]

[Fig. 24]

<<SEARCH CONDITION ITEM INPUT SCREEN>>

BACK

[ ] DATA INPUT DATE
[ ] GENERATION
[ ] SEX
[ ] SKIN TYPE
[ ] ADDRESS (COUNTRY)
[ ] ADDRESS (PREFECTURE)

ENTER

<<SEARCH CONDITION ITEM INPUT SCREEN>>

BACK

[ ] DATA INPUT DATE
[ ] GENERATION
[ ] SEX
[ ] SKIN TYPE
[ ] ADDRESS (COUNTRY)
[ ] ADDRESS (PREFECTURE)
[ ] ADDRESS (CITY, TOWN, VILLAGE)
[ ] USING LOTION
[ ] USING MILKY LOTION
[ ] USING CREAM
[ ] USING SERUM
[ ] USING WHITENING LOTION
[ ] BEAUTY CARE TYPE CODE

[ ] RANK RANGE OF SIMPLE ANALYSIS RESULT ON SKIN IMAGE
[ ] RANK RANGE OF SIMPLE ANALYSIS RESULT BY EVAPORIMETER
[ ] RANK RANGE OF SIMPLE ANALYSIS RESULT BY MELANIN METER
[ ] RANK RANGE OF OVERALL SIMPLE ANALYSIS RESULT

ENTER

[Fig. 26]

<<OUTPUT RANGE SELECTING SCREEN>>

BACK

[ ] GENERATION
[ ] ADDRESS 1
[ ] ADDRESS 2
[ ] SEX
[ ] DATA INPUT DATE
[ ] INPUT SKIN IMAGE
[ ] SIMPLE ANALYSIS RESULT ON SKIN

ENTER

<<OUTPUT RANGE SELECTING SCREEN>>

[BACK]

[ ] AGE
[ ] ADDRESS 1
[ ] ADDRESS 2
[ ] ADDRESS 3 (CITY, TOWN, VILLAGE)
[ ] SEX
[ ] DATA INPUT DATE
[ ] INPUT SKIN IMAGE
[ ] INPUT DATA OF EVAPORIMETER
[ ] INPUT DATA OF MELANIN METER
[ ] SIMPLE ANALYSIS RESULT ON SKIN IMAGE
[ ] SIMPLE ANALYSIS RESULT BY EVAPORIMETER
[ ] SIMPLE ANALYSIS RESULT BY MELANIN METER
[ ] OVERALL SIMPLE ANALYSIS RESULT

[ ] CLEANSING HISTORY DATA
[ ] FACIAL WASH HISTORY DATA
[ ] LOTION HISTORY DATA,
[ ] SERUM HISTORY DATA
[ ] MOISTURIZING CREAM HISTORY DATA
[ ] BEAUTY CARE DEVICE TYPE CODE
[ ] START DATE AND TIME OF BEAUTY CARE DEVICE
[ ] FINISH DATE AND TIME OF BEAUTY CARE DEVICE

[ENTER]

TODAY'S RESULT — 91a

2012.11.8

| TIME | ☀ | ☾ |
|---|---|---|
| TEXTURE | ▢ | ▢ |
| SPOTS | ◯ | ◯ |
| SKIN TYPE | NORMAL | NORMAL |
| TEXTURE | 70 | 71 |
| SPOTS | 75 | 75 |
| MOISTURE | 70 | 70 |
| WRINKLES | 70 | 70 |
| PORES | 65 | 58 |
| COLOR | 58 | 58 |

TODAY'S ADVICE

............

| BACK | DELETE FROM HISTORY |
|---|---|

| \[RESULT ON JAN. 31\] | | |
|---|---|---|
| 2012.11.8 | | |
| TIME | ☀ | ☾ |
| TEXTURE | | |
| SPOTS | ○ | ○ |
| SKIN TYPE | NORMAL | NORMAL |
| TEXTURE | 70 | 71 |
| SPOTS | 75 | 75 |
| MOISTURE | 70 | 70 |
| WRINKLES | 70 | 70 |
| PORES | 65 | 58 |
| COLOR | 58 | 58 |

TODAY'S ADVICE
............

[BACK]  [DELETE FROM HISTORY]

91b, 90b, 92b

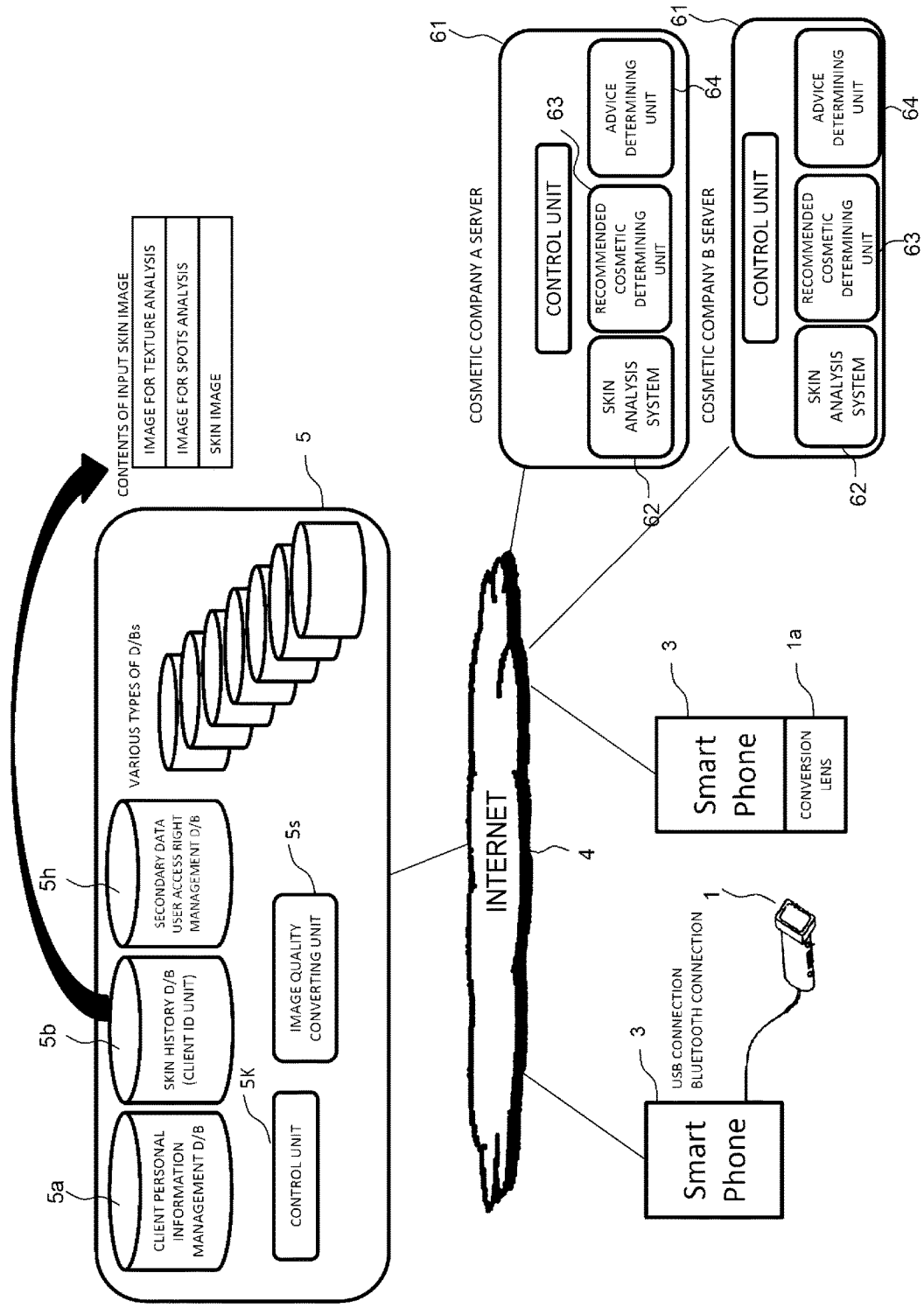
[Fig. 30]

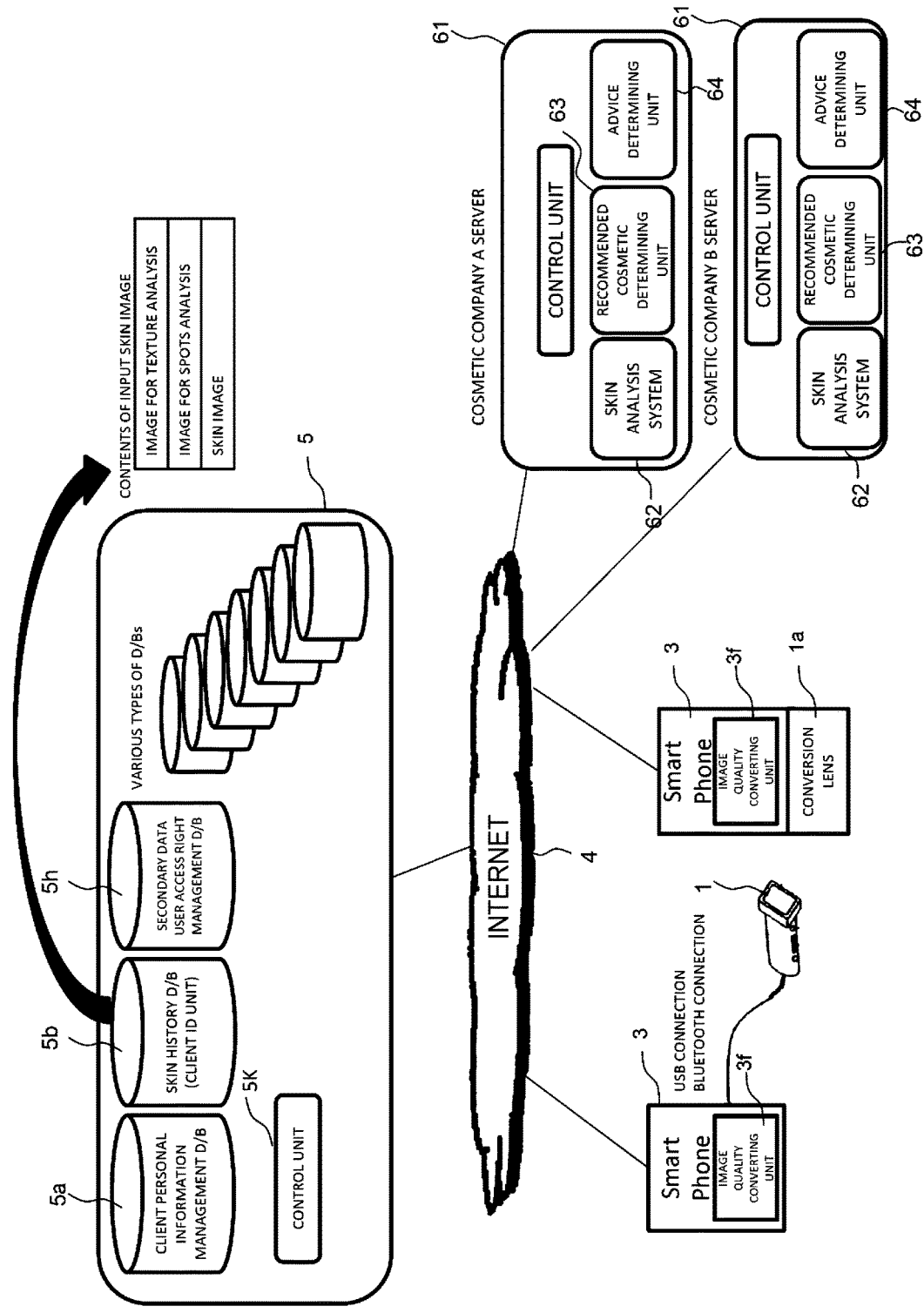

[Fig. 32]
[TABLE 2]
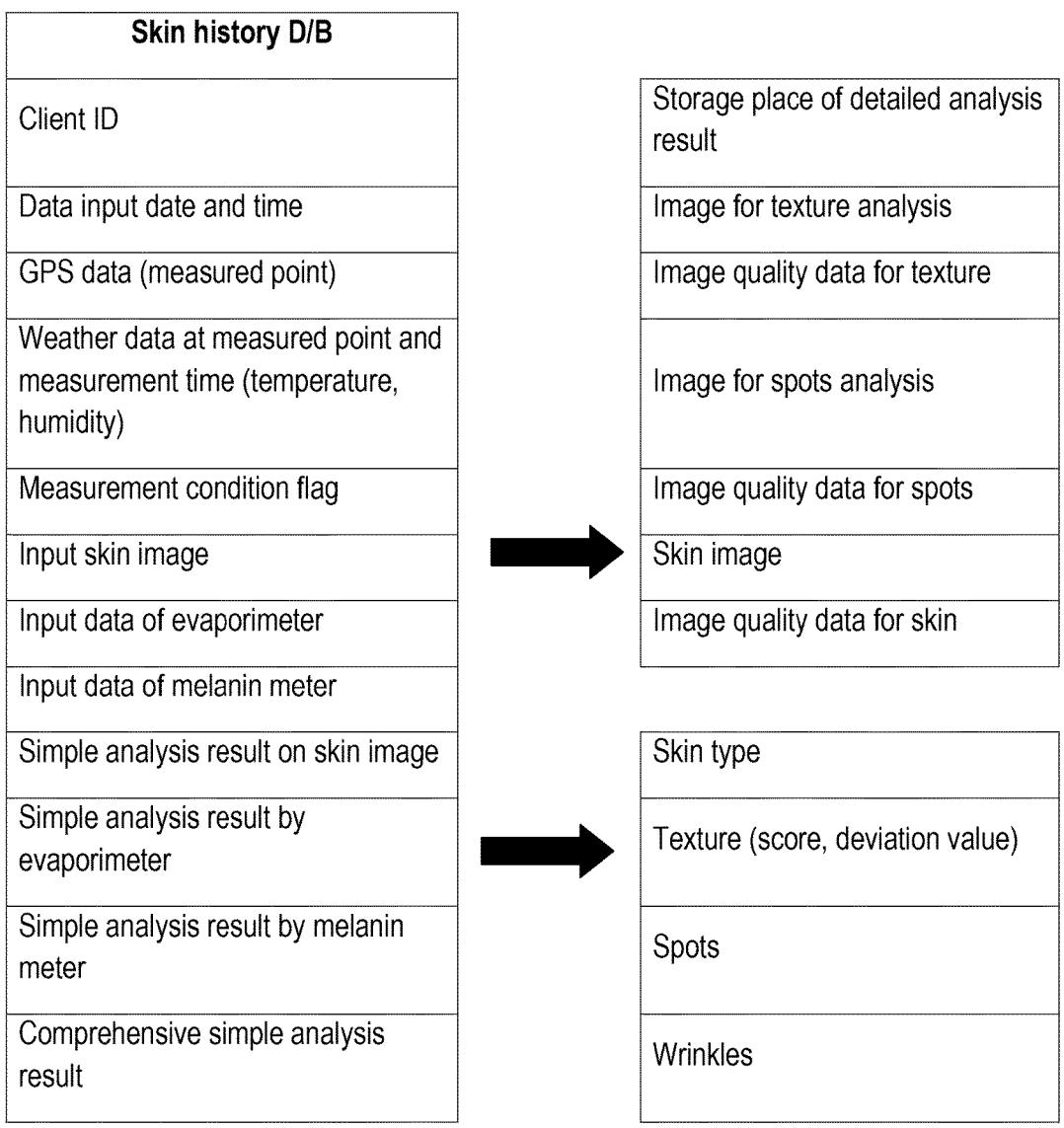

[Fig. 33]
[TABLE 3]
| Using cosmetic history D/B |
|---|
| Client ID |
| Facial wash history data |
| Makeup remover history data |
| Lotion history data |
| Milky lotion history data |
| Cream history data |
| Serum history data |
| Whitening lotion history data |
| Others |
| Cosmetic category | Use start date | Use start date | Use finish date |
|---|---|---|---|
| 1 | 123001 | 20120401 | 20120630 |
| 1 | 123003 | 20120701 | 20120931 |
| 1 | 123005 | 20121001 | |
| 1 | 123008 | 20121101 | |
| 1 | 123010 | | |
| | | | |

[Fig. 34]

[TABLE 4]

| Category | NO. |
|---|---|
| Facial wash | 1 |
| Makeup remover | 2 |
| Lotion | 3 |
| Milky lotion | 4 |
| Cream | 5 |
| Serum | 6 |
| Whitening lotion | 7 |
| Others | 8 |

[Fig. 35]

[TABLE 5]

| Care chart D/B |
|---|
| Client ID |
| Year, month, date |
| Morning/Night |
| Using cosmetic data |

→

| 2012/9/21 | 2012/9/21 | 2012/9/21 |
|---|---|---|
| Morning | Night | Morning |
| 123005 | 123008 | 123005 |
| 212345 | 212345 | 212345 |
| 312345 | 312340 | 312345 |
|  |  |  |

[Fig. 36]

[TABLE 7]

| Detailed analysis result D/B |
|---|
| Client ID |
| Analysys date and time |
| Detailed analysis result |
| Advice data |
| Recommended cosmetic data |
|  |

→

| Skin type |
|---|
| Texture (score, deviation value) |
| Spots |
| Wrinkles |
| Dryness |
| Pores |
| Color (sunburn, darkening) |

[Fig. 37]

[TABLE 10]

| Device information D/B |
|---|
| Management table for product serial number of camera for skin |
| Management table for product serial number of evaporimeter |
| Management table for product serial number of melanin meter |
| Management table for product serial number of other sensor |
|  |
| Management table for product serial number of ion cleansing device |
| Management table for product serial number of ion introducing device |
| Management table for product serial number of roller beauty device |
| Management table for product serial number of ultrasonic wave beauty device |
| Management table for product serial number of other beauty care product |

| Product serial number of ultrasonic wave beauty device | Client ID (1) | Client ID (2) | Client ID (3) |
|---|---|---|---|
| 20120101001 | A002 | | |
| 20120101002 | A003 | B054 | |
| 20120101003 | A005 | | |
| ⋮ | | | |
| ⋮ | | | |
| ⋮ | | | |
| | | | |

[Fig. 38]  [TABLE 11]

| Secondary data user access right management D/B |
|---|
| User ID Client ID |
| User's user ID |
| User password |
| User search level |
| User access level |
| Billing information |

Example of definition of search level

| Search level 1 | Search level 2 |
|---|---|
| Client ID | Client ID |
| Age | Age |
| Sex | Sex |
| Address 1 | Address 1 |
| Address 2 | Address 2 |
| Data input date and time | Address 3 |
| | Data input date and time |

Example of definition of access level

| Access level 1 | Access level 2 | Access level 3 |
|---|---|---|
| Client ID | Client ID | Client ID |
| Age | Age | Age |
| Address 1 | Address 1 | Address 1 |
| Address 2 | Address 2 | Address 2 |
| Sex | Address 3 (city, town, village) | Address 3 (city, town, village) |
| Data input date and time | Sex | Sex |
| Input skin image | Data input date and time | Data input date and time |
| Input data of evaporimeter | Input skin image | Input skin image |
| Input data of melanin meter | Input data of evaporimeter | Input data of evaporimeter |
| Simple analysis result on skin image | Input data of melanin meter | Input data of melanin meter |
| Simple analysis result by evaporimeter | Simple analysis result on skin image | Simple analysis result on skin image |
| Simple analysis result by melanin meter | Simple analysis result by evaporimeter | Simple analysis result by evaporimeter |
| Comprehensive simple analysis result | Simple analysis result by melanin meter | Simple analysis result by melanin meter |
| | Comprehensive simple analysis result | Comprehensive simple analysis result |
| | Cleansing history data | Cleansing history data |

[Fig. 39]
[TABLE 15]
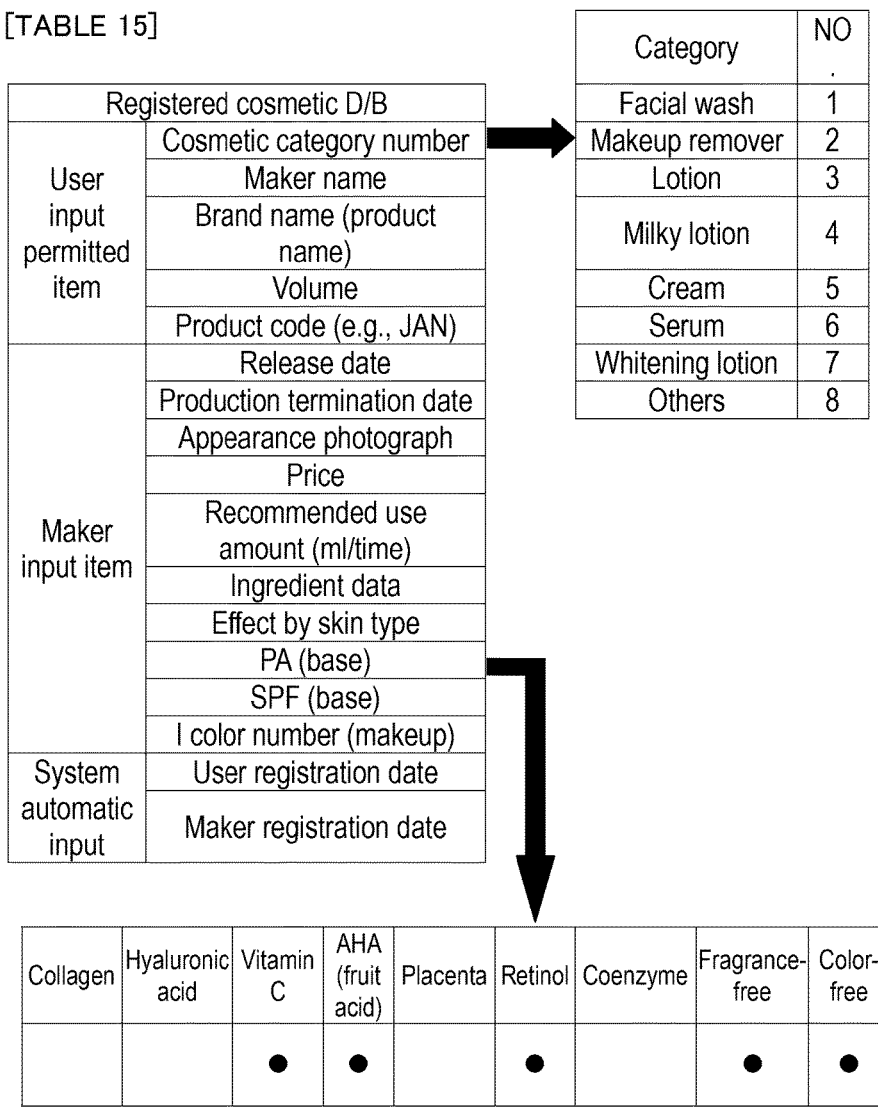

[Table 17]

| Skin history D/B |
| --- |
| Client ID |
| Data input date and time |
| GPS data (measured point) |
| Weather data at measurement time and measured point (temperature, humidity) |
| Measurement condition flag |
| Input skin image (texture/spots) |
| Simple analysis result on skin image |
| Skin image deletion flag |
| Input data of evaporimeter |
| Simple analysis result by evaporimeter |
| Evaporimeter data deletion flag |
| Input data of melanin meter |
| Simple analysis result by melanin meter |
| Melanin meter data deletion flag |
| Comprehensive simple analysis result |
| Storage place of detailed analysis result |

| |
| --- |
| Skin type |
| Texture (score, deviation value) |
| Spots |
| Wrinkles |

| |
| --- |
| Image for texture analysis |
| Image quality data for texture |
| Image for spots analysis |
| Image quality data for spots |
| Skin image |
| Image quality data for skin |

FIG. 40

MANAGEMENT SYSTEM FOR SKIN CONDITION MEASUREMENT ANALYSIS INFORMATION AND MANAGEMENT METHOD FOR SKIN CONDITION MEASUREMENT ANALYSIS INFORMATION

TECHNICAL FIELD

The present invention relates to a management system for skin condition measurement analysis information and a management method for skin condition measurement analysis information, in which measurement of skin condition and analysis on a measurement result are performed and also data of a measurement result and an analysis result (measurement data and analysis result data) is managed by connecting a skin measurement apparatus to a mobile client (mobile terminal) connectable to a network mainly by radio such as a smartphone, a mobile phone, and a tablet and transmitting and receiving the data via the network.

BACKGROUND ART

Generally, in selling cosmetics and beauty treatment apparatuses for skin care (skin care device: beauty care device), a cosmetic for skin care, a facial wash, etc. and an apparatus for skin care corresponding to skin condition are sold after skin condition is grasped, for example, by magnifying and photographing the skin by using a camera for skin to find out the skin condition. In this case, there is a case in which not only a skin condition measuring device that magnifies and photographs a skin surface (skin condition measuring unit: camera for skin) but also various kinds of measuring instruments for skin, such as a measuring apparatus of measuring moisture content of the skin, are used, and the skin condition is sometimes determined from a magnified image of the skin and is sometimes determined from the moisture content of the skin.

In such a case, it has been necessary to go to a shop where the measuring instrument for skin is provided to measure the skin condition and a shop staff that can determine the skin condition from measurement result and can give an advice on a skin care method based on the skin condition is available. However, regularly confirming the skin condition has been difficult because going to the shop is sometimes bothersome and being encouraged to purchase some products after receiving such service at the shop is annoying.

Thus, a skin condition measuring device as a peripheral device is connected to a portable wireless terminal capable of accessing to the Internet via a wireless telephone line such as a mobile phone, a smartphone, and a tablet, or via other wireless communication lines. Alternatively, a built-in device such as a camera provided in the portable wireless terminal is used as at least a part of the skin condition measuring device. Then, there is a proposed system capable of analyzing the skin condition without going to cosmetics selling shops by transmitting data of the measurement result of the skin condition measuring device to a server of a vendor analyzing skin condition from the measurement result with use of the portable wireless terminal (see Patent Literatures 1 to 5). In this case, the server having received the measurement data is to perform, for example, automatic analysis on the measurement result and making an operator input the analysis result by displaying the measurement data.

In this case, the skin condition measuring device is needed to be purchased, but the skin measurement can be regularly performed for a relatively short period without giving any burden to a user by using the above-described system for skin measurement.

CITATION LIST

Patent Literatures

Patent Literature 1: JP 2005-148797 A
Patent Literature 2: JP 2004-354207 A
Patent Literature 3: JP 2005-56165 A
Patent Literature 4: JP 2002-15068 A
Patent Literature 5: JP 2002-366651 A

SUMMARY OF INVENTION

Technical Problem

By the way, unless the user uses the camera built inside the wireless mobile terminal, basically it is necessary to purchase the skin condition measuring device such as a camera for skin. Further, sometimes the user is charged for having the measurement result analyzed, and the user might hesitate to find out the skin condition regularly.

Meanwhile, the server side to which the measurement data is sent can accumulate the measurement data and the analysis result thereof, for example. Additionally, to have the measurement data analyzed, member registration is sometimes required with a company that provides the service, and on the occasion of member registration the user is sometimes required to input personal information such as a name, an address, an e-mail address, a birthday, and sex, and is sometimes requested to cooperate for answering a questionnaire.

In this case, when the number of users increases, the data such as the measurement result of the skin and the analysis result thereof, and information from data at the time of member registration or from data of the questionnaire, such as age, sex, and a place of residence are accumulated correlated to the data.

In the case where the accumulated data amount is increased, the data can be analyzed and utilized for developing new skin care products; however, under the present circumstances, effective utilization of the accumulated data is not sufficiently achieved by having the skin measurement result transmitted.

Additionally, considering a relation between the skin condition and the cosmetic for skin care (including facial wash relation), the user wishes to find out the relation between the using cosmetic for skin care and change of the skin condition, i.e., whether the currently using cosmetic for skin care has effect of improving the skin condition or not. That is, the user wishes to find out whether the currently using cosmetic is suitable for the user's skin or whether there is other cosmetic that is more suitable for the user's skin. However, according to skin analysis in the above-described shop of the cosmetic company or the like, only information of cosmetics that are products of the cosmetic company can be acquired.

From a standpoint of the cosmetic company, the information of the user's skin condition can be acquired with use of the measuring instruments for skin at the shop as described above. In this case, customer information such as the personal information including an address and a name, and information of the using cosmetic and an element that affects the skin can be acquired from questions, questionnaires, etc. made by the shop staff to the user. Additionally, in the case where the user uses the own company's product, data such as influence on the skin in the case of using the own company's product can be acquired. However, there has been such a problem that it is not possible to acquire the data of the skin condition, etc. of a user who purchases the cosmetics at a shop not included in a sales system of the cosmetic company or by using mail order, for example, without measuring the skin condition at the shop, etc. Additionally, it has been difficult to acquire information of the influence on the skin in the case of using products of other company and the like.

Currently, there are domestically many cosmetic makers (here, the makers include distributor firms as well) and also there is new entry from other industries, and additionally, there are users who use overseas cosmetics, and a large number of cosmetics are traded in the market place. The user needs to select cosmetics suitable for the user from among the large number of cosmetics, and it is demanded that the user can easily determine whether or not there is a certain extent of effect in the case of using the cosmetic.

Additionally, the cosmetic company can have advantages in business strategy on the products in the case where the cosmetic company can acquire the data of respective users, for example, what kind of ingredient is contained in a cosmetic when there is effect on the respective users having different skin types as the skin condition, and what kind of cosmetic is preferred by the users having the different skin types. In product development, an information amount of clinical trials executed is limited, and in the case where feedback data is acquired from many users after selling the own company's products, the data can be effectively used for next product development and further, in the case where information of products of other companies is acquired, the information can be further effectively used. Accordingly, the makers that are the cosmetics companies demand to acquire the data of the users having used the cosmetics after sales.

The present invention is made in view of the above-described circumstances, and is directed to providing a management system for skin condition measurement analysis information and a management method for skin condition measurement analysis information, in which service can be offered free of charge and the cost of a skin condition measuring device can be reduced by effectively using data such as received measurement data in the case where an analysis result on the measurement data can be acquired by connecting the skin condition measuring device to a user client (smartphone) and transmitting the measurement data by the skin condition measuring device to a server of a company providing a service of analyzing the measurement data.

Solution to Problem

A management system for skin condition measurement analysis information according to the present invention includes:

a skin condition measuring device configured to measure skin condition;

a user client used by a user of the skin condition measuring device, connected to the skin condition measuring device so as to be able to transmit and receive data, and also connected to a network to transmit and receive data;

a data management server configured to be capable of performing transmission and receipt of data with the user client via the network;

an analysis result outputting unit configured to receive analysis result data of the skin condition obtained by analyzing measurement data measured by the skin condition measuring device, output the analysis result data to be displayable on the user client, and also output the analysis result data to be storable in the data management server; and a contractor client configured to perform transmission and receipt of data with the data management server based on a contract for acquiring data from the data management server, wherein the user client includes:

a user data transmitting unit configured to transmit user data input by the user and also including personal information of the user and including a unique and no duplicative ID for each user to the data management server based on a request from the data management server;

a measurement data transmitting unit configured to transmit received measurement data and the input client ID to the data management server when the measurement data measured by the skin condition measuring device is received from the skin condition measuring device; and an analysis result display unit configured to display analysis result data when the analysis result data on the measurement data is received from the analysis result outputting unit, wherein the data management server includes:

a user data database in which user data including the client ID received from each of a plurality of user clients is registered;

a measurement data database in which measurement data received from the user client, analysis result data received from the analysis result outputting unit, accompanying data excluding predetermined personal information from the user data, and the client ID are registered correlated one another, and also at least the measurement data and the analysis result data are registered as a history based on an acquisition time of the data;

a contractor database in which a contractor 1D set for each of the contractors is registered; and a data providing unit configured to collate a contractor ID input from the contractor client with the contractor database when a request is made from the contractor client to acquire data registered in the measurement data database, and transmit the data registered in the measurement data database to a contractor client, and wherein the contractor client includes:

a data requesting unit configured to transmit the contractor ID and also request data registered in the measurement data database to the data management server; and a receiving and storing unit configured to receive and store data transmitted from the data management server based on a request of the data requesting unit.

According to the above-described configuration, the measurement data of the skin condition measured by the skin condition measuring device is to be transmitted to the data management server via the network by a user mobile terminal.

On this occasion, the user needs to set, for example, a client ID and inputs various kinds of data in accordance with the request from the data management server. On this occasion, for example, a name, an address, various kinds of phone numbers, an e-mail address, etc. may be input as predetermined personal information that is the user data.

Additionally, credit card information for settlement may be included as the predetermined personal information in the case of enabling purchase of products and service in the management system for skin condition measurement analysis information. Additionally, information such as using cosmetics, skin care articles, and supplements may be optionally input as the user data based on the request from the data management server as a questionnaire or the like.

In the data management server, the user data is registered in the user data database in the case where the user data is input from the user client. In the user data database, the user data can be retrieved using the client ID.

Additionally, the user client, for example, executes measurement of the skin condition by the skin condition measuring device connected based on the user's operation and obtains the measurement data, and then transmits the measurement data to the data management server together with the client ID.

The analysis result data obtained based on the measurement data is received by the analysis result outputting unit, and transmitted to the user client from the analysis result outputting unit, for example, via the data management server, e-mail, or the like, and the analysis result data can be viewed at the user client. Note that the analysis result can be acquired by analyzing the measurement data, using various kinds of known skin analysis methods.

Additionally, the measurement data, the analysis result data, and the accompanying data excluding the predetermined personal information from the user data are registered correlated to the client ID in the measurement data database.

In the accompanying data excluding the predetermined personal information from the user data, the predetermined personal information is basically information with which an individual is likely to be specified, for example, a name, an address, a phone number, an e-mail address, credit card information, and so on. The accompanying data excluding the predetermined personal information from the user data includes, for example, data of answers to questionnaires, such as using cosmetics, skin care articles (body oil, bath powder, etc.), skin care devices (beauty devices), regularly taking supplement, and modified personal information that cannot specify an individual, such as a place of residence (a rough address such as a prefecture or a city), a roughage (for example, teenager, twenties, thirties, etc.), and date that can be obtained on the occasion of measurement, such as a measurement date and time.

Here, the user can repeatedly execute measurement and analysis on the skin condition, and for example, the measurement data and the analysis result data can be read out from the measurement data database in chronological order based on the measurement date and time of the measurement data and a receiving date and time, etc. at the data management server.

For example, many users who use the service of analyzing the measurement data of the skin condition are obtained by offering the service of analyzing the measurement data of the skin condition free of charge, and thus the measurement data of many users is accumulated in the measurement data database, and also, measurement data in chronological order is likely to be acquired by having each of the users repeatedly use the analysis service.

In this case, a maker developing various kinds of cosmetics and skin care articles can utilize the measurement data of the skin condition accumulated in the measurement data server for product development, skin research, and so on. Additionally, in the measurement data server, the accompanying data excluding the predetermined personal information from the user data input by the user is correlated to the measurement data by using the client ID. Here, in the case of having the user input, for example, the using cosmetics, skin care articles, etc. by a request from the data management server side on the occasion of inputting the user data, more useful data can be obtained in comparison to the case of obtaining only the measurement data.

According to the present invention, a contract enables the measurement data, the analysis result data, and the accompanying data to be browsed. On this occasion, a kind of the accompanying data that can be browsed may be determined for each contractor ID of each contractor based on the contract. In the contractor database, a kind of the accompanying data that can be browsed from the contractor client corresponding to each contractor ID may be registered correlated to the contractor ID. Thus, on the occasion of collating the contractor ID of the contractor client, the kind of the accompanying data that can be browsed at the contractor client is set and only the kind of the accompanying data correlated to the contractor ID can be browsed at the contractor client.

In this case, the kind of the accompanying data which the contractor has browsed is to be determined at the time of contract. On this occasion, plural kinds of the accompanying data may be made browsable or all kinds of the accompanying data may be made browsable.

On this occasion, the kinds of the accompanying data are classified into ranks and higher-rank accompanying data may be made browsable as a browse level determined at the time of contract becomes higher.

In the data management server, when a request for browsing data is received from the contractor client together with the contractor ID, the contractor database may be searched by using the contractor ID, and the kinds of the accompanying data, measurement data, and analysis result data may be transmitted to the contractor client to be browsable based on the kind of the accompanying data correlated to the contractor ID.

For example, the contractor selects a necessary kind of the accompanying data from various kinds of the accompanying data at the time of contract, and makes the contract with an operator of the data management server. On this occasion, for example, the contract is made to pay an extra fee corresponding to each kind. Thus, the contractor can obtain the useful accompanying data.

Thus, the operator of the data management server (e.g., a maker and distributor firm of the skin condition measuring device) can gain corresponding price for browsing of the analysis result data, measurement data, and accompanying data on the occasion of contract with the contractor (e.g., a cosmetic company such as maker and distributor firm of cosmetics, a maker and distributor firm of skin care articles, a maker and distributor firm of beauty devices).

By such a price, operating cost for the data management server and profits can be obtained without charging any fee to the user. Since there is no charge to the user, sales of the skin condition measuring device can be promoted and also analysis on the measurement data by using the skin condition measuring device can be promoted. Thus, the data in the measurement data database can be enriched. Thus, the number of contractors wishing to use the analysis result data, the measurement data, and the accompanying data can be increased, and revenue growth can be achieved.

According to the above-described configuration of the present invention, preferably, in the measurement data database, the measurement data including a plurality of data blocks, the analysis result data including a plurality of data blocks, and the accompanying data including a plurality of data blocks are registered correlated one another, and also respective search items are set for at least a part of the data blocks, and the data of the data blocks set with the search items is narrowed down by inputting a conditions in the search items, and the data associated with the narrowed-down data can be retrieved, in the contractor database, the search items are classified into a plurality of levels and registered as a search item for each search level, and also the data blocks to which the data that can be output as a search result belongs is classified into a plurality of levels and registered as a data block for each access level, and the search level and the access level are registered correlated to the contractor ID, and the data management server searches the contractor database by using the contractor ID input from the contractor client and extracts the search level and the access level correlated to the contractor ID with respect to the contractor client, and includes:

a search limiting unit configured to permit searching the measurement data database by inputting a search condition from the contractor client only with respect to the search item classified into the extracted search level, and permit outputting, to the contractor client, only the retrieved data belonging to the data block classified into the extracted access level among the data blocks; and a search display unit configured to display, at the contractor client, the search items classified into the extracted search level based on the contractor ID by the search limiting unit such that a search item to which a search condition is input can be selected from the search items, and display the data blocks classified into the extracted access level based on the contractor ID by the search limiting unit such that the data block to which data that outputs a search result belongs can be selected from the blocks.

According to the above-described configuration, for example, the data blocks of the data that can output the search item and search result in the measurement data database is to be limited by the search level and the access level; however, the contractor (a secondary user of measurement data and analysis result data) can retrieve necessary data and reduce expense by determining and making a contract for the search level and access level that are considered to be necessary by the contactor in the case where usage fee is varied depending on the search level and the access level. Additionally, since only the search item corresponding to the search level is displayed to the contractor client in a selectable manner, and also only the data blocks to which the acquirable data belongs are displayed in a selectable manner, there is no case of inputting a condition in a search item that cannot be retrieved based on the search level or requesting output of the data that cannot be output based on the access level. Hence, the contractor can execute efficient search.

Additionally, according to the above-described configuration of the present invention, preferably, cosmetic data that is input from the user client as the accompanying data and can specify a cosmetic used by the user of the skin condition measuring device is registered correlated to a use time of the cosmetic in the measurement data database, and analysis result data of the acquisition time corresponding to the use time correlated to the cosmetic data can be retrieved from the contractor client together with the cosmetic data.

According to the above-described configuration, the contractor client can examine, for example, a relation between the using cosmetic and the analysis result data of the skin condition. For example, it can be find out that the skin condition of a user using a cosmetic does not change while the skin condition of other user using a different cosmetic is gradually improved or the like. That is, the contractor such as a cosmetic company can confirm effects of the own company products and investigate effects of other company products.

In this case, since as the number of users increases, many samples can be obtained, more detailed investigation can be executed. Additionally, in the case where a generation, a place of residence, a frequency of use of a cosmetic, a use amount of a cosmetic and the like are found out as the accompanying data, investigation corresponding to the user's circumstance, use condition of the cosmetic can be also executed. That is, further useful data for product development can be obtained compared to the case of the data g specifying the using cosmetic in addition to the analysis result on the measurement data of the skin condition.

Note that the measurement data corresponding to the using cosmetic may be obtained in addition to the analysis result data.

Additionally, preferably, measurement of the skin condition and analysis on the measurement data are regularly and continuously executed by a user.

Additionally, according to the above-described configuration of the present invention, preferably, in the measurement data database, cosmetic data that is received from the user client and also can specify a cosmetic used by the user of the skin condition measuring device is registered correlated to a use time of the cosmetic and the client ID input from the user client, in addition to the analysis result data acquired for each measurement along chronological order by the skin condition measuring device and also registered correlated to an acquisition time as the history based on the acquisition time of the analysis result data, the user client is capable of searching the measurement data database for the analysis result data and the cosmetic data correlated to the client ID input from the user client, in conformity with the acquisition time of the analysis result data and the use time of the cosmetic, and the analysis result data correlated to the retrieved acquisition time and the cosmetic data correlated to the use time which is same as the acquisition time can be displayed in parallel, and also at least one of a chronological display in which details of change in the analysis result data along chronological order can be recognized by arranging in the chronological order of the acquisition time and displaying the analysis result data at the acquisition time included in a period selected by the user; and a comparative display in which a difference of the analysis result data with the acquisition time can be compared by simultaneously displaying the analysis result data at a plurality of the acquisition times selected by the user is displayable.

According to the above-described configuration, in the case where the user continuously measures the skin condition and acquires the analysis result data based on the measurement data obtained by the measurement, the cosmetic data indicating the using cosmetic and the analysis result data of analyzing the measured skin condition can be viewed at the same time, and also details of change in the skin condition during a selected period can be recognized by viewing the chronological display. That is, the currently using cosmetic and the change with time in the skin condition can be recognized, and it becomes possible to determine whether the skin condition is good or not, whether the skin condition tends to improve or not, and the like while the cosmetic is being used.

Additionally, it becomes possible to determine a difference of the skin condition in the case of continuously using the same cosmetic or the like by viewing the comparative display and thus comparing the analysis results of a plurality of acquisition times selected. For example, whether or not the skin condition is better than before can be determined by viewing and comparing the analysis result data at the latest acquisition time with the analysis result data in any period before the present time. For example, the chronological display is especially effective for determining change in the skin condition for a relatively short period and the comparative display is especially effective for evaluating change in the skin condition for a relatively long period.

A management method for skin condition measurement analysis information according to the present invention is a management method for skin condition measurement analysis information executed in a management system for skin condition measurement analysis information that includes:

a skin condition measuring device configured to measure skin condition;

a user client used by a user of the skin condition measuring device, connected to the skin condition measuring device so as to be able to transmit and receive data, and also connected to a network so as to transmit and receive data;

a data management server configured to be capable of performing transmission and receipt of data with the user client via the network;

an analysis result outputting unit configured to receive analysis result data of the skin condition obtained by analyzing measurement data measured by the skin condition measuring device, output the analysis result data to be displayable on the user client, and also output the analysis result data to be storable in the data management server; and a contractor client configured to perform transmission and receipt of data with the data management server based on a contract to acquire data from the data management server, wherein the user client executes:

a user data transmitting step of transmitting user data input by a user and also including personal information of a user and including a unique and no duplicative ID for each user to the data management server based on a request from the data management server;

a measurement data transmitting step of transmitting received measurement data and the client ID to the data management server when the measurement data measured by the skin condition measuring device is received from the skin condition measuring device; and an analysis result displaying step of displaying analysis result data when the analysis result data on the measurement data is received from the analysis result outputting unit, wherein the data management server executes:

a user data registering step of registering user data that including the client ID received from each of a plurality of user clients in a user data database;

a measurement data registering step of registering the measurement data received from the user client, analysis result data received from the analysis result outputting unit and, accompanying data excluding predetermined personal information from the user data, and the client ID in a measurement data database, correlated one another, and also registering on the occasion of registration at least the measurement data and the analysis result data as a history based on an acquisition time of the data in the measurement data database; and a data providing step of collating a contractor ID input from the contractor client with the contractor database when acquisition of data registered in the measurement data database is requested from the contractor client, and transmitting the data registered in the measurement data database to a contractor client, and wherein the contractor client executes:

a data requesting step of transmitting the contractor ID and also requesting the data management server for data registered in the measurement data database; and a receiving and storing step of receiving and storing data transmitted from the data management server based on a request from the data requesting unit.

According to the above-described configuration of the present invention, preferably, the data management server is capable of:

narrowing down data of data blocks set with search items by inputting conditions in the search items and retrieving the data associated with the narrowed-down data from the measurement data database in which the measurement data including the plurality of data blocks, the analysis result data including the plurality of data blocks, and the accompanying data including the plurality of data blocks are registered correlated one another, and also the respective search items are set for at least a part of the data blocks; and extracting a search level and an access level correlated to the contractor ID by searching, using the contractor ID input from the contractor client, the contractor database in which the search items are classified into a plurality of levels and registered as a search item for each search level, and also the data blocks to which data that can be output as a search result belongs is classified into a plurality of levels and registered as a data block for each access level, and the search level and the access level are registered correlated to the contractor ID, and wherein the data management server executes:

a search limiting step of permitting searching the measurement data database by inputting a search condition from the contractor client only for the search item classified into the extracted search level, and permitting outputting, to the contractor client, only the retrieved data belonging to the data block classified into the extracted access level among the data blocks; and a search displaying step of displaying, on the contractor client, the search items classified into the extracted search level based on the contractor ID by the search limiting unit such that a search item to which a search condition is input can be selected from the search items, and displaying the data blocks classified into the extracted access level based on the contractor ID by the search limiting unit such that a data block to which data that outputs a search result belongs can be selected from the blocks.

Additionally, according to the above-described configuration of the present invention, preferably, the contractor client searches the measurement data database in which cosmetic data that is input from the user client as the accompanying data and can specify a cosmetic used by the user of the skin condition measuring device is registered correlated to a use time of the cosmetic, for analysis result data of the acquisition time corresponding to the use time correlated to the cosmetic data together with the cosmetic data.

Additionally, according to the above-described configuration of the present invention, preferably, the user client executes:

retrieving, from the measurement data database in which cosmetic data that is received from the user client and also can specify a cosmetic used by the user of the skin condition measuring device is registered correlated to a use time of the cosmetic and the client ID input from the user client, in addition to the analysis result data acquired for each measurement along chronological order by the skin condition measuring device and also registered correlated to the acquisition time as the history based on the acquisition time of the analysis result data, the cosmetic data and the analysis result data correlated to the client ID input from the user client, in conformity with the acquisition time of the analysis result data and the use time of the cosmetic; and displaying the analysis result data correlated to the retrieved acquisition time and the cosmetic data correlated to the use time which is same as the acquisition time are displayed in parallel, and also displaying at least one of a chronological display in which details of change in the analysis result data along chronological order can be recognized by arranging in the chronological order of the acquisition time and displaying the analysis result data at the acquisition time included in a period selected by the user; and a comparative display in which a difference of the analysis result data with the acquisition time can be compared by simultaneous displaying the analysis result data at a plurality of the acquisition times selected by the user.

According to the above-described management method for skin condition measurement analysis information, the effects same as those of the corresponding management system for skin condition measurement analysis information can be obtained.

Additionally, it is also possible to apply following configurations to the present invention.

For example, in the management system for skin condition measurement analysis information according to the present invention, the user client may include:

a data browsing requesting unit configured to transmit the client ID and also request transmission of respective data stored correlated to the client ID from the measurement data database or the user data database; and a data displaying unit configured to display the transmitted data when the data requested by the data browsing requesting unit is transmitted from the data management server, and the data management server may include a data transmitting unit for data browsing configured to transmit, to the user client corresponding to the client ID transmitted from the data browsing requesting unit, the data registered in the measurement data database or the user data database and also correlated to the client ID transmitted from the user client, based on the request of the data browsing requesting unit.

According to the above-described configuration of the present invention, the data management server may extract, in response to a request from the user client, two or more pieces of the measurement data and/or the analysis result data of different acquisition times from the measurement data and/or the analysis result data stored in the measurement data database as the history based on the acquisition times, and transmit the extracted data to the user client, and the user client may include a comparative display unit configured to display the measurement data and/or the analysis result data of the different acquisition times in order of acquisition times such that the data can be compared each other.

Additionally, according to the above-described configuration of the present invention, the skin condition measuring device may be provided with a device authentication storage unit configured to store an authentication character string for authenticating the skin condition measuring device and also output the stored authentication character string outside, the user client may include a device authentication transmitting unit configured to transmit the authentication character string output from the connected skin condition measuring device to the data management server, and the data management server may include:

an authenticating unit configured to authenticate the authentication character string; and a non-authenticated device excluding unit configured to execute control so as not to output the analysis result data of the measurement data transmitted from the user client having the authentication character string that has not been authenticated by the authenticating unit.

Additionally, according to the above-described configuration of the present invention, the skin condition measuring device may be a camera for skin configured to take a close-up photo of skin and output image data as the measurement data, the measurement data transmitting unit in the user client may transmit the image data output from the skin condition measuring device to the data management server, the image data may be registered in the data analysis database as the measurement data, the data management server may include:

a calibration unit configured to generate calibration data of calibrating an individual difference of the skin condition measuring device based on the image data photographed by the skin condition measuring device in accordance with a predetermined condition; and a calibration database configured to register the calibration data generated by the calibration unit and the authentication character string correlated each other, and the analysis result acquiring unit may be configured to acquire the calibration data from the calibration database based on the authentication character string, calibrate the image data by the calibration data, or calibrate the skin condition measuring device based on the calibration data.

Additionally, according to the above-described configuration of the present invention, a skin care device that can be controlled from the user client by being connected to the user client may be provided, the user client or the data management server may include:

a skin care database in which a control method for the skin care device is registered, correlated to the analysis result data;

a skin care data acquiring unit configured to acquire the analysis result data from the measurement data database based on the client ID output from the user client connected to the skin care device; and a control method acquiring unit configured to acquire the control method for the skin care device from the skin care database based on the analysis result data acquired by the skin care data acquiring unit, and the user client may control the skin care device based on the control method acquired by the control method acquiring unit.

Additionally, according to the above-described configuration of the present invention, the user client may include a control data storage area of storing the control data for controlling the skin care device and also control the skin care device based on the control data; and the data management server may include a control data updating unit configured to rewrite the control data stored in the control data storage area of the user client based on the control method.

Additionally, according to the management method for skin condition measurement analysis information of the present invention, the user client may execute:

a data browsing requesting step of transmitting the client ID and also requesting transmission of respective data stored correlated to the client ID from the measurement data database or the user data database; and a data displaying step of displaying the transmitted data when the data requested in the data browsing requesting step is transmitted from the data management server, and the data management server may execute a data transmitting step for data browsing of transmitting, to the user client corresponding to the client ID transmitted in the data browsing requesting step, the data registered in the measurement data database or the user data database and also correlated to the client ID transmitted from the user client, based on the request in the data browsing requesting step.

According to the above-described configuration of the present invention, the data management server may extract, in response to a request from the user client, two or more pieces of the measurement data and/or the analysis result data of different acquisition times from the measurement data and/or the analysis result data stored in the measurement data database as the history based on the acquisition times, and transmit the extracted data to the user client, and the user client may execute a comparative displaying step of displaying the measurement data and/or the analysis result data of the different acquisition times in order of acquisition times such that the data can be compared each other.

Additionally, according to the above-described configuration of the present invention, the skin condition measuring device may be provided with a device authentication storage unit configured to store an authentication character string for authenticating the skin condition measuring device and also output the stored authentication character string outside, the user client may executes a device authentication transmitting step of transmitting the authentication character string output from the connected skin condition measuring device to the data management server, and the data management server may include:

an authentication step of authenticating the authentication character string; and a non-authenticated device excluding unit configured to execute control so as not to output the analysis result data of the measurement data transmitted from the user client having the authentication character string that has not been authenticated by the authenticating unit.

Additionally, according to the above-described configuration of the present invention, the skin condition measuring device may be a camera for skin configured to take a close-up photo of skin, and output image data as the measurement data, in the measurement data transmitting step in the user client, the image data output from the skin condition measuring device may be transmitted to the data management server, the image data may be registered in the data analysis database as the measurement data, the data management server may execute:

a calibration step of generating calibration data of calibrating an individual difference of the skin condition measuring device based on the image data photographed by the skin condition measuring device in accordance with a predetermined condition; and a calibration registering step of registering the calibration data generated in the calibration step and the authentication character string in a calibration database, correlated each other, and in the analysis result acquiring step, the calibration data may be acquired from the calibration database based on the authentication character string, and calibration of the image data by the calibration data or calibration of the skin condition measuring device based on the calibration data may be executed.

The management system for skin condition measurement analysis information may include a skin care device that can be controlled from the user client by being connected to the user client, the user client or the data management server may execute:

a skin care data acquiring step of acquiring the analysis result data from the measurement data database based on the client ID output from the user client connected to the skin care device; and a control method acquiring step of acquiring a control method for the skin device from the skin care database in which the control method for the skin care device is registered correlated to the analysis result data, based on the analysis result data acquired in the skin care data acquiring step, and the user client may execute a skin care controlling step of controlling the skin care device based on the control method acquired in the control method acquiring step.

The user client may include a control data storage area of storing control data for controlling the skin care device and also control the skin care device based on the control data, and the data management server may execute a control data updating step of rewriting the control data stored in the control data storage area of the user client based on the control method.

According to the above-described management system for skin condition measurement analysis information and the management method for skin condition measurement analysis information, since the measurement data and the analysis result data are stored in the measurement data database as the history according to the acquisition times of the measurement data and the analysis result data as described above, and the accompanying data is stored together with the data, the user can view the measurement data and the analysis result data as data in chronological order. In this case, when various kinds of skin care are being executed, whether the skin condition is getting better, or does not change, or is deteriorating can be determined to be used for determining whether to continue or change the current skin care.

Additionally, the user can confirm contents of the user data database. Therefore, after confirmation, the user data can also be changed by inputting the user data, using the user data transmitting unit. Additionally, the using cosmetics and the skin care articles as the contents of previous questionnaire may be changed by answering a new questionnaire, for example.

Note that there is no means of transmitting the user data database to the contractor client, what is browsable at the contractor client is the measurement data in the measurement data database and the permitted kind of accompanying data, no data in the user data database is transmitted to the contractor client, and the predetermined personal information is to be protected. Note that, preferably, the date in the user data database is protected by using a known security method.

In skin condition measuring device, the authentication character string is stored in the device authentication storage unit thereof, and in the data management server, the skin condition measuring device can be authenticated using the authentication character string in the case where the authentication character string of the skin condition measuring device is transmitted via a user form client.

For example, in the case where the data management server is operated by a maker or distributor firm of a skin condition measuring device, the operating company can set the data management server such that the analysis result data for the measurement data, namely, the service provided from a data analysis management system, cannot be output from a device other than the skin condition measuring device the operating company manufactures or sells.

In the case where the service of analyzing the measurement data is offered free of charge as described above, a person who try to sell the skin condition measuring device by utilizing this analysis service without permission is likely to appear; however, by executing authentication with the authentication character string as described above, any device other than the skin condition measuring device as a legitimate product capable of analyzing the measurement data in the data management server cannot be used.

Note that the authentication character string is generally called a serial, for example, is a character string having a predetermined number of characters, and among the character strings having the predetermined number of characters, only a character string preliminarily complying with predetermined conditions becomes the authentication character string, and when a character string is set randomly, such a character string has extremely low possibility to be authenticated.

Note that a method of inhibiting output of the analysis result data may be any method as far as the analysis result data is not output, and for example, in the case where authentication is not successful on the occasion where the authentication character string is input from the user form client to the data management server, communication with the user form client may be inhibited, or receipt of the measurement data may be stopped, or acquisition of the analysis result data may be stopped although the measurement data is received, or transmitting the acquired analysis result data may be stopped although the analysis result data for the measurement data is acquired.

Additionally, in the case where the measurement data is image data by the camera for skin, each skin condition measuring device is likely to have different brightness, color tone, etc. depending on individual difference or the like. In this case, an error on the occasion of analyzing the image data is likely to become large. In such a case, the calibration data for correcting and standardizing the individual difference or the like is stored correlated to each authentication character string in the calibration database, and thus the image data can be calibrated and the analysis result data can be obtained from the data analysis database by the calibrated image data when the image data is input to the data management server together with the authentication character string via the user form client. Additionally, when there is an error in brightness, brightness of a light provided in the camera for skin may be calibrated.

Thus, a subtle difference in color tone of skin can be clearly analyzed. Note that the image data photographed in accordance with the predetermined condition is, for example, image data for which the color can be calibrated by pressing a predetermined color pattern (calibration pattern) against the camera for skin at the time of photographing.

The user client can be connected to the skin care device (skin aesthetic device (skin beauty device)) besides the skin condition measuring device, and the connected skin care device can be controlled from the user client, including setting change and the like. For example, in the case where operation can be finished in a preset period after operation start or various kinds of levels such as strength can be set, it is preferable that setting and changing the levels be controllable.

Here, analysis result data correlated to a client ID registered in the measurement data database of the above-described data management server is acquired, and a control method correlated to the analysis result data is acquired from the skin care database. The control method is transmitted to the user client, and an operation time of the skin care device connected to the user client, various kinds of setting levels, and the like can be controlled. In the case where the skin condition is indicated by, for example, step-by-step levels (from bad to good condition) as the analysis result data, control is executed such that in the case where the level is high (skin condition is good), the operation time is made shorter, and in the case where the level is low (skin condition is bad), the operation time is made longer.

By controlling the skin care device in this way, skin care corresponding to the skin condition can be executed. Additionally, efficient use time for the skin care and efficient use of power source such as a battery can be achieved.

Additionally, the skin care device may be optionally controlled by the user operating the user client. For example, the user may set output levels (frequency, voltage, current) of the skin care device. In this case, control data set by the user is stored in a predetermined storage area in the user client. In contrast, more effective setting can be executed by rewriting the control data stored in the storage area on the data management server side. For example, for a person who uses the skin care device with the output lower than suitable output because the person feels pain or the like when the output is high, the data management server rewrites the control data stored in the user client to gradually raise the output, and thus the skin care device can be used at the suitable output while suppressing the occurrence of pain.

In the data management server, use history data is registered correlated to the client ID in the measurement data database.

Therefore, based on the client ID, the use history data, the measurement data, and the analysis result data can be viewed and effect of improving the skin condition by the skin care device can be confirmed.

Additionally, the management system for skin condition measurement analysis information and the management method for skin condition measurement analysis information may be configured as follows.

For example, the management system for skin condition measurement analysis information and the management method for skin condition measurement analysis information may include:

a mobile terminal (user client) capable of connecting the management system for skin condition measurement analysis information to a network via wireless communication; and a data management server connected so as to be able to mutually execute transmission and receipt of information with the mobile terminal via the network, and may include:

a skin condition measuring unit (skin condition measuring device) connected to the mobile terminal or partially provided in the mobile terminal and capable of measuring a skin condition of a user and storing a measurement result in the mobile terminal;

a cosmetic specific information inputting unit provided in the mobile terminal and configured to enable the user to input cosmetic specific information that can specify a cosmetic used by the user;

a skin condition analyzing unit provided in the mobile terminal and/or the data management server, analyzing the measurement result of the skin condition by the skin condition measuring unit based on comparison between the measurement result and accumulated plurality of measurement results of skin condition classified into a plurality of ranks, and determining which one of the plurality of ranks the measured skin condition belongs to as an analysis result;

an analysis result storage unit provided in the data management server and storing along chronological order the ranks determined for each measurement along the chronological order by the skin condition measuring unit;

a using cosmetic specific information storage unit provided in the data management server and storing the cosmetic specific information input by the cosmetic specific information inputting unit, correlated to a use time by the user of the cosmetic;

a history outputting unit provided in the data management server and transmitting, to the mobile terminal, the analysis result stored in the analysis result storage unit and the cosmetic specific information stored in the using cosmetic specific information storage unit in response to a request from the mobile terminal based on the user operation; and a history display unit provided in the mobile terminal and displaying the analysis result transmitted by the history outputting unit correlated to the chronological order and also displaying the cosmetic specific information that can specify the use time correlated to the chronological order.

According to the above-described configuration, the user can find out change in the analysis results for the measurement result of the skin condition with passage of a period and the cosmetic used during the period by regularly executing measurement of the skin condition and also by inputting information based on which a use period of a used cosmetic or a use period can be calculated and thus the user can easily determine the presence or absence of the effect of the cosmetic (mainly a cosmetic for skin care). As a result, the user is highly likely to measure the skin condition and input the using cosmetic actively, and data of the skin condition of the user and data of the used cosmetic is to be accumulated in the data management server.

The data can be, for example, effectively utilized for cosmetic development, and particularly as the number of persons who measure the skin condition increases, added value is likely to become high. Additionally, the user who frequently measures the skin condition and inputs the cosmetic may, for example, look at the screen display of the mobile terminal more often, and in the case of displaying advertisement on the screen of the mobile terminal, an advertisement effect becomes high. Additionally, a relation between the skin condition and the using cosmetic can be easily found out as described above, and therefore, for example, when the skin condition is not so good, a propaganda effect of the cosmetic products increases.

Here, the ranks of skin condition is ranks obtained by ranking the skin condition from bad condition to good condition based on the measurement results of the skin condition already accumulated, and for example, good or bad skin condition may be converted into a numerical value and expressed in a score from zero to a predetermined value. Further, the skin condition may be indicated by age correlated to average skin condition in each age (generation) from the accumulated measurement results. After converting the skin condition of the user who executes frequent measurement into a numerical value as the score or the like, the skin condition may be expressed by, for example, a deviation value as a result of statistical processing.

According to the above-described configuration, the data management server may include a registered cosmetic storage unit in which cosmetic information of each of the cosmetics including the cosmetic specific information that can specify each of the cosmetics is registered, correlated to one another for each of the cosmetics and from which, in the case where the cosmetic information is received from the mobile terminal, the cosmetic specific information related to or identical to the received cosmetic information can be extracted, and the cosmetic specific information inputting unit may include an input assisting unit that assists a user to be able to input the cosmetic information including the cosmetic specific information before the user determinately inputs the cosmetic specific information; the input cosmetic information to be transmitted to the data management server when the cosmetic information is input; and the user to determinately input the cosmetic specific information by displaying the transmitted cosmetic specific information selectable by the user in the case where the cosmetic specific information related to or identical to the transmitted cosmetic information is extracted from the registered cosmetic storage unit and transmitted to the mobile terminal.

According to the above-described configuration, data input is simplified on the occasion of inputting data of the using cosmetic. That is, since the cosmetic data is already registered, it becomes possible to easily extract and input the using cosmetic by a key word or the like. Additionally, confirmation is possible. For example, in the case where a cosmetic is registered by inputting a bar code, a correct product name may be unknown, but the product name of the cosmetic can be found out by retrieving the data registered using the bar code. Additionally, when the cosmetic is not at hand, it also becomes possible to input the using cosmetic not clearly remembered.

Additionally, according to the above-described configuration, the mobile terminal or the data management server may include a non-registration determining unit configured to determine that the cosmetic specific information of the cosmetic corresponding to the cosmetic information is not registered in the registered cosmetic storage unit in the case where the cosmetic specific information related to or identical to the cosmetic information cannot be extracted from the registered cosmetic storage unit on the occasion where the cosmetic information is transmitted from the mobile terminal to the data management server, the mobile terminal may include a non-registered cosmetic specific information inputting unit configured to enable the user to input the non-registered cosmetic specific information in the case where the cosmetic is determined to be non-registered by the non-registration determining unit, and also transmit the cosmetic specific information to the data management server when the cosmetic specific information is input, and the data management server may include;

a cosmetic maker contact information storage unit in which the cosmetic specific information and cosmetic maker contact information specified by the cosmetic specific information are correlated;

a temporary registration unit configured to temporarily register the transmitted cosmetic specific information in the registered cosmetic storage unit in the case where the cosmetic specific information is transmitted from the non-registered cosmetic specific information inputting unit;

a communication assisting unit configured to extract the contact information from the cosmetic maker contact information storage unit based on the cosmetic specific information temporarily registered in the temporary registration unit, and assist a contact with the contact information to request for proper registration in the registered cosmetic storage unit of the temporarily-registered cosmetic information of the cosmetic correlated to the cosmetic specific information temporarily registered in the temporary registration unit, and a registration permitting unit configured to permit a contacted person in charge of the cosmetic maker to register the cosmetic information in the registered cosmetic storage unit.

According to the above-described configuration, as for a cosmetic not registered, the user is to find out that the cosmetic is a non-registered cosmetic by attempting to input data of the non-registered cosmetic. On this occasion, the cosmetic is to be temporarily registered by inputting a product name or a product code (JAN code) that can specify the cosmetic in the case where the cosmetic to be registered is not registered. That is, it becomes possible to have the user find the non-registered cosmetic and also temporarily register the non-registered cosmetic.

In this state, for example, in the case where the maker contact information is known based on the information that can specify the above-described cosmetic, a request can be made to the maker contact information to input various kinds of information of the cosmetic temporarily registered in the data management server. Therefore, an administrator or an operator of the data management server can have the user and the person in charge of the maker execute processing of investigating a newly released cosmetic and registering the information of the cosmetic in the data management server. Thus, management work for the data management server can be reduced and management cost can be reduced.

Additionally, according to the above-described configuration, the history display unit may display the analysis result transmitted by the history outputting unit as a graph including a time axis indicating time passage in conformity with the chronological order and a rank axis indicating a rank as the analysis result, and also display the use time of the cosmetic specific information transmitted by the history outputting unit in conformity with the time axis of the graph.

According to the above-described configuration, a relation between the change in the rank of the skin condition with time passage and the using cosmetic can be easily grasped, and whether the using cosmetic suites the skin can be easily determined.

Additionally, in the above-described configuration, a simultaneous comparison unit may be provided, where the latest rank among the ranks as the analysis result stored along the chronological order in the analysis result storage unit and a rank on a date in the past input based on the user's operation from the mobile terminal are simultaneously comparably displayed.

According to this configuration, for example, the latest skin condition and a relatively old skin condition obtained a certain time ago can be easily compared, and therefore a difference of skin condition over a long period can easily be grasped. Additionally, in the case where there is a time when the skin condition was deteriorated previously, the skin condition at the time when the skin condition was deteriorated and the current skin condition can be easily compared, and the extent of recovery of the skin condition can easily be found out.

Additionally, according to the above-described configuration, the skin condition analyzing unit may analyze the measurement result of the skin condition by the skin condition measuring unit based on comparison between the measurement result and an accumulated plurality of measurement results of the skin condition classified into a plurality of types, and determine which skin type among the plurality of skin types the skin condition measured as the analysis result belongs to, in the analysis result storage unit, the ranks and the skin types of a plurality of users as the analysis results may be stored for each of the users, in the using cosmetic specific information storage unit, the cosmetic specific information of the cosmetic used by each of the plurality of users may be stored for each of the users, the data management server may include:

a user extracting unit in which in the case where a request is made to display analysis results of other users who use the cosmetic specified by the cosmetic specific information specified by the user operation from the mobile terminal and the cosmetic specific information and also who have the same skin type as the user having specified the cosmetic, other users having the specified cosmetic specific information registered in the using cosmetic specific information storage unit are extracted, and other users having the same skin type as the user having specified the cosmetic are extracted from the analysis result storage unit, to output a redundant user narrowed down by being redundantly extracted from both the using cosmetic specific information storage unit and the analysis result storage unit;

a rank extracting unit configured to extract, from the analysis result storage unit, the rank of the redundant user extracted from the user extracting unit; and a rank transmitting unit configured to create a data table in which the rank of each of other users extracted from the rank extracting unit is correlated to a transitional period from start of using the cosmetic specified by each of other users, and transmits the data table to the mobile terminal, and the mobile terminal may include an analysis result display unit for other user configured to display the rank on the transmitted data table correlated to the transitional period from start of using the specified cosmetic.

According to this configuration, it is possible to find out the skin condition change in the case where other person having the same skin type as the user uses the cosmetic used by the user and the cosmetic which the user is thinking about using. The skin condition change of the other person having the same skin type enables the user to predict whether the cosmetic is suitable for the user, and serves as a reference in the case of determining the cosmetic to be used from among many cosmetics.

In the management method for skin condition measurement analysis information that includes:

a mobile terminal capable of connecting the management method for skin condition measurement analysis information to a network via wireless communication;

a data management server connected so as to be able to mutually execute transmission and receipt of information with the mobile terminal via the network; and a skin condition measuring unit connected to the mobile terminal or at least partially provided in the mobile terminal, and capable of measuring the skin condition of the user and storing the measurement data in the mobile terminal, the mobile terminal may be configured to enable the user to input cosmetic specific information that can specify a cosmetic used by the user, the mobile terminal and/or the data management server may analyze the measurement result of the skin condition by the skin condition measuring unit based on comparison between the measurement result and accumulated plurality of measurement results of skin condition classified into a plurality of ranks, and determine which one of the plurality of ranks the measured skin condition belongs to as an analysis result, and the data management server may be configured to:

store along chronological order the ranks determined for each measurement along the chronological order by skin condition measuring unit;

store the cosmetic specific information input by the user, correlated to a use time by the user of the cosmetic; and transmit, in response to a request from the mobile terminal based on the user operation, the analysis result stored in the data management server and the cosmetic specific information to the mobile terminal, and the mobile terminal may display the analysis result transmitted from the data management server correlated to the chronological order, and also display the cosmetic specific information which can specify the use time correlated to the chronological order.

According to the above-described configuration, the data management server may include a registered cosmetic storage unit in which the cosmetic information of each of the cosmetics including the cosmetic specific information that can specify each of the cosmetics is registered correlated to one another for each of the cosmetics, and from which, in the case where the cosmetic information is received from the mobile terminal, the cosmetic specific information related to or identical to the received cosmetic information can be extracted, and the mobile terminal may be configured to:

enable a user to input the cosmetic information including the cosmetic specific information in the mobile phone before the user determinately inputs the cosmetic specific information; transmit the input cosmetic information to the data management server in the case where the cosmetic information is input by the user; and assist the user to determinately input the cosmetic specific information by displaying the transmitted cosmetic specific information such that the user can select and determinately input the cosmetic specific information in the case where the cosmetic specific information related to or identical to the transmitted cosmetic information is extracted from the registered cosmetic storage unit and transmitted to the mobile terminal.

Additionally, according the configuration of the present invention, the mobile terminal or the data management server may determine that the cosmetic specific information of the cosmetic corresponding to the cosmetic information is not registered in the registered cosmetic storage unit in the case where the cosmetic specific information related to or identical to the cosmetic information cannot be extracted from the registered cosmetic storage unit on the occasion where the cosmetic information is transmitted from the mobile terminal to the data management server, the mobile terminal may enable the user to input the non-registered cosmetic specific information in the case where the cosmetic is determined to be non-registered, and also transmit the cosmetic specific information to the data management server when the cosmetic specific information is input, the data management server may be configured to:

include a cosmetic maker contact information storage unit in which the cosmetic specific information and cosmetic maker contact information specified by the cosmetic specific information are correlated;

temporarily register the transmitted cosmetic specific information in the registered cosmetic storage unit in the case where the cosmetic specific information is transmitted from the mobile terminal;

extract the contact information from the cosmetic maker contact information storage unit based on the cosmetic specific information temporarily registered in the temporary registration unit, and assist a contact with the contact information to make a request to properly register, in the registered cosmetic storage unit, the temporarily-registered cosmetic information of the cosmetic correlated to the cosmetic specific information temporarily registered in the registered cosmetic storage unit; and permit a contacted person in charge of the cosmetic maker to register the cosmetic information in the registered cosmetic storage unit.

Additionally, according to the above-described configuration, the mobile terminal may display the analysis result transmitted from the data management server as a graph including a time axis indicating time passage in conformity with the chronological order and a rank axis indicating a rank as the analysis result, and also display the use time of the cosmetic specific information transmitted from the data management server in conformity with the time axis of the graph.

Additionally, according to the above-described configuration, the latest rank among the ranks as the analysis result stored along the chronological order in the data management server and a rank on a date in the past input based on the user's operation from the mobile terminal may be simultaneously comparably displayed.

Additionally, according to the above-described configuration, the data management server may analyze the measurement result of the skin condition measured by the skin condition measuring unit based on the comparison between the measurement data and an accumulated plurality of measurement results of the skin condition classified into a plurality of types, and determine which skin type among the plurality of skin types the skin condition measured as the analysis result belongs to, in the data management server, the ranks and the skin types of a plurality of users as the analysis result may be stored for each of the users, and also the cosmetic specific information of the cosmetic used by each of the plurality of users may be stored for each of the users, and in the case where a request is made to display analysis results of other users who use the cosmetic specified by the cosmetic specific information specified by the user operation from the mobile terminal and the cosmetic specific information and also who have the same skin type as the user having specified the cosmetic specific information, the data management server may:

extract other users having the specified cosmetic specific information registered and extracts other users having the same skin type as the user having specified the cosmetic to output a redundant user narrowed down by being redundantly extracted from both the specified cosmetic specific information and the skin type, include a rank extracting unit configured to extract, from the data management server, the rank of the redundant user; and create a data table in which the rank of each of other users extracted from the rank extracting unit is correlated to a transitional period from start of using the cosmetic specified by each of other users and transmit the data table to the mobile terminal, and the mobile terminal may display the rank on the transmitted data table correlated to the transitional period from start of using the specified cosmetic.

According to the above-described management method for skin condition measurement analysis information, the effects same as those of the corresponding management system for skin condition measurement analysis information can be obtained.

Further, according to the above-described respective management system for skin condition measurement analysis information and management method for skin condition measurement analysis information, the skin condition measuring device (skin condition measuring unit) may include authentication information that can be transmitted to the data management server via a user client and can individually authenticate each of the skin condition measuring devices, the data management server may include:

an authenticating unit configured to authenticate the authentication information;

an authentication information management table in which the authentication information authenticated by the authenticating unit of the skin condition measuring device and the client ID input from the user-client (mobile terminal) having transmitted the authentication information are registered correlated each other, and further a predetermined number of the client IDs can be registered for respective authentication information, a registering unit configured to refer to the authentication information management table based on the authentication information transmitted via the user client at the time of using the skin condition measuring device and also authenticated by the authenticating unit and the client ID input from the user client, and register the client ID correlated to the authentication information in the authentication information management table when the number of other client IDs already registered correlated to the authentication information is fewer than the predetermined number in the case where the client ID is not registered correlated to the authentication information in the authentication information management data; and a use inhibiting unit configured to inhibit use of the skin condition measuring device via the user client in the cases where: the authentication information is not input in the data management server; the authentication information is not authenticated by the authenticating unit; and the client ID is not registered correlated to the authentication information in the authentication information management table and also the number of the client IDs already registered correlated to the authentication information in the authentication information management table is the predetermined number.

According to the above-described configuration, in the case where the authentication information input to the data management server from the skin condition measuring device via the user client is not authenticated by the authenticating unit, use of the skin condition measuring device is inhibited via the user client. For example, even when the measurement data is output from the skin condition measuring device, the analysis result data is not output to the user client from the data management server and the skin condition measuring device enters an unusable state.

In the same manner, in the case where the authentication information is not input from the skin condition measuring device to the data management server via the user client, the skin condition measuring device enters the unusable state.

Additionally, in the same manner, in the case where the predetermined number of other client IDs is already registered correlated to the authentication information in the authentication information management table although the authentication information is authenticated, the skin condition measuring device enters the unusable state. In this case, the skin condition measuring device becomes usable in the user client having the client ID already registered correlated to the authentication information in the authentication information management table.

According to the above-described management system for skin condition measurement analysis information and management method for skin condition measurement analysis information, any illegitimate skin condition measuring device other than a legitimate skin condition measuring device used in the management system for skin condition measurement analysis information is not authenticated, and damage caused by using such an illegitimate skin condition measuring device with respect to the management system for skin condition measurement analysis information can be suppressed.

Additionally, since in authentication information management table, the predetermined number of client IDs can be registered correlated to one piece of the authentication information, and the skin condition measuring device can be used via the user clients of the registered client IDs, for example, in the case where the predetermined number is members of a group like a family, the same skin condition measuring device can be used by connecting to the user clients of the respective members.

In other words, even when the skin condition measuring device is a legitimate device having the authentication information that can be authenticated by the authenticating unit, use at the user client having a different client ID is limited, and for example, even in the case of the legitimate product, the skin condition measuring device cannot be used by being connected to the number of the user clients exceeding the predetermined number. Therefore, using the skin condition measuring device among a relatively small group such as a family is permitted but unruly using is restricted, and thus both user friendliness and appropriate operating cost for the management system for skin condition measurement analysis information can be satisfied in a good balance. Note that the above-described exclusion of the illegitimate product by using the authentication information and limiting use in the plurality of user clients may be applied not only to the skin condition measuring device but also to the skin care device that can be used by connecting to the user client.

Advantageous Effects Of Invention

According to the management system for skin condition measurement analysis information and the management method for skin condition measurement analysis information of the present invention, the contractor such as the cosmetic company can acquire the measurement data of the skin condition and the analysis result data of analyzing the measurement data of many users, and the accompanying data of a user, and the user can have the skin condition analyzed free of charge or at a low price due to usage fee of the contractor.

Additionally, the effects of the currently using cosmetics can be estimated because the skin condition change with time passage and the cosmetic used for the period can be confirmed by comparison.

BRIEF DESCRIPTION OF DRAWINGS

FIG. 1 is a schematic block diagram illustrating a management system for skin condition measurement analysis information according to an embodiment of the present invention.

FIG. 2 is a diagram illustrating display screens and the like of a smartphone that has started an application for a management system for skin condition measurement analysis information.

FIG. 3 is a diagram for describing functions of the smartphone application.

FIG. 4 is a diagram for describing beauty devices registered in the smartphone.

FIG. 5 is a block diagram illustrating the management system for skin condition measurement analysis information.

FIG. 6 is a flowchart illustrating a user registration processing in a management method for skin condition measurement analysis information according to the embodiment of the present invention.

FIG. 7 is a flowchart illustrating sensor registration processing in the management method for skin condition measurement analysis information.

FIG. 8 is a flowchart illustrating skin analysis processing in the management method for skin condition measurement analysis information.

FIG. 9 is a flowchart illustrating display processing for a detailed skin analysis result in the management method for skin condition measurement analysis information.

FIG. 10 is a flowchart illustrating beauty care processing in the management method for skin condition measurement analysis information.

FIG. 11 is a flowchart illustrating skin condition improvement determination processing in the management method for skin condition measurement analysis information.

FIG. 12 is a flowchart illustrating skin history display processing in the management method for skin condition measurement analysis information.

FIG. 13 is a flowchart illustrating skin history display processing in the management method for skin condition measurement analysis information.

FIG. 14 is a flowchart illustrating secondary use processing in the management method for skin condition measurement analysis information.

FIG. 15 is a flowchart illustrating a modified example of the secondary use processing in the management method for skin condition measurement analysis information.

FIG. 16 is a flowchart illustrating user cosmetic registration processing in the management system for skin condition measurement analysis information.

FIG. 17 is a flowchart illustrating user skin history display processing in a management system for skin condition measurement analysis information.

FIG. 18 is a flowchart illustrating effect confirming processing for a specified cosmetic in the management system for skin condition measurement analysis information.

FIG. 19 is a diagram for describing a cosmetic registration screen displayed on a smartphone display.

FIG. 20 is a diagram for describing an input screen for using cosmetics for a care chart displayed on the smartphone display.

FIG. 21 is a diagram for describing a skin history display screen displayed on the smartphone display.

FIG. 22 is a diagram for describing a comparison display screen displayed on the smartphone display.

FIG. 23 is a diagram for describing a cosmetic selecting screen and a graph display screen displayed on the smartphone display.

FIG. 24 is a diagram for describing search items displayed on a display screen of a contractor client and classified into search levels.

FIG. 25 is a diagram for describing the search items displayed on the display screen of the contractor client and classified into the levels by the search levels.

FIG. 26 is a diagram for describing kinds of data displayed on the display screen of the contractor client and classified into levels by access levels.

FIG. 27 is a diagram for describing the kinds of data displayed on the display screen of the contractor client and classified into the levels by the access levels.

FIG. 28 is a diagram illustrating a history deleting button displayed on an analysis result display screen of the smartphone.

FIG. 29 is a diagram illustrating the history deleting button displayed on a past analysis result display screen of the smartphone.

FIG. 30 is a block diagram illustrating the management system for skin condition measurement analysis information provided with an image quality converting unit for unifying the number of pixels in image data sent from the smartphone to a data management server.

FIG. 31 is a block diagram illustrating the management system for skin condition measurement analysis information provided with the image quality converting unit for unifying the number of pixels in the image data sent from the smartphone to the data management server.

FIG. 32 illustrates Table 2.
FIG. 33 illustrates Table 3.
FIG. 34 illustrates Table 4.
FIG. 35 illustrates Table 5.
FIG. 36 illustrates Table 7.
FIG. 37 illustrates Table 10.
FIG. 38 illustrates Table 11.
FIG. 39 illustrates Table 15.
FIG. 40 illustrates Table 17.

DESCRIPTION OF EMBODIMENT

An embodiment of the present invention will be described with reference to the drawings.

A system for skin condition measurement analysis information and a management method for skin condition measurement analysis information according to the present embodiment is directed to offering, to a user of a skin condition measuring device who is a member of the management system of skin condition measurement analysis information, service whereby an analysis result on the own skin condition of the user can be obtained from measurement data of the skin condition measuring device, at low cost (e.g., free-of-charge or relatively inexpensive membership fee) and thus having the user recognize the own skin condition.

On this occasion, the number of sales of the skin condition measuring device can be increased by enabling the skin condition to be found out at the low cost, and also as the user is encouraged to frequently measure the skin condition to obtain the analysis result from the measurement data, the measurement data from many users can be collected. In this case, sales of skin care articles and a skin care device 2 is promoted by making the users use the skin care articles including cosmetics and the skin care device 2 to grasp improvement of the skin condition. Note that, to encourage the users to measure the skin condition, points may be given to the users on the occasion where the users measure the skin condition and request for analysis.

Additionally, in the case of having collected many pieces of measurement data of skin condition, the collected data can be used for development of various kinds of skin care articles by makers and distributor firms of cosmetics (cosmetics companies) for a fee. On this occasion, the measurement data can be used more effectively by providing not only the measurement data but also accompanying data including the skin care articles and skin care device 2 used by the user and further a rough age, a place of residence, annual income, occupation, etc. of the user, and thus adding an additional value to the measurement data. Thus, profit can be obtained not only from the users who purchase the skin condition measuring device and the like but also from a secondary user of the data, such as the cosmetic company, that uses the above-described measurement data.

As illustrated in FIG. 1, the management system for skin condition measurement analysis information according to the present embodiment includes a skin condition measuring device 1, a smartphone 3 as a user client connectable to a skin care device (beauty care device) 2, a data management server 5 connectable to the smartphone 3 via the Internet 4 (network), and a computer system of a partner company such as a cosmetic company as a contractor client 6.

The skin condition measuring device 1 is, for example, a camera for skin and includes a sensor unit 11 provided with an imaging device and a lighting LED, a control unit 12, and a USB (universal serial bus) interface 13.

The lighting LED is capable of emitting two colors of light and alternately emitting skin color light and white color light. When the skin color light is emitted, the skin condition can be clearly photographed and condition of skin texture (texture) can be analyzed. Generally, when the condition of the skin texture is good, substantially triangle-shaped mesh-like grooves can be observed on a skin surface relatively in a logical manner. In contrast, when the condition of the texture is bad, the grooves become unclear, a shape of the mesh is collapsed, or the grooves become less visible, and a portion having no groove is in a roughened state.

Additionally, the above-described groove is called sulci cutis and a flat portion on the substantially triangle shape surrounded by the sulci cutis is called cristae cutis. Additionally, pores are observed in addition to the sulci cutis and cristae cutis, but in the case where the condition of the texture is good, the pores are small and less visible while in the case where the condition is bad, the pores become large and clearly visible.

When the skin is magnified and photographed under the skin color light, the condition of the texture turns out to be a clear image and the image data can be easily analyzed.

Additionally, in the case of lighting the skin with the white light, image data where spots are easily recognized can be obtained.

That is. The spots appear dark (gray) in contrast to the skin that appears white, and the spots can be relatively easily recognized. The skin condition measuring device 1 as the camera for skin can execute photographing by switching between a texture mode and a spots mode and provided with a mode change switch for changing the modes. In connection with imaging data as the measurement data by the camera for skin, data indicating the texture mode or the spots mode is output to the smartphone 3.

Note that, in addition to the above-described white color light and skin color light, the skin may be irradiated with, for example, light having a wavelength of about 375 mm that is near-ultraviolet light as a lighting so as to detect porphyrin inside the skin. Note that, at the time of irradiating the skin with ultraviolet light, the porphyrin can be detected by red-orange fluorescence emitted from the porphyrin excited by the ultraviolet light. Note that the porphyrin may exist in the skin of a porphyria patient.

Note that a photographing portion of the camera for skin includes a box-shaped hood and is provided with a transparent plate (may have an optical function) deep inside the hood, and a lens, the imaging device, the lighting LED, etc. are provided on the back side (inner side) of the transparent plate. Photographing can be executed when a tip of the hood is pressed against the skin to shield a surrounding light.

A USB interface 13 is used for, for example, connecting with the above-described smartphone 3 (an intelligent device including a processor (CPU) capable of executing arithmetic processing based on a program) as the user client, and the USB interface is also provided on the smartphone 3 side. The USB interface 13 of the skin condition measuring device 1 is a client side and the USB interface of the smartphone 3 as the user client becomes a host side.

The skin condition measuring device 1 is capable of outputting the image data as the measurement data by the USB interface 13, and for example, adjustment of brightness of the lighting LED can be controlled from the smartphone 3 side.

Additionally, the USB interface 13 is provided with a buffer for data storage called an end point, and data stored in the end point is read from the smartphone 3 side.

Further, in the USB interface, data called a descriptor is written and configured to be read from the smartphone 3 side. For example, in the case where the skin condition measuring device 1 outputs the image data same as the above-described camera for skin, for example, the fact of being the camera (a device that outputs images) is written in the descriptor, and a driver for the camera preliminarily stored or a driver installed as a part of a dedicated application 5j described later is set on the smartphone 3 side.

Note that the descriptor includes a device descriptor in which a USB Revision, a device class, a vendor ID, etc. are registered, a configuration descriptor in which a kind of a power source, maximum power consumption, etc. are registered, an interface descriptor in which a class code, the above-described endpoint, etc. are registered, an end point descriptor in which a data transmitting direction from the end point, and a transmitting method, a maximum bucket size, etc. are registered, in connection with a device such as the above-described camera.

Additionally, the descriptor includes a string descriptor that stores a character string, and according to the present embodiment, a product serial number is stored in this descriptor for the character string as an authentication character string. Using this product serial number, the skin condition measuring device 1 can be authenticated as a specified device, for example, a device manufactured by a predetermined maker.

That is, the skin condition measuring device 1 stores the authentication character string and also has a function as a device authentication transmitting unit that executes outputting to the smartphone 3 that is the user client (mobile terminal)

That is, even in the case of the skin condition measuring device 1 having the same function, for example, only the skin condition measuring device 1 authorized by an operating company of the data management server 5 can be recognized using the product serial number so as to be used in the management system for skin condition measurement analysis information. That is, in the case where the product serial number cannot be read from the skin condition measuring device 1, or in the case where the product serial number is not a product serial number arranged in a predetermined character string and cannot be authenticated, use of the management system for skin condition measurement analysis information is inhibited.

Note that the data communication between the camera for skin as the skin condition measuring device 1 and the smartphone 3 is not limited to the USB, and other serial or parallel wired communication and wireless communication such as Bluetooth, WiFi, NFC (Near Field Communication), etc. may also be used.

Additionally, the camera for skin may be a digital camera built inside the smartphone or the like and having a conversion lens attached thereto. Thus, the image data photographed by the digital camera of the smartphone and stored in a storage device of the smartphone 3 can be transmitted to the data management server 5 via the Internet 4. In this case, it is not necessary to transmit the image data from the camera for skin to the smartphone as in the case of connecting the camera for skin to the smartphone 3, and a communication unit for transmitting the image data is unnecessary.

However, also in the conversion lens, it is preferable not to use outside light but to photograph by using the above-described skin color light LED and white color light LED. In this case, it is necessary to synchronize photographing timing (shutter releasing timing) on the smartphone side, emitting timing of a white color light LED on the conversion lens side, and emitting timing of a skin color light LED on the conversion lens side. That is, photographing by the smartphone 3 while the white color light on the conversion lens side is emitted and photographing by the smartphone 3 while the skin color light on the conversion lens side is emitted are needed to be executed.

In such a case, the above-described wired communication such as the USB or Bluetooth, WiFi, NFC, etc. may be used. Additionally, photographing is basically executed in the smartphone 3 based on a photographing program of the later-described dedicated application 5*j*, and when the lighting at the time of photographing is necessary, the smartphone 3 only needs to switch on/off the white color light LED (driving circuit) and the skin color light LED (driving circuit) of the conversion lens.

Accordingly, a light receiver may be disposed on the conversion side such that the above-described ON/OFF of the LED is controlled based on whether the above-described light receiver has received the light emitted from the Lighting LED (flash) at the time when the smartphone 3 executes photographing. The above-described ON/OFF of the LED may also be controlled by an output sound on the smartphone side such as a shutter sound. On this occasion, a signal may be transmitted using DTMF (Dual Tone Multi Frequency) for the control by the sound.

Additionally, lighting ON/OFF of a white color LED and lighting ON/OFF of a skin color LED may be executed based on a predetermined time interval on the conversion lens side and the lighting ON/OFF may be detected on the digital camera side of the smartphone 3, based on which texture-mode photographing in the case of emitting the skin color light LED and spots-mode photographing in the case of emitting the white color light LED may be executed.

Additionally, such a configuration may be adopted where an ID (serial number) used for discriminating whether a conversion lens is a legitimate product or an illegitimate product (imitation) or discriminating difference in an utilization condition of each conversion lens and the like is transmitted from the conversion lens to the data management server 5 side via the smartphone 3. In this case, the ID may be transmitted from the conversion lens side to the smartphone 3 side by using the above-described USB, Bluetooth, WiFi. NFC, and so on. Additionally, in the case of not providing the above-described communication units on the conversion lens side, for example, a bar code such as a two-dimensional bar code, other code, or a character string indicated on attached items such as a box, a manual, a guarantee form attached to the conversion lens at the time of purchasing the conversion lens may be photographed by the smartphone 3, and a photographed image or an ID converted from the bar code or the like by image recognition of the image, or an ID recognized as a character may be transmitted to the data management server 5 side. Additionally, the above-described bar code or character string may be disposed at a position imaged within a range of a photographed image when photographing is executed by the smartphone 3 of the conversion lens, and an ID of the conversion lens may be read from the bar code or the like imaged within the range of skin image data on the data management server 5 side by sending the photographed skin image data to the data management server 5.

Additionally, there is possibility in the future that the camera of the smartphone be provided with a macro function and become capable of taking a close-up photo of the skin, or mounted with a digital camera provided not simply with the macro function but with an optical system capable of photographing the above-described texture and spots as the camera for skin, and in such a case, the skin may be photographed by the digital camera mounted to the smartphone without conversion lens and image data thereof may be sent to the data management server 5.

Additionally, the skin condition measuring device 1 may be, other than the above-described camera for skin, a known evaporimeter that measures transepidermal water loss, or a melanin meter that measures a melanin amount in the skin may be adopted besides.

Additionally, a device that measures ultraviolet (UV) (UV checker) may be connectable to the smartphone 3 as an environment measurement sensor although not being a device that directly measures the skin condition. Note that in the case of observe influence of the ultraviolet to the skin, it is preferable that the UV checker be capable of consecutively outputting separate independent value data for UV-A related to melanin generation and UV-B causing inflammation, respectively.

The above-described skin condition measuring device 1 can output the above-described product serial number and measurement data to the smartphone 3 via the USB interface 13.

Additionally, with authentication of the product serial number, the analysis result data on the measurement data output via the smartphone 3 can be obtained. Note that in the case of the conversion lens, preferably the product serial number of the conversion lens can be made to the smartphone 3 via the above-described wired or wireless communication. Additionally, in the case where there is no communication executed between the smartphone 3 and the conversion lens side, a coat which can be optically recognized and indicates the product serial number, such as the two-dimensional bar code, is disposed outside a photographing range of the skin within the photographing range of the digital camera of the smartphone 3 of the conversion lens, and thereby the product serial number can be transmitted from the conversion lens to the smartphone. In this case, a program capable of reading the two-dimensional bar code needs to be installed on the smartphone side as a part of the later-described dedicated application 5*j*. Thus, it becomes possible to sort out a user of a specific conversion lens and a specific camera for skin and other users, and further exclude an imitation conversion lens and an illegitimate conversion lens, or exclude an inappropriate photographed image.

Additionally, in the camera for skin as the skin condition measuring device 1, for example, photographing is executed under predetermined conditions, and when the image data and the product serial number obtained on that occasion are sent to the data management server 5 via the smartphone 3, brightness and color tone can be calibrated. Note that photographing under the predetermined conditions is, for example, photographing while the hood of the camera for skin is pressed against black and white patterns or color patterns.

The image data may be corrected with calibration data obtained by calibration or, for example, the lighting LED may be adjusted by light control data and color control data based on the calibration data on the camera for skin side. Note that, although it has been described that the skin condition measuring device 1 is connected to smartphone 3 via the USB interface 13, the skin condition measuring device 1 may be connected to the smartphone 3 by using Bluetooth (registered trademark).

For the skin care device 2, for example, an ion cleansing device that removes dirt of the skin with positive ions, an ion introducing device that causes an ionized component to permeate deep skin by passing a feeble DC current to the skin, an LED photo beauty device that provides activation of skin cells and hyperthermic effect by applying the LED light, a roller beauty device that stimulates the skin with the roller having germanium and the like attached thereto and provides effect of massage, a cooling beauty device that cools the skin to close the pores, and an ultrasonic wave beauty device that provides the effect of massage and the hyperthermic effect are prepared.

Additionally, the skin care device 2 includes an actuating unit 21 actually acting on the skin and also includes the control unit 12 and the USB interface 13 in the same manner as the skin condition measuring device 1. Additionally, an operation time, an output level and the like of the skin care device 2 can be controlled by the smartphone 3 by connecting the skin care device 2 to the smartphone 3 via the USB interface 13, and operation can be stopped when a time preset on the smartphone 3 side has passed after a user starts the skin care device 2. Additionally, in the case of the skin care device 2 having a plurality of steps of the output level, the output level can be set from the smartphone 3 side.

For example, the data management server 5 later described is provided with a skin care database 5*l* in which the above-described analysis result data is correlated to a control method such as the operation time and output level of the skin care device 2, and for example the skin care device 2 can be controlled by acquiring the analysis result data from a measurement data database 52 and acquiring the control method corresponding to the acquired analysis result data from the skin care database 5*l*. That is, the skin care device 2 can be efficiently actuated based on the analysis result on the measurement data.

Note that a product serial number as an authentication character string is also stored in the skin care device 2 and can be output, in the same manner as the skin condition measuring device 1.

The user client is basically the smartphone 3, but may be a device provided with a general-purpose arithmetic processing unit (such as CPU) that executes processing based on a program of a notebook computer, a tablet type (pad type) computer, or the like. For the user client, it is preferable to adopt a portable device that can be connected to the Internet 4 as a network via the wireless telephone line or other wireless communication line.

The smartphone 3 as the user client is capable of using, for example, a wireless telephone line for mobile use as the wireless communication, and also capable of using the wireless LAN (WiFi), and is connectable to the Internet 4 as the network by using the wireless communication so as to be a wireless mobile terminal (wireless mobile client).

Additionally, in the smartphone 3, for example, an application downloaded and installed (hereinafter simply referred to as the dedicated application 5*j*) is executable, and according to the present embodiment, an application for measuring the skin condition is downloaded from the data management server 5 to the smartphone 3 as the dedicated application 5*j*.

The dedicated application 5*j* executed in the smartphone 3 includes four functions as illustrated in FIGS. 2 and 3. That is, there are four functions including beauty analysis, beauty care, beauty life, and beauty makeup. In the beauty analysis, various kinds of measurement illustrated in FIG. 3 can be executed by using various kinds of measurement devices (sensors) connected to the smartphone 3 via the USB interface 13. Each of the measurement devices is usable by connecting to a USB terminal of the smartphone 3 in which the dedicated application 5*j* installed. Additionally, measurement by a different sensor can be executed by newly connecting to each kind of measurement device, and mainly the skin condition can be measured.

Additionally, measurement results of the various kinds of measurement devices can be transmitted to and stored in the data management server 5, and also the skin condition can be analyzed from the measurement data.

In the beauty care, various kinds of the skin care devices can be used by connecting to the smartphone 3. In this case also, the various kinds of skin care devices can be attached to the USB terminal in the same manner as the above-described beauty analysis. Additionally, a use history can be saved by connecting to the smartphone 3, and the various kinds of skin care devices can be controlled by enabling data communication between the smartphone 3 and the data management server 5.

The beauty life is directed to daily life while the beauty analysis is mainly directed to the skin and a device for checking an amount of ultraviolet light or breath odor can be connected to the USB terminal of the smartphone 3. In the beauty makeup, information related to makeup is mainly provided.

FIG. 2 is a diagram illustrating display screens 3*a*, 3*b*, 3*c* and 3*d* as a display unit of the smartphone 3. The display screen 3*a* indicates a main menu, the display screen 3*b* indicates a beauty analysis menu, and the display screen 3*c* indicates registered sensor display. Note that marks of devices that can be registered preliminarily are displayed on the registered sensor display as described later, but a mark of a device that has not registered is displayed darker than a mark of a device that have been registered.

Since a plurality of measurement devices and skin care devices can be connected and thus a systematic configuration is provided, the display of the above-described marks creates a desire to collect the beauty devices connectable to the smartphone 3.

Additionally, the plurality of skin care devices is connectable as shown in the display screen (register screen 3*d*) in the beauty care as well. As illustrated in FIG. 4, the mark for the device having been registered is displayed bright and the device that has not registered is displayed dark on the register screen 3*d* of the beauty care.

When the camera for skin as the skin condition measuring device 1 is connected as described above, the dedicated application 5j for measuring the skin condition that is executed in the arithmetic processing unit of the smartphone 3 has a function as a measurement data transmitting unit which inputs the image data photographed by the camera for skin via the USB interface 13 and outputs the image data to the data management server 5 on the Internet 4. Additionally, the dedicated application 5j has a function as an analysis result display unit that receives, for example, analysis result data severing as a result of analyzing the measurement data transmitted from the data management server 5 and displays the analysis result data on the display of the smartphone 3.

Additionally, the above-described dedicated application 5j has a function as a user data transmitting unit that executes member registration that is an input of user data (personal information) to become a member (user) who uses the management system for skin condition measurement analysis information administrated by an operator of the data management server 5, and responds to a questionnaire that is an input of accompanying data which does not include predetermined personal information that can specify an individual among the user data.

Additionally, the above-described dedicated application 5j has a function as a data browsing requesting unit that makes a request to enable browsing of the above-described respective user data, measurement data, and analysis result data on the measurement data stored in the data management server 5 as described below.

Additionally, the dedicated application 5j has a function as a data display unit that displays the requested data when the requested data is received from the data management server 5.

Additionally, the dedicated application 5j has a function as the device authentication transmitting unit that transmits the authentication character string received from the skin condition measuring device 1 to the data management server 5.

Additionally, the dedicated application (skin care application) 5j for the skin care device 2 can be downloaded from the data management server 5 and installed in the smartphone 3.

Additionally, the skin care application as the dedicated application 5j of the smartphone 3 as a control method acquiring unit that acquires a control method for the skin care device 2, has a function of controlling the skin care device 2 by acquiring the control method from the data management server 5.

Additionally, the skin care application of the smartphone 3 functions as a schedule acquiring unit that acquires a use schedule for the skin care device 2 from the data management server 5, and functions as a schedule informing unit that informs the use schedule, for example, by displaying the use schedule on the display.

Additionally, when a signal indicating an operation start and a signal indicating operation finish are received from the skin care device 2, the skin care application of the smartphone 3 functions as a use history generating unit that generates use history data including data of a use date and time a and a use time, and transmits the use history data to the data management server 5.

As illustrated in FIG. 1, the data management server 5 includes a user data database 51 for basically storing the above-described user data, a measurement data database 52 for storing the measurement data by the skin condition measuring device 1, a data analysis database 53 for acquiring the analysis result from the measurement data, and a contractor database 54.

As illustrated in FIG. 5 more in detail, the data management server 5 includes a control unit 5k including a CPU or the like for functioning as a server. Additionally, in the data management server 5, the user data database 51 is divided into a plurality of databases and includes, as the user data database 51, a client (user) personal information management database 5a, a beauty care database 5c, a using cosmetic history database 5d, and a care chart database 5o. Additionally, the data management server 5 includes a skin history database 5b, and a detailed analysis result database 5e as the measurement data database 52.

Additionally, the data management server 5 includes a skin reference value database 5g as the data analysis database 53. Additionally, the data management server 5 includes a secondary data user access right management database 5h as the contractor database 54.

Additionally, besides the above-described databases 51 to 54, the data management server 5 includes a device information database 5i that manages the device having the same product serial number such that one skin condition measuring device 1 and one skin care device 2 can be shared among a plurality of the smartphones 3.

Additionally, the data management server 5 includes the skin care database 5l where the control method for the skin care device 2 can be retrieved based on the analysis result data, a calibration database 5m for calibrating the camera for skin (image data), and a schedule database 5n for obtaining a use schedule of skin care device 2 based on a result of simple analysis, besides the above-described databases 51 to 54. Furthermore, the data management server 5 includes a cosmetic maker management database 5q and a registered cosmetic maker database 5p besides the above-described databases 51 to 54.

The client personal information management database 5a stores, as illustrated in Table 1, a client ID, an individual user ID, an individual password, a name, a birthday, age, sex, an address 1 (country), an address 2 (prefecture), an address 3 (city, town, and village (county)), an address 4 (house number (apartment name, room number)), an e-mail address, and billing information (credit card information, etc.) as the data which the user has input by using the smartphone 3. Note that the client ID is an ID assigned on the data management server 5 side, correlated to the individual user ID, and the individual user ID is an ID to be set on condition that the individual user ID of a user does not coincide with that of other user. Additionally, the individual password is used for user authentication together with the individual user ID. Note that two IDs of the client ID and the individual user ID are used for each user as a one-to-one corresponding ID; however, one ID may double as these IDs, or only the client ID may be used as the user ID, or the individual user ID may be used as the user ID.

TABLE 1

Client Personal Information Management D/B
Client ID
Individual user ID
Individual password
Name
Birthday
Age
Sex
Address 1 (country)
Address 2 (prefecture)

TABLE 1-continued

Address 3 (city, town, village)
Address 4 (house number)
E-mail address
Billing information
Product serial number of camera for skin (unique ID)
Product serial number of evaporimeter
Product serial number of melanin meter
Product serial number of other sensor
Product serial number of ion cleansing device
Product serial number of ion introducing device
Product serial number of roller beauty device
Product serial number of ultrasonic wave beauty device
Product serial number of other beauty device Additionally, in the case where data related to a user is stored in each of the databases, all the data is managed by the client ID, and the data related to each user can be acquired by searching each of the databases storing the respective data related to each of the users, using the client ID and searching all the data related to each user.

Therefore, the data of each user is also registered in the client personal information management database 5a, correlated for each client ID.

Additionally, as illustrated in Table 1, the client personal information management database 5a further stores the product serial number received from the skin condition measuring device 1 and the skin care device 2 connected to the smartphone 3. Note that the product serial number is stored after authenticated at the data management server 5 as described later, and in the case where the product serial number is registered in the client personal information management database 5a, authentication for the product serial number is not executed.

Additionally, as illustrated in FIG. 32 in Table 2, the measurement data received from each skin condition measuring device 1 is registered correlated to the client ID and the data input date and time in the skin history database 5b. Additionally, data of each simple diagnosis (analysis) result is registered, correlated to the measurement data, as an analysis result storage unit. Note that, for example, in the case where the measurement data is received from various kinds of skin condition measuring devices 1 within a predetermined time, e.g., 30 minutes, comprehensive simple analysis is executed and data of a result of the comprehensive simple analysis is registered. Further, in the case where detailed analysis is executed for the measurement data, a result of the detailed analysis is informed and then data of the result of the detailed analysis is registered in the detailed analysis result database, correlated to the client ID and the measurement date and time, and a storage address of the data written in the detailed analysis result database is registered in the skin history database.

Note that in the simple analysis, measurement data preliminarily accumulated and a rank of the skin condition as analysis result data are preliminarily correlated and registered in the skin reference value database 5g, and approximate measurement data is selected from the measurement data in the skin reference value database 5g with respect to the measurement data as the measurement result, and the rank correlated to the selected measurement data is output as a result of the simple analysis. This processing is executed by a simple analysis program 5f of the data management server 5 as the skin condition analyzing unit. Additionally, as with the camera for skin, in the case where the measurement data is the image data, image data approximate to the image data photographed by the camera for skin is selected by known image recognition from among the image data as the measurement data registered in the skin reference value database 5g.

Note that as illustrated in Table 2, the input skin image includes an image for texture analysis photographed using the LED lighting of the skin color light, an image for spots analysis photographed using the LED lighting of the white color light, and a skin image photographed using the LED lighting close to natural light or a skin image having colors reproduced by white balance (e.g., automatic white balance) on the occasion of photographing with the LED of the above-described white color light or skin color light. The skin image is used for determining a skin color (color difference due to sunburn, darkening, etc.), for example. Note that, according to the present embodiment, the skin color determination is not executed in the simple analysis but executed in the detailed analysis.

In the simple analysis in which the image for respective analysis is used, texture, spots, wrinkles are determined. Note that the image for texture analysis is used for wrinkles analysis, for example, but other image may also be used. In the simple analysis, plural pieces of image data stored in the skin reference value database 5g as described above and also correlated to the scores (ranks) are compared, image data closest to the image data photographed and input by the user is selected, and the score (rank) of the selected image data becomes a result of simple image analysis. Note that, for example, statistical processing may be performed on plural pieces of collected image data using the ranks of texture, spots, and wrinkles to obtain the deviation values, and then a deviation value of a similar image data may be used as the analysis result.

Additionally, the diagnosis result (analysis result) may be obtained using the above-described image for diagnosis by respective analysis methods for pore, porphyrin in a horny plug, wrinkles, spots, and skin color, as disclosed in JP Patent No. 5080060.

Additionally, in the skin history data, positional information (measured point) measured by a GPS built inside the smartphone 3 on the data input date and time is registered as GPS data. Additionally, weather information at the above-described measured point of the above-described GPS is acquired from a weather information site and registered. Note that the data input date and time is a date and time when respective skin measurement was executed, but may also be a date and time when a result of the simple analysis was stored. The data of respective items is automatically input by executing the skin measurement.

As for a measurement condition flag, for example, in the case where GPS data is distant from a normal measured point, for example, in the case where skin measurement data is input from a measured point being at a predetermined distance or more while measurement has been consecutively executed in the same prefecture or same city more than once until the previous measurement, a flag (measurement condition flag) is set on the measurement data measured at the measured point or the simple analysis result. Note that, in addition to the measured point, in the case where temperature and humidity in the weather information exceeds a predetermined range or in the case where a difference from an average temperature and an average humidity at the measured point on the input date and time exceeds a predetermined range, the flag may be set on the measurement data and the simple analysis result.

The measurement data and the simple analysis result on which the flag have been set are excluded in the case where the statistical processing, such as obtaining an average of respective data, is executed. For example, the data on which the flag has been set is not to be included in a population on the occasion of executing the statistical processing. That is, in the case of being distant from a usual location, or in the case where the weather condition is quite different, environmental conditions may be largely different, and therefore the measurement result is likely to become an abnormal value, and in order to prevent the abnormal value from affecting a statistical result, the data on which the flag has been set is excluded from the population of the statistical processing.

A score (rank) and a deviation value as simple analysis results on the texture, spots, and wrinkles obtained as described above are registered in a simple analysis result on the skin image. Additionally, a skin type is selected based on the analysis results on the texture, spots, and wrinkles, a color in the skin image (redness due to dryness and roughness), presence or absence of eczema caused by atopic dermatitis, and disorder of the texture due to dryness. Note that the skin type is also determined by the detailed analysis, which will be described along with explanation for the later-described detailed analysis result database 5e.

Additionally, the detailed analysis is executed for the measurement data in servers of cosmetic companies, for example, as affiliated companies (a server 61 of cosmetic company A, a server 61 of cosmetic company B), and the server of the cosmetic company is to be the skin condition analyzing unit. Basically, in the same manner as the simple analysis, measurement data approximate to the measurement data obtained by the skin condition measuring device 1 is selected from the database included in a detailed analysis system 62 where the measurement data and the analysis result data are correlated, and the analysis result data correlated to the selected measurement data is output. However, in the detailed analysis, for example, the number of the registered measurement data and the analysis result data are larger than the case of the simple analysis, and are classified more in detail into the database for the detailed analysis such that an analysis result more detailed than the simple analysis can be obtained. Additionally, the measurement data registered in the database may be selected for the detailed analysis with an algorithm original to each of the cosmetic companies so as to obtain an analysis result corresponding thereto.

As illustrated in FIG. 33 in Table 3, history data of skin care articles (cosmetics) is registered for respective cosmetic categories (kinds) correlated to the client IDs in the using cosmetic history database 5d as a using cosmetic specific information storage unit. Note that the history data is data for registering the cosmetics purchased by a user, and product codes of the cosmetics (using cosmetics) purchased by the user are registered via the smartphone 3 as a cosmetic specific information inputting unit by a user cosmetic registration processing described below. This product code is the cosmetic specific information that can specify a cosmetic. Note that an example is provided here, in which JAN (Japanese Article Number) code used in a bar code is used as the product code.

As illustrated on the right side of Table 3, the number indicating the category (kind) of each of the cosmetics, and a product code, a use start date and a use finish date in the history data are registered in the using cosmetic history database 5d.

The right side of Table 3 illustrates a case in which the cosmetic category is the facial wash, as an example, and 1 is registered as the code number of the product category of the facial wash, and the use start date and use finish date are stored correlated to the product code. Note that the use finish date is not registered in the case of being in use (in the case where finish of use is not input).

Note that the use start date may be a date when the above-described user cosmetic registration processing was executed, or for example, a date that a user is instructed to input by the processing of the dedicated application 5j of the smartphone 3 on the occasion of transmitting the image data photographed by the camera for skin when there is a cosmetic which the user started using.

In this case, on the display of the smartphone 3, a list of the product names (+maker names, etc.) of the cosmetics corresponding to respective cosmetic categories is displayed by a pull-down menu or the like based on the data registered in the registered cosmetic database (registered cosmetic storage unit) 5p in which the cosmetic information is registered by the user cosmetic registration processing, and a cosmetic that the user starts using may be selected from the list. Thus, the product code correlated to the cosmetic name is registered and also the input date is registered as the use start date in the registered cosmetic storage unit 5p. In the same manner, the user may be instructed to input the use finish date through the dedicated application 5j of the smartphone 3 when there is a cosmetic that the user finished using.

In this case, the user may select the product name or the like of the cosmetic which the user finished using by displaying a list of data such as the product names of the cosmetics that the user started using with the pull-down menu or the like. In this case also, the product code of the selected cosmetic is input and also the input date is registered as the use finish date. Note that a method of inputting the using cosmetics may be executed as described below by inputting a bar code or inputting data of an extracted cosmetic by searching the registered cosmetic database 5p through a key word search.

Additionally, as for the use finish date, in the case where a cosmetic of the same category is newly registered in the using cosmetic history database 5d, an inquiry may be made to the user whether or not use of the cosmetic of the same category already registered is finished, and the use finish date of the cosmetic may be registered based on an answer to this inquiry. Alternatively, a cosmetic volume (ml) and a recommended use amount (ml/time) may be registered for each of the cosmetics in the registered cosmetic database 5p, and then a value obtained by multiplying the number of times of using the cosmetic per day by a recommended use amount may be summed (accumulated) every day from the use start date in the data management server 5 or the smartphone 3, and also the summed value may be compared with a cosmetic volume, and in the case where the value summed every day exceeds the volume or exceeds a predetermined proportion, such as 90%, of the volume, the user may be informed by the dedicated application 5j that the using cosmetic may be running out or a residual amount is little, and inquired whether or not the user has finished using the cosmetic, and the use finish date may be registered based on the user's answer to the inquiry.

Additionally, on this occasion, a message encouraging the user to purchase the cosmetic remaining little may be displayed, or a URL of a mail-order site of cosmetics linked to a page of the product remaining little may be displayed.

Additionally, a different cosmetic of the same category as the cosmetic remaining little may be displayed for introduction in response to the situation that the cosmetic having been used until then is running out or remaining little. On this occasion, a URL linked to a web page of the cosmetic of a maker or a distributor firm of the cosmetic may be displayed.

As illustrated in FIG. 34 in Table 4, examples of the cosmetic category include a facial wash, a makeup remover, lotion, a milky lotion, cream, serum, a whitening lotion, and others, and each category is correlated to the above-described number. Note that these cosmetic categories are only examples and different categorization may be possible as well.

As illustrated in FIG. 5, in the care chart database 5o as the using cosmetic specific information storage unit, for example, a cosmetic used by the user in the morning and night every day is optionally registered, correlated to the client ID of the user. In the above-described using cosmetic history database 5d, the use start date and use finish date of the cosmetic are registered, but in the care chart database 5o, the cosmetic used in the morning and night every day can be registered. The data of the used cosmetic is input and transmitted to the data management server 5 by means of a scheduler function described below.

Thus, in the care chart database 5o, the client ID, a date, a time zone such as morning and night, and the using cosmetic data such as the above-described product code are registered.

For example, as illustrated on the right side of Table 5 in FIG. 35, the date and time and the time zone such as morning and night and the product code of the used cosmetic are registered in the care chart database 5o. The product code is to be selected from the cosmetic information registered through the above-described user cosmetic registration processing, and the cosmetics registered in the above-described using cosmetic history database 5d are displayed on the screen of the smartphone, and the actually used cosmetic can be selected from the displayed cosmetics and input.

In the beauty care database 5c, as illustrated in Table 6, a beauty care kind code (type) indicating a kind of the skin care device 2, a beauty care start date and time indicating an operation start date and time of the skin care device 2, and a beauty care finish date and time indicating a subsequent operation finish date and time of the skin care device 2 are registered as a use history of each of the skin care devices 2, correlated to the client ID. Note that preferably the start and finish date and time of the skin care device are automatically registered by the dedicated application 5j of the smartphone 3 connected to the skin care device on the occasion of using the skin care device 2.

TABLE 6

Beauty care D/B
Client ID
Beauty care kind code
Beauty care start date and time
Beauty care finish date and time
Data indicating drive conditions
and drive method As illustrated in Table 7 in FIG. 36, in the detailed analysis result database 5e as the analysis result storage unit, the above-described detailed analysis result is registered correlated to the client ID, and a analysis date and time (may include a measurement date and time of the measurement data of which the detailed analysis is asked for) that is a day when the detailed analysis was executed and the analysis result data are registered. Additionally, advice data and recommended cosmetic (skin care articles) data selected corresponding to the detailed analysis result are registered.

Note that the advice data and the recommended cosmetic data are determined at an advice determining unit and a recommended cosmetic determining unit in a server of the cosmetic company A and a database of the cosmetic company B, but each advice and the recommended cosmetic are basically registered correlated to each of the detailed analysis results, and the advice and the recommended cosmetic are determined with determination of the detailed analysis result.

The advice may include, for example, a matter that should be avoided in daily habit or the like and a massage method for skin. Additionally, the recommended cosmetics are a cosmetic and a skin care product suitable for the skin condition found out from the detailed analysis result.

In the detailed analysis result, basically in the same manner as the simple analysis, the measurement data preliminarily registered is classified into ranks, the measurement data approximate to the input measurement data is selected from the registered measurement data, and a analysis result correlated to the measurement data is provided as the analysis result. Here, a skin type, texture, spots, wrinkles, dryness, pores, color, etc. are diagnosed. That is, the number of diagnosing items is larger than that of the simple analysis, and also the analysis result is determined more in detail.

Here, the skin type is determined, for example, as determined in the above-described simple analysis, and basically, plural pieces of skin image data for each skin type are registered in the skin reference value data base 5g for each skin type, and a skin type correlated to the registered measurement data closest to the input measurement data is to be selected by image recognition. Note that the basic method is the same in the detailed analysis, but the detailed analysis is more excellent than the simple analysis in terms of capability of image recognition, an amount of image data registered in the skin reference value database used, and so on. Note that, as illustrated in Table 8, there are following skin types: 1 normal skin, 2 sensitive skin, 3 oily skin, 4 combination skin, 5 dry skin, 6 atopic skin, etc. and these codes are registered in the detailed analysis result database 5e.

TABLE 8

| Skin type | NO. |
|---|---|
| Normal skin | 1 |
| Sensitive skin | 2 |
| Oily skin | 3 |
| Combination skin | 4 |
| Dry skin | 5 |
| Atopic skin | 6 |
| Others | 7 |

The skin reference value database 5g is used for the simple skin analysis as illustrated in Table 9, in which the skin condition is classified into 10 ranks, for example, from bad condition to good condition, respectively as skin color analysis from the skin texture, skin spots, and image data, sebum analysis from image data, moisture analysis from the evaporimeter data, and so on, corresponding to the measurement data, and the respective ranks are correlated to the plural pieces of the measurement data registered as described above.

Therefore, a rank indicating the skin condition can be obtained by searching the skin reference database by using the measurement data measured in the skin condition measuring device 1. This rank is to be a result of the simple analysis.

TABLE 9

Skin reference value D/B
Texture analysis (ranks 1 to 10)
Spots (ranks 1 to 10)
Skin color analysis (ranks 1 to 10)
Sebum analysis (ranks 1 to 10)
Moisture analysis (ranks 1 to 10)

As illustrated in Table 10 in FIG. 37, a product serial number of each of the skin condition measuring devices 1 and a product serial number of each of the skin care devices 2 are registered in the device information database 5*i*. Authentication may be executed with the product serial number stored in the device information database 5*i*.

Further, in the device information database 5*i*, each of the above-described product serial numbers of the skin condition measuring devices 1 and the skin care devices 2 are correlated to the client ID. In the case where the serial number is authenticated as described above and each of the skin condition measuring devices 1 and skin care devices 2 is authenticated, the authenticated serial number is registered correlated to the client ID corresponding to the smartphone 3 connected to each of the devices. In this case, for example, the one skin condition measuring device 1 or skin care device 2 can be used by maximum three persons, that is, can be shared by the maximum three smartphones 3. Therefore, when a fourth client ID is registered with respect to one product serial number in the device information database, use of the skin condition measuring device 1 or skin care device 2 having the above-described product serial number is inhibited via the smartphone 3 of this fourth client ID. For example, an error occurs in the above-described dedicated application 5*j* of the smartphone 3 and this causes the skin condition measuring device 1 or the skin care device 2 to be unusable.

As illustrated in Table 11 in FIG. 38, in the secondary data user access right management database 5*h*, a user (contractor, for example, a company that develops skin care articles, such as a cosmetic company), a client ID, a user's user ID, and a user password are set, and thus a secondary data user can be authenticated.

Additionally, in the secondary data user access right management database 5*h*, data of a user search level and a user access level, and the billing information are registered correlated to the user ID. Note that the billing information is data of billing in the case where a secondary data user searches data or acquires accessible data, and data usage fee is charged to the user based on the billing information.

Additionally, the usage fee varies depending on the search levels and the axel levels, and the more the number of searchable key words (search item) is, the higher the usage fee is, and the higher the axel level is, the higher the usage fee is.

Additionally, in Table 11, differences of the search key words (search items) due to differences of concrete search levels are indicated, and also differences of accessible data, namely, data that can be output as the search result due to the difference of the access level are indicated. The respective search items in search level 1 and search level 2 indicated in Display 11 correspond to data blocks as a data group including the data respectively correlated to the client IDs. For example, the measurement data and the analysis result data are divided into blocks for each measuring method.

Note that age, sex, address 1, address 2, and address 3 are the data registered in the above-described client personal information management database 5*a*, but the databases accessible by the secondary data user are the skin history database 5*b*, the using cosmetic history database 5*d*, etc. excluding the client personal information management database.

That is, the secondary data user is not allowed to see the data of an individual user ID, an individual password, a name, a birthday, a whole residential address including address 4, an e-mail address, billing information, and a serial number as predetermined personal information, and the user is not allowed to access the client personal information management database 5*a*.

Therefore, a user sees the information of age, sex, address 1, address 2, and address 3 by the skin history database 5*b* where the data is registered correlated to the client IDs, or by an independent database.

Here, the search levels are levels obtained by classifying, into levels, the search items in which search conditions are input. The search items are set in a part of data blocks among the data blocks of the above-described measurement data, analysis result data and accompanying data, and correspond to the respective search items of search levels 1 and 2 in Display 11. That is, as the data groups, there are the data block of address 1, the data block of age, etc. and these data blocks are set as the search items.

The search items indicated in search level 1 include information that can specify each of the individual clients from the items of the data registered in the client personal information management database, and the items of the accompanying data excluding important information such as the billing information. Additionally, search level 2 is higher than search level 1, and search level 2 includes all of the search items classified into search level 1. That is, each search level includes the search items of the lower search level. In other words, the items classified into search level 2 includes the search items classified into search level 1 and further additional search items, and the cosmetic use history is added as the search items as illustrated in Table 11.

The access level is a level obtained by classifying, into levels, the data blocks to which the data which can be output as search results belongs. For example, the measurement data includes, as described above, the data blocks of the input skin image, the input data of the evaporimeter, the input data of the melanin meter, and the like, and in the case of wishing to acquire only the input skin data as the search result, the data block of the input skin image is selected, thereby outputting only the data retrieved from the input skin image.

Additionally, in the case of level classification of the data blocks of the access levels, a higher access level includes the data blocks classified into a lower access level.

Here, in search level 2 indicated in Display 11, it is possible to retrieve various kinds of the measurement data and the analysis result data as the search items based on the using cosmetic history data of the cosmetic for skin care, such as the cleansing history data, facial wash history data, lotion history data, serum history data, and moisturizing cream history data. Note that the history data of the using cosmetics is data to be registered in the later-described using cosmetic history data 5*d*. Note that the classification of the cosmetics for skin care is an example and may be the classification of the using cosmetic history data as well.

In the using cosmetic history data, a product coat that can specify a cosmetic, and a use time of the cosmetic (for example, a use start date, and a use finish date in the case of stopping using or finishing using)) are registered. For example, in the case of wishing to see the measurement data and analysis result data for a person using a specific cosmetic and then searching this using cosmetic history data by using the specific cosmetic as a search key, it becomes possible to retrieve, for example, the measurement data and analysis result data for a period serving as the use time of the using cosmetic. The analysis result data is a result of analyzing (diagnosing) the measurement data, for example, by the skin condition measuring device 1, and as described below, the skin condition is represented by a score, and the higher the score is, the better the skin condition is.

In the case of retrieving the analysis result data (analysis result) based on the using cosmetic history data as described above, a analysis result of the skin condition during the use period of the cosmetic can be obtained. In this case, for example, whether the score of the analysis result of the skin condition tends to increase or decrease, whether there is progress at a high score or at a low score while the cosmetic is being used, and the like can be investigated for many users.

That is, effect of the cosmetic can be investigated. Additionally, the analysis result data can be searched by searching plural kinds of the cosmetics classified into the plural kinds as described above as the search items, and it is also possible to determine synergetic effects and offset of the effects of the plurality of cosmetics, and the like. Additionally the plural kinds of the analysis results based on the kinds of the skin condition measuring devices 1, such as the result on the texture and spots based on the skin image, the result from the melanin meter and the result from the evaporimeter, can be obtained as the analysis results, and therefore it is also possible to determine which analysis result each of the cosmetics is effective or ineffective for, and the like. As a result, retrieving the analysis result data by using the cosmetics in use as the search keys is extremely useful for development of the cosmetics.

Further, the data management server 5 in the management system for skin condition measurement analysis information includes the calibration database 5m. As illustrated in Table 12, in the calibration database 5m, image data in the case of imaging a black and white pattern by the camera for skin under predetermined conditions is registered, correlated to ranks of brightness, and image data in the case of imaging a color pattern is registered correlated to ranks of color tones. For example, ranks 0 to 10 are registered as the ranks of brightness and ranks 0 to 10 for respective colors of blue, green, and red are registered as the ranks of color tone.

While the calibration data is to be obtained by comparing the registered image data correlated to each of the ranks with the measured image data, for example, the rank 5 is set as a standard, and when the rank is lower than this rank, color is dark or the corresponding color is pale, and when the rank is higher than the rank 5, color is bright or the corresponding color is deep. The brightness or color of the LED light is adjusted and the image data is corrected by using this calibration data, thereby suppressing influence of individual difference of each camera for skin and the like.

TABLE 12

Calibration D/B
Brightness (rank) 1 to 10
Blue (rank) 1 to 10
Red (rank) 1 to 10
Green (rank) 1 to 10

In the skin care database 5l in which the control methods for the skin care device 2 are registered correlated to the ranks as the analysis result data. For example, the ranks in the simple analysis where the above-described skin reference value database is used are correlated to the control methods for the skin care device 2, as illustrated in Table 13.

For example, in the skin care database 5l under the assumption of the case where the skin condition measuring device 1 is the camera for skin in the texture mode and the skin care device 2 is the ion cleansing device and the case where the output level of the ion cleansing device can be replaced, for example, in three steps, the highest output level is set to 3 and the operation time is set to 15 minutes in the case where the skin texture rank is rank 1 to rank 3. Additionally, in the case where the texture rank is 4 to 7, the output level is set to mid level 2 and the operation time is set to 10 minutes. Additionally, in the case where the texture rank is 8 to 10, the output level is set to lowest level 1 and the operation time is set to 5 minutes.

Thus, the skin care device 2 can be efficiently used corresponding to the skin condition.

TABLE 13

| Skin care D/B | | | |
|---|---|---|---|
| Texture analysis (rank) | 1-3 | 4-7 | 8-10 |
| Ion cleansing device | | | |
| Output level | 3 | 2 | 1 |
| Operation time | 15 min. | 10 min. | 5 min. |

In the schedule database 5n of the data management server 5 in which use schedule data for the skin care device 2 is registered correlated to the ranks as the analysis result data, for example, the ranks in the simple analysis using the above-described skin reference value database are correlated to the use schedule for the skin care device 2, as illustrated in Table 14.

For example, in the case where the measuring unit is the camera for skin in the texture mode and the skin care device 2 is the ion cleansing device, ion cleansing is to be executed every day when the skin texture rank is rank 1 to rank 3 in the schedule database 5n. Additionally, when the texture rank is 4 to 7, the ion cleansing is to be executed three times a week, and when the texture rank is 8 to 10, the ion cleansing is to be executed once a week.

Thus, the skin care device 2 can be efficiently used corresponding to the skin condition.

Note that, from the schedule in the schedule database 5n, a user may set, for example, a concrete day of the week and a time to execute the ion cleansing to make a more concrete schedule.

TABLE 14

| Schedule D/B | | | |
|---|---|---|---|
| Camera for skin Texture analysis (rank) | 1-3 | 4-7 | 8-10 |
| Ion cleansing device Schedule | 7 days a week | 3 days a week | 1 day a week |

On the occasion of registering a cosmetic in the above-described using cosmetic history database 5d, the registered cosmetic database 5p in which the data of the respective cosmetics is registered is referred to. For example, the cosmetic that a user uses is retrieved from the registered cosmetic database 5p by using a bar code (JAN code), a key word search, etc., to be registered in the skin history database 5b.

Note that a brand name (product name) and a product code as the information registered for each of the cosmetics in the registered cosmetic database 5p are the cosmetic specific information that can specify the cosmetic, and it is difficult to specify the cosmetic by other items information. Here, the product name and product code that can specify the cosmetics are adopted as the cosmetic specific information, and referred to as cosmetic information in combination with information such as volume, a price, and a release date that is difficult to specify the cosmetics. Note that the maker name may be combined with the product name into the cosmetic specific information for specifying the cosmetics.

As illustrated in Table 15 in FIG. 39, the registered cosmetic database 5p is divided into a user input permitted item, a maker input item, and a system automatic input item.

These are the items under the assumption that cosmetics not registered yet are to be registered, and for example, in the case of creating the registered cosmetic database 5p at the time of system construction or the like, an operator, a system administrator, etc. of the data management server 5 are to register existing cosmetics. In this case, it is difficult to register all of the cosmetics as there are many cosmetics. For example, it is difficult to register the cosmetics of small and medium-sized makers abroad. Additionally, sometimes even relatively major cosmetic may be slipped out of registration.

Additionally, it is necessary to register a new product because the new product is not registered in the registered cosmetic database 5p. In the case where the system administrator investigates and inputs release of all of new products, such a case is costly.

Thus, according to the present embodiment, the data of the non-registered cosmetics in the using cosmetic history database 5p is input by a user and a person in charge of a maker side, as described above.

On the occasion of user cosmetic registration as described later, data of the cosmetic which cannot be retrieved with a JAN code or other search key word can be written in the registered cosmetic database 5p as non-registered data.

In this case, the user inputs (temporary registration) a cosmetic category, a maker name, a brand name, volume, and a product code (JAN code) as the user input permitted item for the non-registered cosmetic via the smartphone 3 as a temporary registration unit. Note that the user may not input all of the items, and may input, for example, the product name and maker name as required items. When the product name, maker, etc. of the cosmetic that has not registered are input by the user, the cosmetic maker management database 5q (cosmetic maker contact information storage unit) illustrated in Table 16 is searched based on the input maker name, and a person in charge of the maker and an e-mail address of the maker are read out. An e-mail in which a preset sentence for requesting registration of the cosmetic, a URL of a web page for registration, a maker ID, a maker password, etc. are written is created, and transmitted to the read out e-mail address of the maker for above-described person in charge. Note that, here, the e-mail transmission to the person in charge of the maker is executed by the data management server 5, but the data management server 5 may merely assist creating the e-mail, the operator may eventually execute transmission of the e-mail, and the data management server 5 functions as a communication assisting unit. Note that the communication assisting unit may execute processing from e-mail creation to e-mail transmission.

TABLE 16

| Cosmetic maker management D/B |
| --- |
| Maker ID |
| Maker password |
| Maker e-mail address |
| Maker name |
| Name of person in charge |

The person in charge having received the e-mail, for example, accesses the page for registration written in the e-mail and receives authentication using the maker ID and maker password, and thus the data can be input in the maker input item in the registered cosmetic database 5p (registration permitting unit). However, what is accessible on this occasion is only a record in which the maker name corresponding to the maker ID input at the time of authentication is registered. Therefore, authentication is executed using the above-described maker ID and password such that a record in which a maker name of other company is registered cannot be accessed by the person in charge of the maker.

There is high probability that the person in charge of the maker register information of the own company product, for example, in the case of determining that a propaganda effect, user support, etc. are expected from registration of the information of the own company product (cosmetic) in major cosmetic-related sites the person in charge knows, and in cosmetic-related sites operated by major enterprises The person in charge of the maker can input the input items including a release date, a production termination date for a cosmetic of which production has already ended, an appearance photograph, a price, a recommended use amount per time (per day), ingredient data, effect by each of the above-described skin types, PA and SPF against ultraviolet, a color number, and so on. Additionally, the person in charge of the maker can write in the user input permitted item, and can write data in an item without user input, and an item having mistake.

Thus, a work for new registration of the cosmetic by the operator or the like on the data management server 5 side becomes unnecessary, and the management cost on the data management server 5 side can be reduced.

Note that, as the ingredient data, effective ingredients used in the cosmetic are preliminarily registered, and the presence or absence of the effective ingredients is to be input. Additionally, an effective ingredient not preliminarily registered may also be registered as other effective ingredients.

Additionally, in the ingredient data, not only the effective ingredients contained in the cosmetic but also an ingredient not contained in the cosmetic are preliminarily registered, and in the case of inputting the ingredient not contained as being present, the fact that the cosmetic does not contain the ingredient is to be input. For example, when fragrance-free is selected, the fact that no fragrance is contained is to be indicated.

Next, a description will be given for the management method for skin condition measurement analysis information in the management system for skin condition measurement analysis information according to the present embodiment with reference to flowcharts in FIGS. 6 to 18.

In the method according to the present embodiment, first the dedicated application 5j for managing the skin condition measurement analysis information is downloaded and installed in the smartphone.

User registration processing after starting the dedicated application 5j will be described with reference to a flowchart in FIG. 6.

When the application 5j (step Sa1) is started, it is determined whether or not processing of user registration has been already executed (step Sa2).

Since the user registration has not been executed on the occasion of starting the application 5j initially, the user registration is to be executed. When the application 5j is started at the second time or later, the user registration is already finished, and therefore user registration processing is finished and the application is to be started.

In the user registration, input of the individual user ID and individual password is encouraged (step Sa3), and after the user inputs the individual user ID and the individual password, the input individual user ID and individual password input are transmitted from the smartphone 3 to a management terminal of the data management server 5 (step Sa4). Note that the management terminal is a terminal for operating the data management server 5 and basically a part of the data management server 5.

In the data management server 5, the client ID is automatically generated in response to receipt of the individual user ID and individual password (step Sb1). Additionally, processing of registering the received individual user ID and individual password in the personal information database as the client personal information management database 5a (step Sb2).

Additionally, in the smartphone 3, the set user ID is registered in a storage unit inside the smartphone 3 (step Sa5). Next, input of personal information is encouraged, and the above-described personal information such as a name and a birthday is input (step Sa6). When the personal information is input, the personal information is transmitted from the smartphone 3 to the data management server 5 (step Sa7) and the user registration processing ends in the smartphone 3.

Additionally, in data management server 5, the personal information received in the client personal information management database 5a is registered correlated to the individual user ID and the client ID (step Sb3), and the processing is finished.

After the user registration processing is finished as described above, a menu screen is displayed. On the menu screen, the following menus are displayed: 1. register sensor, 2. skin diagnose, 3. detailed skin analysis result display, 4. beauty care, 5. skin condition improvement determination, and 6. skin history display.

On this occasion, in the case where the application has not been started by connecting the skin condition measuring device 1, execution of sensor registration processing in menu 1 is encouraged.

The sensor registration processing will be described with reference to a flowchart in FIG. 7.

At the stage where menu 1 is selected or thereafter, it is determined whether or not the skin condition measuring device 1 (sensor) is connected (step Sc1), and the smartphone is to be in a state of waiting for the skin condition measuring device 1 to be connected.

When the skin condition measuring device 1 is connected to the smartphone 3 with the USB interface 13, the data indicating the sensor type is read from the data of a device descriptor of the USB interface 13 as described above and also the product serial number is read from a string descriptor (step Sc2). It is determined from the product serial number whether or not the skin condition measuring device 1 has been already registered (step Sc3). In the case where the skin condition measuring device 1 has been already registered, the processing ends.

In the case where the skin condition measuring device 1 has not been registered, transmission is made to the sensor type and the data management server 5 of the product serial number (step Sc4).

The data management server 5 receives the sensor type and the product serial number (step Sd1). The data management server 5 authenticates the product serial number (step Sd2). Note that the product serial number is set by a predetermined algorithm and a character string randomly set is less likely to become a legitimate product serial number. Based on the algorithm, it is to be determined whether or not the product serial number is a legitimate number. Note that all of the legitimate product serial numbers may be registered in the device information database 5i, and in the case where a product serial number is not retrievable from the device information database 5i, authentication may be deemed to have failed.

Additionally, in the case where authentication of the product serial number has failed, a corresponding error message, for example, an error message indicating that the sensor is unusable is generated (step Sd3).

Additionally, in the case where authentication of the product serial number has succeeded, in the device information database 5 it is determined whether or not the same product serial number is already correlated to the client ID corresponding to other smartphone 3, and also in the case where the same product serial number is already correlated to the client ID of other smartphone 3, it is determined whether or not the number of the correlated clients IDs is less than three (step Sd4).

Here, in the case where three client IDs are already correlated, a message indicating that "this skin condition measuring device 1 is not usable with this smartphone 3 because the number of smartphones 3 using this skin condition measuring device 1 is over the limit" is generated as a corresponding error message (step Sd3).

In the case where the number of the client IDs correlated to the product serial number is less than three, the skin condition measuring device 1 of this product serial number becomes usable. In this case, the sensor type and the product serial number are registered in the client personal information management database 5a as a sensor information database and in the device information database 5i (step Sd5).

Next, the data indicating authentication success or authentication failure is transmitted to the smartphone 3 as a processing result in the data management server 5 (step Sd6). Additionally, in the case of authentication failure, the above-described error message is transmitted to the smartphone 3.

The smartphone 3 receives the data (step Sc5), and it is determined whether or not the data indicating authentication success is received and thus it is determined whether or not registration has been completed. (Step Sc6)

In the case of registration failure, the received error message is displayed on the display (step Sc7), and in the case of completion of registration, the sensor type and the product serial number are registered in the storage unit inside the smartphone 3 (step Sc8), and on the occasion where the skin condition measuring device 1 is connected to the smartphone 3, the registered product serial number is confirmed, thereby controlling not to execute authentication in the case where the serial number is already registered as described above.

Next, the skin analysis in menu 2 will be described with reference to a flowchart in FIG. 8. First, on the occasion of starting the application, the menu screen is displayed. Here, in the case where the skin condition measuring device 1 is connected, in determination on whether or not the skin condition measuring device 1 is connected (step Se1), it is determined that the skin condition measuring device 1 is connected, and it is determined whether or not an authentication character string as the sensor ID is already registered (step Se2); in the case where the sensor is not registered, the above-described sensor registration processing is executed (step Se3), and in the case where the sensor is already registered, the skin condition measuring device 1 becomes operable; and when the skin condition measuring device 1 is operated, the measurement data is received from the skin condition measuring device 1 (sensor) (step Se4).

Next, whether or not the detailed analysis is desired is input, and for example, which enterprise is to be selected from among a plurality of enterprises providing the detailed analysis is input (step Se5).

Further, the measurement data (sensor data) received from the skin condition measuring device 1, the client ID stored in the smartphone 3, and a data input date and time when the measurement data was received from the skin condition measuring device 1 are transmitted to the data management server 5 (step Se6).

In the data management server 5, the client ID, the measurement data, the data input date and time are registered in the skin history database 5b (step Sf1).

The analysis on the skin condition is executed based on the measurement data (step Sf2). That is, the approximate measurement data is selected from the measurement data registered in the skin reference value database, and the ranks for the respective items corresponding to the measurement data are determined (step Sf3).

The skin analysis result and/or the determined ranks are registered in the skin history database 5b (step Sf4).

In the above-described steps, it is determined whether the detailed skin analysis is desired (step Sf5) and in the case where the detailed skin analysis is desired, the measurement data and necessary data for the detailed analysis (e.g., age, etc.) are transmitted to a server of a detailed analysis supplier such as a cosmetic company (step Sf6).

After receiving the data from the data management server 5 (step Sg1), the server of the cosmetic company transmits a message indicating acceptance of the request for the detailed skin analysis to the data management server 5 (step Sg2). Moreover, the detailed skin analysis is started. As for the detailed skin analysis, here, the sensor data, and the data of detailed skin analysis result, etc. are exchanged via a communication line. Alternatively, the skin analysis supplier may be permitted to access a specified portion of the skin history database 5b and a specified portion of the detailed analysis result database 5e such that the skin analysis supplier may directly access the databases 5b and 5e to obtain the sensor data and write the detailed analysis result in the detailed analysis result database 5e.

The data management server 5 receives the above-described message (step Sf7) and also creates display data for displaying a result of the simple analysis executed in the data management server 5 on the smartphone 3 (step Sf8).

This display data is transmitted to the smartphone 3 (step Sf9).

The display data is received in the smartphone 3 (step Se7), and displayed on the display of the smartphone 3 as the simple skin analysis result (step Se8).

Additionally, in the server of the cosmetic company as the server of the skin analysis supplier, on the occasion where the detailed skin analysis ends (step Sg3), the data of the detailed skin analysis result is transmitted to the data management server 5 (step Sg4).

The data is received in the data management server 5 (step Sf10), and the data of the detailed skin analysis result is written in the detailed analysis result database 5e (step Sf11). Further, the data indicating completion of the detailed skin analysis is transmitted to the user of the smartphone 3 (step Sf12). As for the detailed skin analysis, here, the result is informed such that the user can confirm the result on the screen by using a command of the analysis result display, but the detailed analysis result may be sent via e-mail as well.

The smartphone 3 receives the data from the data management server 5 (step Seg) and also the data indicating completion of the detailed skin analysis is displayed on the display of the smartphone 3 as the message (step Se10). Note that the result of the completed detailed skin analysis can be displayed on the smartphone 3 side by the user reading the detailed analysis result database 5e of the data management server 5 by using the smartphone 3, but the detailed analysis result may be displayed on the smartphone 3 by using the electronic mail from the data management server 5 and the server of the cosmetic company.

Note that in a server 61 of the skin analysis supplier, the data is transmitted from the data management server 5 and received to obtain the necessary data for the detailed skin analysis; however, the server 62 of the skin analysis supplier may be used as a client to access the specified portion of the skin history database 5b or the detailed analysis result database 5e of the data management server 5 to which accessing is permitted, so as to directly read and write the data.

Next, Display processing for the detailed skin analysis result in menu 3 will be described with reference to a flowchart of FIG. 9.

In the smartphone 3, a question "a latest result or a past result" is displayed to have a user select one detailed skin analysis result to be displayed between the two results (step Sh1). It is determined whether the detailed skin analysis result chosen for display is the latest result or the past result (step Sh2). In the case where the detailed skin analysis result chosen for display is not the latest result, a request for date and time data of the past detailed skin analysis is made from the smartphone 3 to the data management server 5 (step Sh3).

The data management server 5 receives the above-described request (step Si1), and the date and time data of the past detailed skin analysis is collected with reference to the skin history database 5b or the detailed analysis result database 5e (step Si2).

The collected date and time data is transmitted from the data management server 5 to the smartphone 3 (step Si3).

The smartphone 3 receives the date and time data (step Sh4) and displays dates and times of the past detailed skin analysis such that the user can select a date and time (step Sh5).

When the user selects a date and time from screen display of the dates and times, a result of the detailed skin analysis on a date and time corresponding to the selected date and time is specified (step Sh6), and a request for transmitting the detailed skin analysis result of the specified date and time is made (step Sh7).

Note that in the case where the latest detailed skin analysis result is determined to be displayed in step Sh2, the latest detailed skin analysis result is specified in step Sh6, and a request for transmitting the latest detailed skin analysis result is to be made in step Sh7.

The data management server 5 receives the request (step Si4), and searches, for example, the detailed analysis result database 5*e* based on the received data (step Si5), and then transmits the detailed skin analysis result of the specified date and time to the smartphone 3 together with the advice data and the recommended cosmetic data (step Si6).

The smartphone 3 having received the data (step Sh8) displays the detailed skin analysis result (step Sh9). On this occasion, the recommended cosmetic and the advice are displayed.

Next, beauty care processing in menu 4 will be described with reference to a flowchart in FIG. 10.

In the case of selecting menu 4, it is determined whether or not any beauty care as the skin care device 2 is attached (step Sj1), and in the case where the skin care device is not attached, the processing enters a standby state until the skin care device 2 is attached by returning to the determination processing again.

In the case where the skin care device 2 is attached, the type and product serial number of the skin care device 2 are read by the smartphone 3 as in the case of the skin condition measuring device 1, and it is determined whether or not the product serial number has been already registered, as in the case of the skin condition measuring device 1 (step Sj2), and in the case where the product serial number has not been registered yet, the processing of registering the product serial number of the skin care device 2 is executed as in the case of the skin condition measuring device 1 (step Sj3). Since the registration processing is the same as the above-describe sensor registration processing, a description thereof will be omitted.

In the case where the product serial number is already registered, it is determined whether the skin care device 2 has started driving (step Sj4), and in the case where the skin care device has not started driving yet, the processing enters a standby state for driving start by returning again to the determination on whether or not driving is started.

The determination on whether driving is started or not is executed by monitoring a power source of the skin care device 2.

After the skin care device 2 starts driving, it is determined whether or not the skin care device 2 stops driving (step Sj5), and in the case where the skin care device does not stop driving, the processing enters a standby state for driving stop by returning to the determination on whether or not driving is stopped. In the case where the skin care device 2 stops driving, a date and time of driving start and a time from driving start to driving stop are stored in the storage unit inside the smartphone 3 (step Sj6).

It is determined whether or not the skin care device 2 is to be detached (step Sj7), and in the case where the skin care device is not to be detached, the processing enters again a standby state for driving start of the skin care device 2, while in the case where the skin care device 2 is detached under this state, the processing returns to step Sj7 without waiting for the skin care device 2 to start driving and it is determined that skin care device 2 is detached.

In the case where communication with the data management server 5 is available at the stage where the skin care device 2 is detached, the above-described driving start date and time and driving time of the skin care device 2 are transmitted to the data management server 5 (step Sj8). Note that, in the case where a communication line with the data management server 5 is not connected, the stored driving date and time and driving time are collectively transmitted to the data management server 5 after the communication line is connected.

The data management server 5 receives the driving start date and time and the driving time of the skin care device 2 (step Ski), and registers the received driving start date and time and driving time in the beauty care database 5*c*.

Next, skin condition improvement determination in menu 5 (comparison between the latest analysis result and a analysis result on a base date) will be described with reference to a flowchart in FIG. 11.

When menu 5 is selected, a message encouraging a user to input the base date in the comparison of analysis results is displayed (step Sl1).

When the base date is input, the input base date is set. Note that, in the case where the base date is not input within a predetermined time, the base date previously input when menu 5 is selected may be used as the base date (step Sl2).

That is, in the case where it is determined that the base date is not input within the predetermined time after menu 5 is selected, in the determination on whether or not the base date is input (step Sl3), the previous base date stored in the storage unit inside the smartphone 3 is set (step Sl5). In the case where the base date is input before the predetermined time passes, the input base date is stored in the storage unit inside the smartphone 3 (step Sl4).

When the base date is determined, the base date is transmitted from the smartphone 3 to the data management server 5 (step Sl6). The data management server 5 receives the base date (step Sm1), and searches the skin history database 5*b* for the simple analysis result data of the received base date (step Sm2).

Next, the data of latest simple analysis result is searched from the skin history database 5*b* (step Sm3).

Next, it is determined whether an option has been set (step Sm4), and in the case where the option has not been set, the data of simple analysis result of the base date and the data of the latest simple analysis result are transmitted to the smartphone 3 (step Sm7).

Note that, as the option, the simple analysis result of the base date and. Not only the latest simple analysis result but also all of monitored analysis results may be searched (step Sm5). Further, history data of a cosmetic used between the base date and the date and time of the latest analysis result may be read as the option by referring to the using cosmetic history database (step Sm6).

In the case where such an option has been set, the data of the simple analysis results between the base date and the latest, and the history data of a cosmetic used therebetween are transmitted to the smartphone 3, as described above (step Sm7).

The smartphone 3 receives the above-described data (step Sl7), and basically displays the data of the simple analysis result of the base date and the data of the latest simple analysis result in a comparison state (step Sl8).

Additionally, in the case where the option is set (step Sl9), the simple analysis results between the base date and the latest are displayed and also the cosmetic use history during this period is displayed (step Sl10).

Note that, in the data management server 5, the use history of the skin care device 2 from the base date to the date and time of the latest simple analysis may be acquired by referring to the beauty care database 5*c*, and the acquired use history of the skin care device 2 may be displayed.

By simultaneously displaying the simple analysis result of the base date and the latest simple analysis result, whether skin condition is improved, not changed, or deteriorated can be found out.

Additionally, transition of the skin condition can be found out more in detail by displaying all of the simple analysis results between the simple analysis result of the base date and the latest simple analysis result.

Additionally, how effective the cosmetic and the skin care device 2 are can be determined by seeing the use history of the cosmetic and the use history of the skin care device 2 therebetween. Note that the same processing may be executed for the detailed analysis result instead of the simple analysis result, and the detailed analysis result of the base date and the latest detailed analysis result may be comparably displayed on the smartphone 3.

Next, the skin history display in menu 6 (displaying the skin history from the base date to the latest skin analysis) will be described with reference to a flowchart in FIG. 12.

When menu 6 is selected, processing of displaying a message encouraging input of the base date in the comparison of the analysis results is executed (step So1).

In this case, the base date is to be input by the user (step So2). Note that, in the case where the base date is not input within a predetermined time, the base date input previously when menu 6 is selected is adopted as the base date.

That is, in the case where the base date is not input within the predetermined time after menu 6 is selected, the previous base date stored in the storage unit inside the smartphone 3 is set. In the case where the base date is input before the predetermined time passes, the input base date is stored in the storage unit inside the smartphone 3.

That is, it is determined whether the base date is input within the predetermined time (step So3). In the case where a new base date is input, the input base date is stored in the storage unit provided inside the smartphone 3 (step So4), and in the case where no new base date is input, the base date previously stored inside is read out for use (step So5).

When the base date is determined, the base date is transmitted from the smartphone 3 to the data management server 5 (step So6). The data management server 5 receives the base date (step Sp1), and searches the skin history database 5b to acquires the simple analysis result data during the period from the received base date to the latest simple analysis result (step Sp2).

Next, it is determined whether an option has been set (step Sp3), and in the case where the option has not been set, data of all of the simple analysis results during the period from the base date until obtainment of the latest simple analysis result is transmitted to the smartphone 3 (step Sp6).

Additionally, in the case where the option has been set, the use history data of the skin care device 2 from the base date to the date and time of the latest simple analysis is acquired as the option by referring to the beauty care database 5c in the data management server 5 (step Sp4).

Additionally, in the case where the option has been set, history data of a cosmetic used between the base date and the date and time of the latest analysis result is acquired as the option by referring to the using cosmetic history database 5d (step Sp5).

In the case where the above-described option has been set, the data of the simple analysis result between the base date and the date and time of the latest simple analysis and the history data of the skin care device 2 and a cosmetic used therebetween are transmitted to the smartphone 3.

The smartphone 3 receives the above-described data (step So1) and displays the all of the simple analysis results between the base date and the date and time of the latest simple analysis as the history in chronological order, for example, in a graph (step So8). Additionally, it is determined whether or not the option has been set (step So9), and in the case where the option has been set, the use history for the skin care device 2 and the use history of the cosmetic during the period are displayed (step So10).

In this case also, the progress of the skin condition can be found out and also the effects of the cosmetic and the skin care device 2 can be determined. Additionally, in this case also, the detailed analysis result may be acquired and displayed on the smartphone 3 instead of the simple analysis result.

Thus, whether the skin condition is improved or not can be determined by seeing the measurement data and the analysis results as the data arranged in chronological order.

Additionally, a moving image can be displayed by sequentially displaying the image data as the measurement data, but the number of the data is more likely to be small. In this case, change in the skin can be seen as smooth image data by complementing gaps between the respective image data by morphing.

Additionally, the skin condition is not necessarily kept in a good condition and may deteriorate temporarily. For example, in the summer time, the pores may stand out. Under such a situation, a user may not want to see the magnified image of one's own skin. Therefore, the image data during the time when the skin condition is not good may be cut off in the case of clearly indicating chronological change in the skin by sequentially displaying the image data as described above. In this case, morphing is applied between the previous image data and the subsequent image data of the cut-off image data, and thus the deteriorated skin condition can be made unclear although the image data is partly cut off. Note that since the deteriorated skin condition is made unclear, preferably an advice on the deteriorated skin condition is provided by voice or screen display.

Additionally, the smartphone 3 is provided with a storage area in which control data for the skin care device is stored, and the user can change the setting to update the control data. For example, the user can optionally set the output level of the skin care device. Additionally, the control data stored in the storage area is accessible by the data management server 5 and controllable from the data management server.

Next, a method of inputting the using cosmetic data in the using cosmetic history database 5d will be described with reference to a flowchart in FIG. 13. The user inputs a cosmetic type, such as foundation, a milky lotion, and lotion, from the smartphone 3 (step Su1). Next, a name of the cosmetic is input (step Su2). Next, it is determined whether or not input is completed (step Su3). Here, in the case of registering a plurality of cosmetics, the cosmetic types are input again. In the case where input is completed, the input data and the client ID are transmitted to the data management server 5. The data management server receives the input data (step Sv1), and the cosmetic name and the data input date are stored in the storage area corresponding to the client ID in the using cosmetic history database 5d.

Based on the using cosmetic history database 5d, a time when the cosmetic runs out can be estimated from the registration date of the cosmetic. In this case, cosmetic advice can be provided at the time when the cosmetic runs out.

Next, with reference to a flowchart in FIG. 14. A method of acquiring the above-described measurement data and the accompanying data attached thereto from the contractor client 6 as a secondary user terminal will be described.

First, a user ID and a password are input from the contractor client 6 of the cosmetic company or the like (step Sq1).

Next, a search condition is input (step Sq2). For example, a search condition key is input. Note that the search condition here includes the above-described search items. For example, in the case where the search item is age, the search condition (search condition key, search condition expression) is to be, combination of the search item and a range of the data serving as the search item for narrowing down the data, for example, such as "age is from 30 to 40". Note that what is combined with the search item is not limited the range of the data serving as the search item, and may be any condition that can narrow down the data, such as a key word. For example, in the case of searching the measurement data and the analysis result data by setting as the search item the cosmetic that a user is using, a condition may be adopted where a key word such as a kind of cosmetic, a cosmetic name, and a maker name of the cosmetic is combined with the search item in order to narrow down the cosmetic.

Next, output request data of requesting the data to be output (kind of data to be output) under the above-described search condition is input (step Sq3). The input user ID, password, search condition, and output request data are transmitted to the data management server 5 (step Sq4).

The data management server 5 receives the above-described data (step Sr1), and authentication processing for the user ID and password is executed (step Sr2). An authentication result is determined (step Sr3), and in the case where authentication is not successful, an error message indicating the fact that authentication is not successful is created (step Sr9). In the case where the user ID and the password are authenticated, whether or not the received search condition is the permitted search condition for the user as the secondary user of the data is collated by referring to a user search level in the secondary data user access right management database 5*h* (step Sr4).

A collation result is determined (step Sr5), and in the case where the search condition is a non-permitted search condition according to the collation result, an error message corresponding to the collation result is created (step Sr9). Additionally, in the case the collation of search condition is successful, next, whether or not the received output request is the data of the permitted access level for the secondary user is collated by referring to the user access level (step Sr6). A collation result is determined (step Sr7), and in the case where collation is not successful, an error message corresponding to the collation result is created (step Sr9).

In the case where collation of the output request data is successful, search is executed under the collated search condition, and also the data requested as the output request data is acquired from each database (step Sr8), and the acquired data is transmitted (step Sr10). Additionally, the created error message is transmitted in the case where collation is not successful in any of the stages.

The secondary user terminal (contractor client 6) receives the data (step Sq5), and it is determined whether or not the data is the error message (step Sq6), and in the case of error, the error message is displayed (step Sq7), and in the case where the data is the data requested to output, the data is displayed on the screen or output as a file and also stored (step Sq8).

Thus, the secondary user of the measurement data, etc. can acquire the data in the range of the kinds of data set by the access level, using the search condition key set by the search level (e.g., search item search range). That is, the data that is worth the cost can be acquired and utilized.

Next, a modified example of data acquisition by the secondary user of the data will be described.

As illustrated in a flowchart of FIG. 15, an operator is allowed to input a user ID and a password in the contractor client 6 which is the secondary user terminal (step Ss1).

The input user ID and password are transmitted to the data management server 5 (step Ss2). The data management server 5 receives the user ID and the password (step St1), and executes authentication (collation) processing for the user ID and the password (step St2). It is determined whether or not collation is successful (step St3), and in the case where collation is not successful, a corresponding error message is created (step St4).

In the case where collation is successful, a permitted search condition key for the secondary user is extracted by referring to the secondary data user access right management database 5*h* based on the client ID corresponding to the user ID (step St5).

Additionally, in the same manner, the secondary data user access right management database 5*h* is searched with the client ID to extract a data item (kind) accessible by the secondary user (step St6).

The extracted search condition key and data item are set in a data table (step St7).

The above-described error message or data table is transmitted to the contractor client 6 (step St8).

The contractor client 6 receives the error message or the data table (step Ss3).

It is determined whether or not the error message is received (step Ss4), and in the case of error, the error message is displayed (step Ss5). In the case where there is no error, the permitted search condition key (search item) for the display of the contractor client 6 and the accessible data item are displayed (step Ss6).

For example, as illustrated in FIGS. 24 and 25, a display screen 85 corresponding to search level 1 or a display screen 86 corresponding to search level 2 in Table 11 are displayed on the display of the contractor client 6 as the permitted search items (search condition items). On the display screen 85 and display screen 86, by selecting a search item to which a search condition is input, the display is switched over to an image for inputting the condition in the selected search item, and the user can input the condition.

In this case, the search item that is not permitted in search level 1 but permitted in search level 2 is displayed only on the display screen 86 of search level 2 and is not displayed on the display screen of search level 1; therefore, in spite of a contract of search level 1, an error is not issued when the condition is input in the search item not permitted in search level 1 but permitted in search level 2, and the operator's operation is facilitated, while the input processing for the search condition can be simplified.

In the same manner, in the case of specifying an item indicating a data block to which the data searched and output under the above-described search condition belongs, a display screen 87 corresponding to access level 1, a display screen corresponding to access level 2 (not illustrated), or a display screen 88 corresponding to access level 3 in Table 11 is displayed as illustrated in FIGS. 26 and 27. That is, the specified screen of a data output item in accordance with the user's access level is displayed.

In this case also, when there is no item of a data block classified into the access level, the data item is not displayed and the data item cannot be selected. When the data item is selected on the display screens 87 and 88 of the access levels, only the data of the data item selected on the display screens 87 and 88 from among searchable (extractable) data is to be output by inputting the search condition in the above-described search item.

In this case also, an error is not issued by mistaking the data item to be output, and the operator's operation is facilitated, while the input processing for the search condition can be simplified.

The output request data in the range of the search condition key and the above-described data item is input based on the screen display (step Ss7), and the input data is transmitted to the data management server 5 (step Ss8). The data management server receives the data (step St9). In the data management server 5, the data of the data item that matches the search condition and is permitted to be accessed is acquired from each of the databases based on the search condition key and the data item permitted to be accessed (step St10).

The acquired data is transmitted to the contractor client 6 (step St11). In the contractor client 6, the above-described data (step Ss9) is received, and the received data is displayed on the display of the contractor client 6 or output and stored as a file (step Ss10).

In this case also, the data of the data item permitted by the access right in the range of the set search condition key can be acquired in the same manner as the above-described case, and also an error can be reduced because the available search condition key and the data item permitted to be accessed are displayed.

Next, user cosmetic registration processing will be described with reference to a flowchart in FIG. 16. In this processing, the user registers using cosmetics in the using cosmetic history database 5d by using the registered cosmetic database 5p in which the cosmetic data is registered.

The user starts the dedicated application 5j of the smartphone 3 and also selects cosmetic registration from the menu.

Thus, a cosmetic registration screen 71 illustrated in FIG. 19 is displayed on the smartphone 3. On the cosmetic registration screen 71, a button switch of starting a bar code scanner program using the digital camera of the smartphone 3 is displayed and also an input screen for the key word search is displayed (step A1). Based on the user operation, it is determined whether to execute bar code input by using the bar code scanner or key word search (including search per item) (step A2).

In the case where the bar code scanner is started by the user, the digital camera of the smartphone starts and becomes ready to photograph the bar code; processing of recognizing the bar code is executed by image recognition; and when the user adjusts a photographing range of the digital camera to focus the bar code, a bar code image is recognized and the bar code is photographed (step A3).

A pattern of the photographed bar code is converted to a character string (numerical string) by the image recognition processing. The numerical string is a JAN code, and the JAN code is to be extracted from the bar code (step A4). Here, the maker, product, etc. indicated by the JAN code may be specified based on the JAN code, but it is preferable that analysis on the JAN code be executed on the management terminal side of the data management server. In this case, a search command of instructing search in the registered cosmetic database 5p by using the JAN code or the key word is transmitted to the data management server 5 (management terminal thereof) (step A6).

Note that, in the case of key word search, a corresponding key word for each of the predetermined items may be input as illustrated in the cosmetic registration screen 71, and also a key word may be input regardless of the items. Note that, on the occasion of inputting the key word for each of the items, search can be executed by inputting a key word only in an item for which the key word is known.

The management terminal receives the JAN code or the key word, and the search command from the smartphone 3 (step B1).

The management terminal searches the registered cosmetic database 5p of the data management server 5 for the cosmetic, using the bar code or the key word (step B2). The management terminal transmits, to the smartphone 3, a search result obtained by execution of the search (step B3). The search result includes a case where not only one cosmetic but also a plurality of cosmetics are retrieved and a case where no cosmetic can be retrieved.

The transmitted search result is received by the smartphone 3 (step A7).

In this case, it is determined whether or not there is more than zero information indicating the cosmetic as the search result, that is, whether there is one or more searched cosmetic, or whether no cosmetic can be retrieved as a non-registration determining unit (step A8).

In the case where there is a searched cosmetic, the information of the searched cosmetic is displayed. For example, as illustrated in a screen display 72 of FIG. 19 in the case where the cosmetic is retrieved, an image (photo) showing appearance of the cosmetic, a product name, a release date, ingredients, etc. are displayed. However, in the case where a plurality of cosmetics is retrieved, the plurality of cosmetics is displayed. This display screen is called a selection display screen (step A9). On this screen, the user can select because, even when the retrieved cosmetic is only one, there is a case in which the retrieved cosmetic is different from the cosmetic that the user intends to register.

In the smartphone 3, it is determined whether the user has selected the one cosmetic on the selection display screen or selected the fact that there is no cosmetic which the user intends to register (step A10).

In the case where the user has selected the one cosmetic, the JAN code (product code) of the cosmetic is determined (step A11). Note that the JAN code is acquired on the occasion of searching the registered cosmetic database 5p.

In step A8, in the case where there is no searched cosmetic, the smartphone 3 outputs a message indicating that the cosmetic that the user intends to register is not registered in the registered cosmetic database 5p (step A12).

Next, a user registration screen 73 for registration by the user of the non-registered cosmetic that cannot be retrieved is displayed on the smartphone 3 as a non-registered cosmetic specific information inputting unit (step A13). In step A10, in the case where there is no product intended to be registered in the search result, the processing also proceeds to step A13, and the user registration screen 73 is displayed.

On the user registration screen 73, the items that the user can register are the same as the above-described user input permitted item in the registered cosmetic database 5p, for example, a category, a maker name, a brand name, a JAN code, volume, and so on. The data is input by the user in the input items of the cosmetic (step A14), When a registration button is touched, the input data in the respective items and a new cosmetic registration command of instructing the data registration of the non-registered cosmetic are transmitted to the management terminal (step A15). Note that, on the occasion of data input in the respective items by the user, preferably the JAN code is required to be input. Note that, for inputting the JAN code, the above-described bar code scanner function may be used.

In the management terminal, the data of the item input by the user and the new cosmetic registration command are received (step B4).

The received data is registered in the registered cosmetic database 5p of the data management server 5 by the management terminal (step B5).

On this occasion, the cosmetic maker management database 5q is searched based on the registered cosmetic maker or JAN code as described above, and an e-mail encouraging input of the cosmetic information in the registered cosmetic database is transmitted to a person in charge of the maker based on an e-mail address of the maker and a name of the person in charge, etc. (step B6).

The message or the like on the above-described occasion is a preliminarily prepared message added with the maker name, the name of the person in charge, the JAN code of the cosmetic intended to be registered, and so on. Additionally, the e-mail message includes the maker ID and maker password for permitting access to the registered cosmetic database 5p. Thus, the person in charge of the maker can access the registered cosmetic database 5p, and access (writing, deleting, etc.) to the data of cosmetics other than the cosmetics of the maker corresponding to the maker ID is inhibited.

In the management terminal, on the occasion where the new registration processing for the cosmetic to the registered cosmetic database 5p ends and at least the data of the user input permitted item is registered in the registered cosmetic database 5p, the JAN code of the newly registered cosmetic is transmitted to the smartphone 3. In the smartphone 3 having received the JAN code of the newly registered cosmetic, a screen 74 displaying completion of the registration is displayed.

In the smartphone 3, in the case where the cosmetic that the user intends to register is searched and in the case where the above-described new registration is executed, a writing command of instructing to write the cosmetic data to be registered in the using cosmetic history database 5d, the client ID of the user, the data of the cosmetic category, and the JAN code as the product code of the cosmetic are transmitted to the management terminal (step A16).

The management terminal having received the data from the smartphone 3 (step B7) writs the received product code in the record of the received client ID in the using cosmetic history database 5d (step B8) and transmits, to the smartphone 3, the data indicating that registering the cosmetic in the using cosmetic history database 5d has ended.

In the smartphone 3, a message indicating end of registration of the cosmetic (purchased cosmetic) which the user uses is displayed (step A17). On this occasion, a display screen 75 for displaying the cosmetic registered in the using cosmetic history database 5d can be displayed on the smartphone.

In the above-described registration method by the user of the cosmetic (cosmetic purchased by the user) which the user uses, in the case where the cosmetic is not registered on the occasion where the user intends to register the purchased cosmetic with reference to the registered cosmetic database, the user can register the data of the non-registered product, and also in the case where the user finds a non-registered cosmetic, the record of the cosmetic to be newly registered in the registered cosmetic database 5p can be completed by contacting the person in charge of the cosmetic maker (distributor firm) to inform of the fact and to further supplement the data of the cosmetic.

Note that, when the person in charge of the cosmetic maker who sends the e-mail is, for example, a person in charge of public relations, the person in charge considers that registering data of the own company products in the database which is likely to catch many people's attention is a part of the public relations, and is more likely to register the data of the own company products in the registered cosmetic database 5p.

That is, when the user finds a cosmetic that is not registered in the registered cosmetic database 5p on the occasion of registering a cosmetic of the user, the user can input the JAN code, maker name, or product name (brand name) of the cosmetic that is not registered. Thus, on the data management server 5 side, the fact of existence of the cosmetic that is not registered can be found out and it becomes possible to request the maker to register the data of the cosmetic that is not registered. Additionally, the cosmetic data is more likely to be correctly input by the person in charge of the maker who may know the cosmetic data, and the operator or the like on the data management server 5 side does not need to input the cosmetic data to be newly registered.

Therefore, the data of non-registered cosmetics such as a new product is to be sequentially registered in the registered cosmetic database 5p even though the operator and administrator of the data management server 5 almost do not execute maintenance work for updating the data of the registered cosmetic database 5p, and thus the management cost can be reduced.

Next, user skin history display processing will be described with reference to a flowchart in FIG. 17. In the user skin history display processing, a graph is created in chronological order for each item of the detailed analysis results (simple analysis results may be also used) as scores registered in the detailed analysis result database 5e, and also the data (product name, etc.) of the used cosmetic is displayed using the care chart database 5o in the same chronological order. A time axis of the graph and a time axis of the using cosmetic are made the same such that a relation between changes in the skin condition and the using cosmetic can be easily seen and grasped.

Here, a method of inputting a using cosmetic in the care chart database 5o will be described with reference to FIG. 20 before describing the user skin history display processing. A using cosmetic input screen 76 is displayed on the smartphone 3 by selecting the care chart from the menu of the dedicated application 5j on the smartphone 3 and selecting input care from the menu screen of the care chart. On a using cosmetic input screen, a product name and a checkbox of the cosmetic without the use finish date input are displayed among the cosmetics registered in the using cosmetic history database 5d for each cosmetic category, such as a facial wash, a makeup remover, and lotion.

The user can input the using cosmetic by touching a registration button after touching the checkbox corresponding to the used cosmetic. Note that the using cosmetic can be input by dividing a daily time zone into morning and night, and inputting the cosmetic used in the morning and the cosmetic used in the night separately even on the same date.

Additionally, on a calendar screen 77 illustrated in FIG. 20, as a scheduler function 78, by touching a date in the past on the calendar the cosmetic used on that day can be displayed with morning and night divided. Note that preferably the used cosmetic is input in the case of having measured the skin condition. Accordingly, in the case of executing diagnostic measurement of skin, the using cosmetic input screen 76 may be displayed or a photographing program for the camera for skin may be started when the data is input on the input screen 76, before and after the analysis.

Alternatively, the cosmetics registered as the using cosmetics in a using cosmetic registration database may be automatically registered in the care chart database 5o, deeming that the user constantly uses these cosmetics. Additionally, it is also possible to register a set (combination) of cosmetics that the user uses in the storage inside the smartphone and to have the set of cosmetics so as to be automatically registered in the care chart database 5o every day. In the case where the cosmetic to be used in the morning is different from the cosmetic to be used in the night, a morning set and a night set may be stored inside the smartphone so as to be automatically registered in the care chart database 5o every day. In the above-described cases, the contents of the care chart database 5o may be revised by touching a relevant date in the calendar of the scheduler function only in the case where care is not executed or in the case where a cosmetic different from the usual set is used.

The user skin history display processing is executed by using the care chart database 5o in which the using cosmetics are thus registered, the simple analysis results on skin images in the skin history database or the detailed analysis result database 5e.

In the user skin history display processing, in the smartphone 3, the user starts the dedicated application 5j and selects the skin history display from the menu, and thus, the smartphone 3 transmits, to the management terminal of the data management server 5 from the skin history database 5b or the detailed analysis result database 5e, the scores in past three months corresponding to the client ID of the user as the analysis results on texture, spots, etc., the date registered in the care chart database 5o, and a transfer request command that requests transfer of the using cosmetic data in the morning and night during the past three months together with the client ID (step C1), for example.

Note that the requested data period is not limited to the past three months, but may be, for example, the past half year, the past one year, etc. Additionally, the requested data period may be settable by the user as described below. Additionally, the detailed analysis result may be retrieved from the detailed analysis result database 5e.

In the management terminal having received the transfer request command (step D1), the scores as the detailed analysis results on the texture, spots, etc. during the specified period (three months) are copied based on the client ID from the skin history database 5b to a data table, correlated to the chronological order (step D2).

Next, in the management terminal, the data (JAN code) of the cosmetic used during the specified period is copied to the data table, correlated to the chronological order, based on the client ID from the care chart database 5o (step D3).

Next, the registered cosmetic database 5p is searched based on the JAN code of the cosmetic copied to the data table as described above, and the data such as the maker name, brand name, and appearance photograph of the cosmetic correlated to the JAN code is copied to the data table, correlated to each cosmetic (JAN codes) (step D4).

The data table to which the data extracted from the respective databases is copied as described above is transmitted to the smartphone 3 (step D5).

In the data smartphone 3 having received the data table (step C2), as illustrated in a skin history display screen 79 in FIG. 21, a graph (line graph) having a vertical axis indicating the scores of the detailed analysis result and a horizontal axis indicating the date (time axis) is displayed for each of the items such as texture and spots (step C3). Additionally, the name of the cosmetic used during the corresponding period is displayed for each category of the cosmetic name, and also a use period is displayed for each cosmetic (for each cosmetic category) in conformity with the horizontal axis (dates) of the graph of the detailed analysis result (step C4). In the display of the graph of the detailed analysis result as the analysis result data, the analysis result data is arranged along the chronological order, and the display screens 79 and 80 become the chronological display of the analysis result data.

For example, a band for each cosmetic category is displayed in parallel to the horizontal axis corresponding to the horizontal axis of the graph, and the use period and a non-use period are indicated in different colors. Note that, in the case where a different cosmetic in the same cosmetic category is used during the above-described period, the color of the period indicated in the band can be varied for each cosmetic.

Additionally, by touching a morning button and a night button displayed at a lower portion of the skin history display screen 79, the detailed analysis result and the using cosmetic in the morning and the detailed analysis result and the using cosmetic in the night can be displayed in a switchable manner. Additionally, a graph for the scores of the analysis results may by created and displayed by using an average of the analysis results in the morning and night may be used as the analysis result on that day.

Additionally, when the color portion of the band indicating the use period displayed for each cosmetic category is touched on the skin history display screen 79, the product name, price, release date, ingredients, etc. of the cosmetic used during that period is popup displayed as shown in a skin history display screen 80. Thus, since the analysis result is displayed in the graph as the analysis result data and the use period of the cosmetic is displayed in the band while the product name and the like indicating the cosmetic are popup displayed, the analysis result data and the cosmetic data indicating the cosmetic are to be displayed in parallel.

Thus, as the cosmetic data, the period during which each cosmetic is used and the detailed analysis result during that period can be seen by associating with dates. Thus, whether the skin condition is improved, not changed, or deteriorated on the occasion of using the cosmetic can been seen. Additionally, in the case of having used a cosmetic called A, for example, it can be determined that the score in the analysis result has been relatively high, or it can be confirmed which cosmetic has been used during the period in which the analysis result is relatively high.

On the skin history display screen 79 in FIG. 21, a display period of the skin history can be changed by pinch-in and pinch-out operation of shortening and elongating a distance between two fingers while touching the screen with the two fingers.

In this case, for example, data for one year which is longer than a default display period may be transmitted from the management terminal of the data management server 5 instead of transmitting the data of, for example, the three-month default display period from the data management server 5 side; on the occasion of displaying, the data for three months may be used, and in the case where there is a request for changing the display period as described above, the skin history from 4th month to 12th month may be made displayable by using the data for one year already transmitted, instead of requesting again the data management server 5 side to transfer the data. In this case, a relatively long waiting time can be prevented from occurring due to communication or processing between the smartphone 3 and the management terminal of the data management server 5 by starting the display processing after receiving the data of the three-month default display period and receiving the data from 4th month to 12th month in parallel. Note that the transfer data at this time with the above-described measurement condition flag added thereto is excluded. For the excluded data, interpolation processing is executed based on the data preceding and following data of the excluded data, so that a graph having a smooth shape can be obtained.

Note that in addition to the above-described method of displaying the analysis result within a certain period, the method of displaying the skin history is capable of executing comparative display processing for a today's analysis result and a analysis result of any date in the past.

As illustrated in FIG. 22, a comparison display screen 81 is displayed, and the latest measurement data such as today's data (yesterday's data is also possible) and the specific data in the past can be comparatively displayed for comparison. The comparable data is, for example, the skin image for texture and spots by the camera for skin, the score of the detailed analysis result (or simple analysis result), and the advice at the time of the detailed analysis. Note that the today's data and the data of the date in the past are displayed for morning and night because the data is input in the morning and night as described above.

In the above-described display processing, the smartphone 3 is to request the management terminal to transfer the above-described data to be displayed of today or yesterday (basically, the latest date when the data is input) from the skin history database 5b or the detailed analysis result database, and transfer the above-described data to be displayed of the date in the past input by the user in the smartphone 3 and registered in the skin history database 5b or the detailed analysis result database.

On the other hand, the management terminal extracts data of the corresponding two dates from the skin history database 5b of the data management server 5 and outputs the extracted data to the smartphone 3. Thus, the comparison display screen 81 (comparative display) illustrated in FIG. 22 can be displayed on the smartphone 3 as a simultaneous comparison unit.

According to this display, it becomes possible to easily compare the present skin condition with the skin condition of, for example, a month ago, half a year ago, or one year ago, and the user can easily determine whether or not the skin condition is improved.

Next, effect confirming processing for a specific cosmetic will be described with reference to a flowchart in FIG. 18.

This processing is processing of displaying data of a detailed analysis result (simple analysis result) on the skin condition during a predetermined period, such as first three months of a use period of a cosmetic in the skin history database 5b of a different user having the same skin type, among other users who use the cosmetic that a user uses or may use.

In the effect confirming processing for the specific cosmetic, the user starts the dedicated application 5j of the smartphone 3 and selects effect confirmation of the cosmetic from the menu. Thus, the smartphone 3 executes processing of displaying a cosmetic selecting screen 83 (including a target person narrow-down screen described later) illustrated in FIG. 23 (step E1). On the cosmetic selecting screen 83, the screen switches to the cosmetic selecting screen (list display) (not illustrated) by pushing ">" in an input box for each cosmetic category so as to encourage the user to select a cosmetic. To select the cosmetic, input may be executed using the cosmetic input screen described in the flowchart in FIG. 13.

The user specifies the cosmetic of at least one category on the cosmetic selecting screen 83, using the selecting screen or the like, and the smartphone 3 stores (step E2). Note that, as illustrated in the cosmetic selecting screen 83, the cosmetic product name (brand name) or the like can be input for each category, and a plurality of cosmetics in various categories can be input.

Next, the target person narrow-down screen is displayed as a part of the above-described cosmetic selecting screen (step E3). Here, conditions to narrow down the target person are age (generation) and a place of residence. Note that the processing continues even though no condition to narrow down the target person is input. On the target person narrow-down screen, in principle, the target person is required to have the same skin type as the user although such a requirement is not included in the input items, and narrowing down is to be executed by the skin type.

The conditions to narrow down the target person input by the user are stored in the smartphone 3 (step E4).

The smartphone 3 transmits, to the management terminal, the above-described input and stored specific data (for example, a maker name and a brand name) of the cosmetic, the conditions to narrow down the target person, and the current skin type of the user (step E5).

Note that in the transmission between the smartphone 3 and the management terminal, an ID that can specify the user (smartphone 3), such as the client ID or the like, is basically used for authentication, and the skin type may be obtained from the detailed analysis result database 5e in which the skin types are registered or the skin history database 5b including the detailed analysis result data on the data management server 5 side, by using the client ID of the user authenticated as described above even without transmitting the skin type.

Additionally, on the cosmetic selecting screen (target person narrow-down screen) 83 illustrated in FIG. 23, the items to be displayed among the items of the detailed analysis result can be selected by an ON/OFF button, but as for the data of the analysis result to be displayed as a graph, all of the items are transmitted from the management terminal such that the items to be displayed can be selected on the smartphone 3 side.

The data transmitted from the smartphone 3 is received by the management terminal as a part of the data management server 5 (step F1). In the management terminal as a user extracting unit, a client ID that is using or has used the cosmetic input by the user is retrieved first by the using cosmetic history database 5d. Note that, in the case where a plurality of cosmetics is input, the client IDs (group of target persons) are narrowed down by AND search. Additionally, the client personal information management database 5a is searched by using the client ID, and the generation and place of residence input as the narrow-down conditions, and the group of target persons is further narrowed down (step F2).

A use period from the use start date to the use finish date (present time in the case where the use finish date is not registered) of the cosmetic input by the user in the using cosmetic history database 5d is obtained. Additionally, in the case where the user continuously purchases and uses the cosmetic, such a continuous period from the use start date to the use finish date is obtained as the use period. Note that the use period may also be obtained from the using cosmetic of the narrowed-down target persons for each date in the care chart database 5o.

In this case, when there is a date having non-registered data, a period including the date having non-registered data is adopted as the use period if the same cosmetic is used before and after such a date. A display period of the analysis result is determined from the use period of the target person (step F3). On this occasion, for example, an average use period of the target persons may be adopted, or the use period of a predetermined proportion of the target persons, such as 80%, may be adopted.

Note that the default display period is set to the display period obtained as described, but the obtained display period can be changed by pinch-in or pinch-out operation, for example.

Next, the management terminal as a rank extracting unit extracts the score (rank, deviation value) of the detailed analysis result during the above-described set display period from the skin history database 5b. On this occasion, the client IDs of the above-described target persons are narrowed down, and also the data of the simple analysis result or the detailed analysis result is read out from the skin history database from the use start date to the use finish date in the using cosmetic history database 5d. A data table in which the data read out is listed in conformity with the chronological order (time axis by a date unit) having the data of the use start date at the top is created (step F4). Note that the data at this time having the above-described measurement condition flag added thereto is not registered in the table.

Next, an average of, for example, a score of the analysis result in the morning and a score of the analysis result in the night is obtained for each date and for each item in the above-described data table. Next, an average of the scores of all of the target persons for each number of days from the use start date is obtained for each item. A data table is created using the obtained average scores arranged along the time axis corresponding to the number of days from the use start date.

In this data table, the averages of the respective scores of all of the narrowed-down target persons are arranged in the chronological order. In this data table, the data to be displayed in a graph on the smartphone 3 is registered. The data table is transmitted to the smartphone 3 by the management terminal as a rank transmitting unit (step f5).

The smartphone 3 receives the data table for the graph (step E6).

Using the received data table, the graph having the horizontal axis as the time axis and the vertical axis as the average score is displayed in a line graph as shown in a graph display screen 84 of FIG. 24 in which the average scores of all of the narrowed-down target persons are arranged along the time axis for each item.

Additionally, it has been described that an average of the score in the morning and the score in the night on the same date is obtained; however, display of a graph of the scores only in the morning and display of a graph of the scores only in the night may be made displayable in a switchable manner besides the display of the graph of the average of the morning and night. Additionally, in the case where the scores of the analysis result only for the morning or only for the night are registered by the target persons, either the score in the morning or the score in the night is adopted as the score of the day instead of the average score of the morning and night. Additionally, in the case where there is a date without registered score, the score may be interpolated with the scores of preceding or following dates.

Note that it has been described that the average value of all of the narrowed-down target persons is adopted, but statistical processing or the like other than averaging may be applied to the scores of the target persons as well.

Additionally, for example, the number (proportion) of the target persons having a score change with time passage within a predetermined range, the number (proportion) of the target persons having the score change with time passage higher than the predetermined range, and the number (proportion) of the target persons having the score change with time passage lower then predetermined range may be displayed.

According to the above-described effect confirming processing for the specific cosmetic, the user can find out how the skin analysis result changes when the target person of the same skin type uses the specific cosmetic. In the case where the specific cosmetic is the currently using cosmetic, the user can determine whether to continue to use the cosmetic or change to other cosmetic based on this processing. Additionally, in the case where the specific cosmetic is a cosmetic that is not used yet and is considered for purchasing, the user can use this processing as a reference.

Next, a description will be given for hiding processing for the user to delete the measurement data and the analysis result data from display of the analysis result or the like on the smartphone 3.

The case where the user intends to delete the analysis result data is, for example, the case where when the analysis result data is lower than a previous analysis data, the cause thereof seems to be situational problems such as getting too much sun, particularly, being tired, etc., and measurement problems such as an operation mistake in the skin condition measuring device 1 or difference in measurement conditions.

As above, as the processing for a user to delete the analysis result data and the measurement data, a button (key) 92a for instructing deletion of the simple analysis result from the skin history database 5b is displayed on a display screen 90a on which the simple analysis result (may be the detailed analysis result) is displayed as the analysis result data, as illustrated in FIG. 28. Additionally, a display area 91a of the display screen is an area in which an acquisition time of the analysis result is displayed. In the case where the acquisition time is today, the result is displayed as a today's result, and in the case where the acquisition time is in the past, a date in the past is displayed in a display area 91b of a display screen 90b as illustrated in FIG. 29. This past result is output when the user specifies a specific date from the calendar screen in FIG. 21.

In the case where the user finds the problems as described above in the analysis result, the hiding processing is started by touching the above-described button 92a. By touching the button 92a, a signal instructing start of the hiding processing is transmitted from the smartphone 3 to the data management server 5. Here, the diagram illustrated in FIG. 28 is the today's analysis result (analysis result data) obtained from the skin image photographed by the camera for skin as the skin condition measuring device 1, and the hiding processing is started such that the simple analysis result on today's skin image obtained from the skin image and the skin image cannot be viewed by the smartphone 3.

The signal transmitted from the smartphone 3 to the data management server 5 instructs deletion of the simple analysis result on the skin image obtained today from the display of the smartphone 3. Note that a simple analysis result by the evaporimeter and a simple analysis result by the melanin meter are registered in the skin history database 5b as the simple analysis results, in addition to the simple analysis result on the skin image.

In the skin history database 5*b* illustrated in FIG. 40 in Table 17, a skin image deletion flag can be set correlated to the simple analysis result on the skin image, an evaporimeter data deletion flag can be set correlated to the simple analysis result by the evaporimeter, and a melanin meter data deletion flag can be set correlated to the simple analysis result by the melanin meter. Additionally, in the hiding processing for the simple analysis result by the evaporimeter and the simple analysis result by the melanin meter, abnormal value processing is started for the simple analysis result by the evaporimeter and the simple analysis result by the melanin meter by touching the above-described "delete from history" buttons 92*a* and 92*b* displayed on the respective analysis result display screens.

According to the hiding processing in the data management server 5, the skin image deletion flag is set for, for example, the simple analysis result on a today's skin image based on the signal transmitted from the smartphone 3 by touching the above-described buttons 92*a* and 93*b*. In the same manner, the evaporimeter data deletion flag and the melanin meter data deletion flag are respectively set in the case of touching the buttons 92*a* and 92*b* displayed on the display screens of the simple analysis result by the evaporimeter and the simple analysis result by the melanin meter.

Additionally, setting of the respective flags can be set not only for the analysis result of the day but also for the past analysis result, and as illustrated in FIG. 29, in the case where a request for displaying the past analysis result is transmitted to the data management server 5 from the smartphone 3 and the past analysis result is displayed on the smartphone 3, the "delete from history" button 92*b* same as the case of the display of the today's analysis result is displayed and by touching this button 92*b*, a signal instructing the hiding processing of inhibiting display on the smartphone 3 of any of the simple analysis result on the skin image, the simple analysis result by the evaporimeter, and the simple analysis result by the melanin meter on the date in the past is transmitted from the smartphone 3 to the data management server 5.

Thus, in the data management server 5, the above-described flag is set for the specified analysis result on the specified date by the signal from the smartphone 3.

Once these flags are set, the data management server 5 determines whether or not there is a analysis result (analysis result data) set with the flags among the analysis results to be output to the smartphone 3 in the case where a request for displaying the respective analysis results is received from the smartphone 3 side, and the processing is executed so as not to transmit the analysis result set with the flags to the smartphone 3. In this case, a measurement result corresponding to the analysis result not to be displayed may also be prevented from display.

Thus, the analysis result instructed to be deleted from the history as described above enters a state of not being displayed on the smartphone 3.

In this case, even when deletion of data from the history is instructed from the smartphone 3. Actually, deletion from the skin history database 5*b* is not executed, and the data is used in the statistical processing for the analysis result and also can be output to the contractor client 6 in the case where search is made by the contractor client 6.

Next, the abnormal value processing of processing an abnormal value in the data management server 5 will be described.

The abnormal value processing is executed, for example, in the data management server 5 regardless the user's operation. When a analysis result as the analysis result data is acquired, it is determined whether or not a value of the analysis result (simple analysis result on the skin image, simple analysis result by the evaporimeter and simple analysis result by the melanin meter) is an abnormal value, and in the case where the value is determined as an abnormal value, the analysis result data as the analysis result, and the measurement data that has been analyzed on the occasion of acquiring the data are deleted from the skin history database 5*b*. Note that the abnormal value is likely to adversely affect a statistical processing result in the case of being used in the statistical processing or the like.

In a determining method for the abnormal value, for example, a value exceeding a preset allowable range a on a positive side and a negative side of a value of a value of the previous analysis result is adopted as the abnormal value. Additionally, as the determining method for the abnormal value, a value exceeding the allowable range a on the positive side and the negative side of a value estimated by interpolation from the values of a plurality of the past analysis results may be used as the abnormal value.

In the case where a value is determined as the abnormal value in the abnormal determination, the value of the analysis result determined as the abnormal value is not stored in the skin history database because the value of the analysis result is determined as the abnormal value, and the user is informed of this fact via the smartphone 3. According to this abnormal value processing, accuracy of the data in the analysis result can be improved.

Next, a description will be given for a case of using the digital camera of the smartphone 3 having a conversion lens 1*a* (illustrated in FIGS. 30 and 31) attached thereto for photographing the skin, such as photographing the above-described image for texture analysis, image for spots analysis, and skin image.

In this case, since resolution (number of pixels) of the digital camera is varied depending on the smartphone models and provides different image quality, the dedicated application 5*j* transmits image quality data for each of the models of smartphones 3 to the skin history database 5*b*. Here, the image quality data is, for example, resolution. The resolution may be, for example, the number of effective pixels of an imaging device or the number of pixels of the photographed image data.

Additionally, the resolution may be a size and the number of pixels of the imaging device of the digital camera. At the time of analysis and analysis, analysis and analysis are executed by converting each image to the image quality data of predefined items of analysis and analysis. For example, in the case where the skin image has low resolution with respect to the image quality data to be used for the skin analysis, the resolution is increased by super-resolution technology to execute analysis and analysis, and in contrast, in the case where the skin image has high resolution, the pixels are reduced to decrease the resolution to execute the analysis and analysis.

The above description is a method of registering the image data and the image quality data thereof in the database such as the skin history database inside the server, but as another method, the image quality may preliminarily be determined for an image to be registered in the skin history database, and when the image is transmitted from the user, the image may be converted to the image quality defined by an application inside the smartphone or a program inside the server to be registered in the database. In this case, the image quality data may be unnecessary as the item in the database. In the following, this method will be described.

For example, as illustrated in FIGS. 30 and 31, in the management system for skin condition measurement analysis information, the conversion lens 1a for photographing the skin is attached to the digital camera of the smartphone 3, and the skin image such as the above-described image for texture analysis, the image for spots analysis, and the skin image is photographed by using the digital camera provided in the smartphone 3 to send the image data of each of the photographed images to the data management server 5, and to execute analysis and analysis on the skin condition by using the image data. Alternatively, the skin is photographed by a camera for skin built inside the smartphone via a fixed line like a USB, or radio such as Bluetooth and WiFi, and the image data of each of the photographed images is sent to the data management server 5, and analysis and analysis on the skin condition is executed by using the image data. In the following, the former case will be mainly described.

On this occasion, the resolution (number of pixels) of the image data is unified to a predetermined resolution for each kind of image (image for texture analysis, image for spots analysis, etc.) to be registered in the data management server 5. To unify the resolution of the images, it is necessary to convert the image having different resolution for each model of the smartphone or for each model of the camera for photographing the skin. The system in FIG. 30 is of a type including an image quality converting unit on the server side, and the system in FIG. 31 is of a type including the image quality converting unit inside the smartphone by adding a function of image quality conversion processing to an application transmitted to each smartphone from the server.

Here, the number of pixels of the digital camera mounted on the smartphone 3 generally known is, for example, 5 M (2560×1920) pixels, 8 M (3264×2448) pixels, 13 M (4128×3096), or the like. Note that the number of pixels of the digital camera in the smartphone 3 tends to increase, and the smartphone 3 with a camera mounted thereto and having the number of pixels larger than 13 m pixels is also released.

In the actual skin photographing, a range of the skin to be photographed by using the conversion lens 1a is defined and, for example, an image corresponding to a predetermined range of the skin is cut out from the photographed image and used for analysis and analysis.

According to the present embodiment, the image is cut out in a square shape and, for example, in the case of the camera having 5 M pixels, the range of 1004×1004 is cut out, in the case of 8 m pixels, the range of 1265×1265 is cut out, and in the case of 13 M pixels, the range of 1600×1600 is cut out.

In the case where the image data of the above-described size is cut out by using the same conversion lens 1a in the camera having a respective number of pixels and used for the analysis and analysis, the image data having different resolution but substantially the same size can be obtained.

However, it is preferable to unify the resolution of the skin images used for analysis and analysis as described above in order to reduce dispersion of the analysis and analysis results and, for example, according to the present embodiment, the pixels of the image data photographed and cut out are thinned to decrease the number of pixels, or the number of pixels is increased by interpolating the pixels of the image data or using the super-resolution, thereby obtaining the predetermined number of pixels of the cut-out image data.

According to the present embodiment, for example, the resolution of the image data is unified to 1024×1024 that is the resolution between the case of 5 M pixels and the case of 8 M pixels.

In this case, in the case where the camera has the resolution of 5 M pixels, it is necessary to increase the number of pixels by interpolating the pixels. As for the image interpolating method, various kinds of image interpolating method such as a nearest-neighbor method, a bilinear method, and a bicubic method are used to increase the resolution of the image data.

Additionally, according to the present embodiment, a relatively simple image interpolating method can be used because the number of pixels (1004×1004) in the above-described image range in the case of 5 M pixels is approximate to the target unified number of pixels (1024×1024) of the image data.

In the case where the resolution (number of pixels) required for diagnosis and analysis using the skin image data is, for example, the lowest resolution such as 5 M pixels, among the resolution (number of pixels) generally used in the camera mounted on the smartphone 3, the number of pixels of the image data in the predetermined range to be cut out as described above from the image photographed by the camera having the lowest resolution may be adopted as the target unified number of pixels of the image data.

For example, the number of pixels 1004×1004 of the image in the predetermined range in the above-described case of 5 M pixels may be adopted as the target unified resolution.

According to the present embodiment, the unified resolution is set to 1024×1024 because a data mount is required be power of two in the fast Fourier transformation that is often used for image processing (power of two is advantageous to calculation).

Note that, here, the number of pixels of the image in the predetermined range in the case of 5 M pixels may be 1024×1024 which is power of two, instead of 1004×1004. In this case, in the case where the conversion lens 1a is set in the camera of 5 M pixels, the range of 1024×1024 is needed to be photographed.

Depending on algorithm used to reduce or increase the number of pixels, but in general, since the smaller the number of pixels of the image data is, the smaller a required storage volume is because processing is slower in the case of increasing the number of pixels than in the case of decreasing the number of pixels of the image when an image quality level is similar and because the image data having the unified number of pixels is stored in the skin history database 5b, and since for example in the case where image processing is necessary for diagnosis and analysis or pre-treatment thereof, the processing can be accelerated when the number of pixels is small, in the case of unifying the number of pixels of the image data photographed by the camera of each smartphone 3, the number of pixels is preferably small as far as the number is the number of pixels necessary for diagnosis and analysis. Therefore, it is preferable as for the resolution of the camera generally used in the smartphone 3 to determine the target unified number of pixels on the basis of the camera of the lowest 5 M pixels.

In the case of the camera of 8 M pixels and the camera of 13 M pixels, the processing of downsizing the image by using the thinning method is executed because the number of pixels is larger than the target unified number of pixels of the image in the above-described predetermined range. In this case, for example, the thinning method such as the nearest neighbor algorithm and the area-average method (pixel-average method, integration) is to be used to decrease the number of pixels.

By executing image upsizing (increasing the number of pixels) and image downsizing (decreasing the number of pixels) as described above, various kinds of diagnosis and analysis on the skin condition become possible by using the image data having the unified number of pixels even when the resolution of the cameras mounted on the smartphone 3 varies.

The image quality conversion processing, in which the image data photographed by setting the conversion lens 1a in the camera of the smartphone 3 is converted to the image data having the unified number of pixels of one kind regardless of the number of pixels of the camera in each smartphone 3 as described above, may be executed on the data management server 5 side or on the smartphone 3 side.

That is, As with the management system for skin condition measurement analysis information illustrated in FIG. 30, an image quality converting unit 5s which executes the image quality conversion processing for decreasing or increasing the number of pixels to unify the number of pixels of the image data photographed by the camera of the above-described smartphone 3 may be provided on the data management server 5 side. That is, the above-described image quality conversion processing is to be performed by an image quality conversion program executed on the data management server 5 side.

In this case, the image data for diagnosis and analysis on the skin condition photographed by the smartphone 3 and the image quality data indicating the number of pixels are sent to the data management server, a square shaped range, for example, is cut out from the image data in the image quality conversion processing by the image quality converting unit 5s, and also the number of pixels in the cut-out portion is converted to 1024 ×1024 as the predetermined number of pixels, and the image data having the converted image quality is stored in the skin history database 5b.

Therefore, in the case where both the above-described image quality data and the image data of the skin before image conversion are stored in the skin history database 5b, the image data of skin stored in the skin history database 5b becomes different. Note that even in the case of registering the image quality data and the image data of the skin before image conversion are in the skin history database 5b, the above-described image conversion processing for unifying the number of pixels of the image data of the skin which may varies depending on the cameras of the smartphone 3 is to be executed at the time of diagnosis and analysis on the image data of the skin, and thus the data management server 5 includes the image quality converting unit 5s as illustrated in FIG. 30.

Additionally, as illustrated in FIG. 31, the above-described image quality conversion processing may be executed on the smartphone 3 side, and an image quality converting unit 3f of executing the above-described image quality conversion processing may be provided on the smartphone 3 side. The function as the image quality converting unit 3f is executable by a program that executes the above-described image quality conversion processing as a part of the above-described dedicated application 5j. The image quality conversion processing is executed on the smartphone 3 side, and the image data that is cut out in the square shape as described above and also converted to have the unified number of images is sent to the data management server 5 and registered in the skin history database 5b, and is also to be used for analysis and diagnosis on the skin condition.

The number of pixels of the skin image data, which is likely to vary depending on the camera of the smartphone 3, is unified, and thus the number of pixels of the image data used in the processing such as diagnosis and analysis becomes the same, and the above-described processing can be smoothly executed and also influence of the difference of the number of pixels of the image data onto the results of the diagnosis and analysis can be prevented. For example, in the case of photographing the same subject with a different number of pixels, the results of the diagnosis and analysis are likely to become different due to the difference in the number of pixels of the image data of the photographed skin; however, by unifying the number of pixels of the image data used for diagnosis and analysis, it is possible to avoid obtaining different analysis result.

Additionally, by unifying or approximating the unified number of pixels of the image data to the lower resolution among the general resolution of the camera of the smartphone 3, it becomes unnecessary to handle any image data having the resolution uselessly higher than the resolution of the image data necessary for the diagnosis and analysis processing, and the storage volume of the skin history database 5b can be reduced, while the load on the data management server 5 by the image processing or the like can be reduced.

In other words, in the case of photographing the skin by using the camera of the smartphone 3 and executing diagnosis and analysis on the skin condition by using the image data of the photographed skin, diagnosis and analysis on the skin image data can be executed without problem even when the resolution of the camera varies depending on the smartphones 3.

Additionally, when the cameras for skin having the same standard are used in the case where the skin condition measuring device 1 as the camera for skin dedicated for photographing the skin is connected through the communication unit such as the USB, the image data sent to the data management server 5 from the camera for skin via the smartphone 3 has the same number of pixels (resolution), and the above-described image quality conversion processing is not necessary.

However, in the case where the cameras for skin have a plurality of standards, that is, in the case where a plurality of kinds of the cameras for skin having the different resolution can be used, the above-described image conversion processing may be executed such that the number of pixels becomes the same among the image data to be input in the same manner as the case where the above-described camera of the smartphone 3 is used. In this case also, the image quality converting unit 5s may be provided in the data management server 5, and the image quality converting unit 3f may be provided in the smartphone 3.

Note that, in the communication via the Internet (network) 4, it is preferable that the data be encrypted. Additionally, as for data input from the client, for example, the server side may have a function as a web server capable of releasing a website on the Internet 4 and the client may have a function as a web browser capable of displaying the website so as to enable data input on the web page of the website. In this case, preferably SSL encryption or TLS encryption can be used as encryption at the time of data input.

REFERENCE SINGS LIST

1 Skin condition measuring device (Skin condition measuring unit)
3 Smartphone (mobile terminal, cosmetic specific information inputting unit, history display unit, non-registered cosmetic specific information inputting unit, temporary registration unit, simultaneous comparison unit)

4 Internet (Network)
5 Data management server (skin condition analyzing unit, history outputting unit, non-registration determining unit, communication assisting unit, user extracting unit, rank extracting unit, rank transmitting unit, registration permitting unit)
5b Skin history database (analysis result storage unit)
5d Using cosmetic history database (using cosmetic specific information storage unit)
5e Detailed analysis result database (analysis result storage unit)
5o Care chart database (using cosmetic specific information storage unit)
5p Registered cosmetic database (registered cosmetic storage unit)
5q Cosmetic maker management database (cosmetic maker contact information storage unit)
6 Contractor client
51 User data database
52 Measurement data database
53 Data analysis database
61 Cosmetic company A server (skin condition analyzing unit), Cosmetic company B server (skin condition analyzing unit)

The invention claimed is:

1. A management system for skin condition measurement analysis information, comprising:
   a user client used by a user of a skin condition measuring device, connected to the skin condition measuring device, so as to be able to transmit data to and receive data from the skin condition measuring device, and also connected to a network to transmit and receive data;
   a data management server configured to transmit data to and receive data from the user client via the network, to store information related to the user, and to provide the information to the user as a primary user of the information and a secondary user of the information who is different from the user;
   an analysis result outputting unit configured to receive analysis result data of a skin condition obtained by analyzing measurement data measured by the skin condition measuring device, and to output the analysis result data to be displayable on the user client; and
   a secondary user client used by the secondary user, configured to transmit data to and receive data from the data management server, and provided with the information related to the user,
   wherein the user client includes:
      a user data transmitting unit configured to transmit user data to the data management server based on a request from the data management server, the user data being input by the user and also including personal information leading to specification of individual of the user and accompanying information excluding personal information of the users, correlated to a unique and non-duplicative client ID for each user;
      a measurement data transmitting unit configured to transmit the input measurement data correlated to the client ID to the data management server when the measurement data of the user measured by the skin condition measuring device is received from the skin condition measuring device; and
      an analysis result display unit configured to display analysis result data when the analysis result data of the measurement data is received from the analysis result outputting unit,
   wherein the data management server includes:
      a user data database in which user data is registered, the user data including the personal information and the accompanying information correlated to the client ID received from each of a plurality of user clients;
      a measurement data database in which the measurement data received from the user client and the client ID are registered to correlate with one another, the measurement data being registered as data in chronological order based on the acquisition time of the measurement data,
      a secondary user database in which a secondary user ID set for each of a plurality of secondary users is registered,
      a data providing unit configured to
         check the secondary user ID input from the secondary user client with the secondary user database when a request is made from the secondary user client to acquire data registered in the user data database or the measurement data database,
         extract the measurement data as data in chronological order of the user specified by the secondary user client and the accompanying information excluding the personal information from the user data, from the user data database and the measurement data database, and
         enable transmission of the extracted measurement data to the secondary user client; and
   wherein the secondary user client includes:
      a data requesting unit configured to transmit the secondary user ID and also request data registered in the user data database or the measurement data database to the data management server; and
      a receiving and storing unit configured to receive and store the accompanying information and the measurement data as the data in chronological order transmitted from the data management server based on a request of the data requesting unit.

2. The management system for skin condition measurement analysis information according to claim 1, wherein
   the skin condition measuring device includes a camera and a conversion lens configured to take a close-up photo of skin;
   the user client, including a transmitting and receiving unit, and the camera are included in a mobile terminal; and
   the camera is connected with the transmitting and receiving unit so as to be able to transmit and receive data in the mobile terminal.

3. The management system for skin condition measurement analysis information according to claim 1,
   wherein access information showing the range of the measurement data and the accompanying information providable to the secondary user are registered to correlate with the secondary user ID in the secondary user database, and
   the data providing unit is configured to transmit, to the secondary user client, the measurement data as data in chronological order of the user, and the accompanying information from the user data, within a range indicatedin the access information correlated with the secondary user ID input from the secondary user client in the secondary user database.

4. The management system for skin condition measurement analysis information according to claims 1, wherein the analysis result data is registered to correlate with the client ID as data in chronological order based on the acquisition time of the analysis result data, in the measurement data database.

5. The management system for skin condition measurement analysis information according to claim 4, wherein the user client further includes:
a measurement data browsing requesting unit configured to request transmission of the measurement data or the analysis result data registered as chronological order information correlated with the client ID of the user in the measurement data database; and
a data displaying unit configured to display transmitted data when the measurement data or the analysis result data requested by the measurement data browsing requesting unit is transmitted from the data management server, and
wherein the data management server further includes:
a data transmitting unit for measurement data browsing, configured to transmit, to the user client, the data registered in the measurement data database and also correlated to the client ID corresponding to the user client, based on the request of the measurement data browsing requesting unit.

6. The management system for skin condition measurement analysis information according to claim 4, wherein the data management server
extracts, in response to a request from the user client, past measurement data or past analysis result data stored in the measurement data database as chronological order information based on the acquisition times, and
transmits the extracted data to the user client, and
the user client includes a comparative display unit configured to display the past measurement data and the measurement data measured by the skin condition measuring device such that both of the measurement data are comparable with each other, or to display the past analysis result data and the analysis result data received from the analysis result outputting unit such that both of the analysis result data are comparable with each other.

7. The management system for skin condition measurement analysis information according to claim 4, wherein
in the user data database, cosmetic data that is input from the user client and also specifies the cosmetic used by the user of the skin condition measuring device is registered to correlate with the use time of the cosmetic and the client ID input from the user client as the accompanying information, and
the data management server is configured to output to the secondary user client
the analysis result data, acquired at the acquisition time corresponding to the use time and correlated with the cosmetic data, together with the cosmetic data.

8. The management system for skin condition measurement analysis information according to claim 4, wherein
in the user data database, cosmetic data that is input from the user client and also specifies the cosmetic used by the user of the skin condition measuring device is registered to correlate with the use time of the cosmetic and the client ID input from the user client as the accompanying information,
the user client is configured to search the measurement data database and the user data database for the analysis result data and the cosmetic data correlated to the client ID that is input from the user client in conformity with the acquisition time of the analysis result data and the use time of the cosmetic, and
the searched analysis result data, correlated to the acquisition time, and the cosmetic data, correlated with the use time that is the same as the acquisition time, are displayable in parallel.

9. The management system for skin condition measurement analysis information according to claim 8, wherein the analysis result data and the cosmetic data, correlated to the use time that is same as the acquisition time, are displayable in parallel in at least two display modes,
at least one of the display modes is a mode of a chronological display in which details of change in the analysis result data are recognizable by being displayed in chronological order, and another display mode is a comparative display mode in which the difference in the analysis result data with respect to the acquisition time are comparable by simultaneously displaying the analysis result data at a plurality of the acquisition times selected by the user.

10. The management system for skin condition measurement analysis information according to claim 1, wherein the data providing unit includes a personal information modifying unit configured to modify personal information leading to specification of an individual when a request is made from the secondary user client to acquire data of the personal information registered in the user data database.

11. The management system for skin condition measurement analysis information according to claim 1, wherein
the skin condition measuring device includes a camera,
the skin condition measuring device is provided with inherent device authentication information for authenticating the skin condition measuring device; and
the user client includes a device authentication information transmitting unit configured to transmit the device authentication information output from the connected skin condition measuring device to the data management server, and
wherein the data management server includes:
an authenticating unit configured to authenticate the device authentication information; and
a non-authenticated device excluding unit configured to execute control so that the measurement data transmitted from the user client having the device authentication information that has not been authenticated by the authenticating unit is not registered in the measurement data database.

12. The management system for skin condition measurement analysis information according to claim 2, wherein
the conversion lens is provided with inherent device authentication information for authenticating the conversion lens,
the user client includes a device authentication information transmitting unit configured to transmit device authentication information output from the connected skin condition measuring device to the data management server, and
wherein the data management server includes:
an authenticating unit configured to authenticate the device authentication information; and
a non-authenticated device excluding unit configured to execute control so that the measurement data transmitted from the user client having the device authentication information that has not been authenticated by the authenticating unit is not registered in the measurement data database.

13. The management system for skin condition measurement analysis information according to claim 1, wherein
the skin condition measuring device is configured to output image data as the measurement data,
the measurement data transmitting unit in the user client transmits the image data output from the skin condition measuring device to the data management server,
wherein the data management server includes:
a calibration data generation unit configured to generate calibration data calibrating an individual difference of the skin condition measuring device based on the image data photographed by the skin condition measuring device in accordance with a predetermined condition; and
a calibration database configured to register the calibration data generated by the calibration data generation unit and the skin condition measuring device to correlate with one another, and
wherein the calibration data is acquired from the calibration database, and the image data is calibrated by the calibration data, and registered in the measurement data database.

14. The management system for skin condition measurement analysis information according to claim 1,
further comprising a skin care device controllable by the user client by being connected to the user client, and
wherein the user client is configured to control the skin care device based on the analysis result data obtained from the analysis result outputting unit.

15. The management system for skin condition measurement analysis information according to claim 14, wherein
the user client or the data management server includes:
a skin care database in which a control method for the skin care device is registered to correlate with the analysis result data;
a skin care data acquiring unit configured to acquire the analysis result data from the measurement data database based on the client ID output from the user client connected to the skin care device; and
a control method acquiring unit configured to acquire the control method for the skin care device from the skin care database based on the analysis result data acquired by the skin care data acquiring unit, and
wherein the user client is configured to control the skin care device based on the control method acquired by the control method acquiring unit.

16. The management system for skin condition measurement analysis information according to claim 1, wherein the analysis result outputting unit includes an analysis unit configured to obtain the analysis result data by analyzing the measurement data and to allow the analysis result data to be input in the analysis result outputting unit.

17. The management system for skin condition measurement analysis information according to claim 1, wherein
the analysis result outputting unit is configured to transmit the measurement data to the server of an analysis supplier that obtains the analysis result data by analyzing the measurement data, and
the analysis result data input by the server of the analysis supplier is storable in the data management server, and transmitted to the user client via the data management server.

18. A management method for skin condition measurement analysis information executed in a managing system for skin condition measurement analysis information that includes i) a user client used by a user of a skin condition measuring device, connected to the skin condition measuring device, so as to be able to transmit data to and receive data from the skin condition measuring device, and also connected to a network so as to transmit and receive data, ii) a data management server configured to transmit data to and receive data from the user client via the network, to store information related to the user, and to provide the information to the user as a primary user of the information and a secondary user of the information who is different from the user, iii) an analysis result outputting unit configured to receive analysis result data of the skin condition obtained by analyzing measurement data measured by the skin condition measuring device, and to output the analysis result data to be displayable on the user client, and iv) a secondary user client used by the secondary user, configured to transmit data to and receive data from the data management server, and provided with the information related to the user, wherein the method comprises the step of the user client executing:
a user data transmitting step of transmitting user data to the data management server based on a request from the data management server, the user data including personal information leading to specification of individual of the user input by the user and accompanying information excluding personal information of the user, correlated to a unique and non-duplicative client ID for each user;
a measurement data transmitting step of transmitting the input measurement data correlated to the client ID to the data management server when measurement data of the user measured by the skin condition measuring device is received from the skin condition measuring device; and
an analysis result displaying step of displaying the analysis result data when the analysis result data of the measurement data is received from the analysis result outputting unit,
wherein the data management server includes:
a user data database in which user data is registered, including the personal information and the accompanying information received from each of a plurality of user clients and correlated with a client ID;
a measurement data database in which the measurement data received from the user client and the client ID are registered to correlate with one another, the e measurement data being registered as data in chronological order based on the acquisition time of the measurement data; and
a secondary user database in which a secondary user ID set for each of a plurality of users is registered,
wherein the method further comprises the step of the data management server executing
checking the secondary user ID input from the secondary user client with the secondary user database when a request is made from the secondary user client to acquire data registered in the user data database or the measurement data database,
extracting the measurement data as data in chronological order of the user specified by the secondary user client and the accompanying information excluding the personal information from the user data, from the user data database and the measurement data base, and
transmitting the extracted measurement data to the secondary user client, and
wherein the method further comprises the step of the secondary user client executing:
a data requesting step of transmitting the secondary user ID and also requesting data registered in the user data database or the measurement data database to the data management server; and a receiving and storing step of receiving and storing the accompanying information and the measurement data as the data in chronological order transmitted from the data management server based on a request of the data requesting step.

19. The management method for skin condition measurement analysis information according to claim 18, wherein in the management system for skin condition measurement analysis information, the skin condition measuring device includes a camera and a conversion lens configured to take a close-up photo of skin;

the user client, including a transmitting and receiving unit, and the camera are included in a mobile terminal; and the camera is connected with the transmitting and receiving unit so as to be able to transmit and receive data in the mobile terminal.

20. The management method for skin condition measurement analysis information according to claim 18, wherein in the secondary user database, access information indicating the range of the measurement data and the accompanying information providable to the secondary user are registered to correlate with the secondary user ID; and in the data providing step, the measurement data as data in the chronological order of the user and the accompanying information from the user data are transmitted to the secondary user client within a range indicated by the access information correlated with the secondary user ID input from the secondary user client in the secondary user database.

21. The management method for skin condition measurement analysis information according to claim 18, wherein in the measurement data database, the analysis result data is registered to correlate with the client ID as data in chronological order based on the acquisition time of the analysis result data.

22. The management method for skin condition measurement analysis information according to claim 21, wherein the user client further executes:

a measurement data browsing requesting step of requesting transmission of the measurement data or the analysis result data registered as chronological order information correlated with the client ID of the user to the measurement data database; and a data displaying step of displaying transmitted data when the measurement data or the analysis result data requested by the measurement data browsing requesting step is transmitted from the data management server, wherein the data management server further executes:

a data transmitting step for measurement data browsing of transmitting, to the user client, data registered in the measurement data database and also correlated with the client ID corresponding to the user client, based on the request of the measurement data browsing requesting step.

23. The management method for skin condition measurement analysis information according to claim 21, wherein the data management server extracts, in response to a request from the user client, the past measurement data or the past analysis result data stored in the measurement data database as chronological order information based on the acquisition times and transmits the extracted data to the user client; and the user client executes a comparative displaying step of displaying the past measurement data and the measurement data measured by the skin condition measuring device such that both measurement data are comparable with each other, or displaying the past analysis result data and the analysis result data received from the analysis result outputting unit such that both analysis result data are comparable with each other.

24. The management method for skin condition measurement analysis information according to claim 21, wherein in the user data database, cosmetic data that is input from the user client and also specifies the cosmetic used by the user of the skin condition measuring device is registered to correlate with the use time of the cosmetic and the client ID input from the user client as the accompanying information, the data management server outputs, to the secondary user client, the analysis result data of the acquisition time corresponding to the use time correlated to the cosmetic data together with the cosmetic data.

25. The management method for skin condition measurement analysis information according to claim 21, wherein in the user data database, cosmetic data that is input from the user client and also specifies the cosmetic used by the user of the skin condition measuring device is registered to correlate with the use time of the cosmetic and the client ID input from the user client as the accompanying information;

the user client searches the measurement data database and the user data database for the analysis result data and the cosmetic data correlated to the client ID input from the user client in conformity with the acquisition time of the analysis result data and the use time of the cosmetic; and the analysis result data, correlated to the searched acquisition time, and the cosmetic data, correlated with the use time that is the same as the acquisition time, are displayed in parallel.

26. The management method for skin condition measurement analysis information according to claim 25, further comprising the step of displaying the analysis result data and the cosmetic data, correlated to the use time that is the same as the acquisition time, in parallel in at least two display modes, at least one of the display modes is a mode of a chronological display in which details of change in the analysis result data are recognizable by being displayed in chronological order, and another display mode is a comparative display mode in which the differences in of the analysis result data with respect to the acquisition time are comparable by simultaneously displaying the analysis result data at a plurality of the acquisition times selected by the user.

27. The management method for skin condition measurement analysis information according to claim 18, wherein in the data providing step, a personal information modifying step is executed, the personal information modifying step modifying personal information leading to specification of an individual when a request is made from the secondary user client to acquire data of the personal information registered in the user data database.

28. The management method for skin condition measurement analysis information according to claim 18, wherein the skin condition measuring device includes a camera, the skin condition measuring device is provided with inherent device authentication information for authenticating the skin condition measuring device;

the user client executes a device authentication information transmitting step of transmitting device authentication information output from the connected skin condition measuring device to the data management server; and the data management server executes an authenticating step of authenticating the device authentication information; and a non-authenticated device excluding step of executing control so that the measurement data transmitted from the user client having the device authentication information that has not been authenticated by the authentication step is not registered in the measurement data database.

29. The management method for skin condition measurement analysis information according to claim 19, wherein the conversion lens is provided with inherent device authentication information for authenticating the conversion lens, the user client executes a device authentication information transmitting step of transmitting the device authentication information output from the connected skin condition measuring device to the data management server;

the data management server executes an authenticating step of authenticating the device authentication information, and a non-authenticated device excluding step of executing control so that the measurement data transmitted from the user client having the device authentication information that has not been authenticated by the authenticating step is not registered in the measurement data database.

30. The management method for skin condition measurement analysis information according to claim 18, wherein the skin condition measuring device is configured to output image data as the measurement data, in the measurement data transmitting step of the user client, the image data output from the skin condition measuring device is transmitted to the data management server, and wherein in the data management server, a calibration data generation step of generating calibration data calibrating an individual difference of the skin condition measuring device based on the image data photographed by the skin condition measuring device in accordance with a predetermined condition is executed;

a calibration database configured to register the calibration data generated in the calibration data generation step and correlated to the skin condition measuring device; and the calibration data is acquired from the calibration database, and the image data is calibrated by the calibration data, and registered in the measurement data database.

31. The management method for skin condition measurement analysis information according to claim 18, wherein the management system further includes a skin care device controllable by the user client by being connected to the user client, and the user client is configured to control the skin care device based on the analysis result data obtained from the analysis result outputting unit.

32. The management method for skin condition measurement analysis information according to claim 31, wherein the user client or the data management server includes a skin care database in which a control method for the skin care device is registered to correlate with the analysis result data, a skin care data acquiring step of acquiring the analysis result data from the measurement data database based on the client ID output from the user client connected to the skin care device; and a control method acquiring step of acquiring the control method for the skin care device from the skin care database based on the analysis result data acquired by the skin care data acquiring step are executed, and the user client being configured to control the skin care device based on the control method acquired by the control method acquiring step.

33. The management method for skin condition measurement analysis information according to claim 18, wherein the analysis result outputting unit is configured to execute an analyzing step of obtaining the analysis result data by analyzing the measurement data and to allow the analysis result data to be input to the analysis result outputting unit.

34. The management method for skin condition measurement analysis information according to claim 18, wherein the analysis result outputting unit is configured to transmit the measurement data to the server of an analysis supplier that obtains the analysis result data by analyzing the measurement data, and also render the analysis result data input by the server of the analysis supplier to be storable in the data management server, and transmit the analysis result data to the user client via the data management server.

35. A data management server comprising:

a user data receiving unit configured to receive user data including personal information leading to specification of individual of a user of a skin condition measuring device and accompanying information excluding personal information of the user, and correlated to a unique and non-duplicative client ID for each user;

a measurement data receiving unit configured to receive measurement data measured using the skin condition measuring device by the user and correlated to the client ID of the user;

an analysis result outputting unit configured to output analysis result data of the skin condition obtained by analyzing measurement data to be displayable on the terminal of the user;

user data database in which user data including the personal information and the accompanying information received from the user data receiving unit and correlated to the client ID is registered;

measurement data database in which the measurement data and the client ID are registered to correlate with one another, and also, in which the measurement data is registered as data in chronological order based on an acquisition time of the measurement data, a secondary user database in which a secondary user ID set for each of a plurality of secondary users is registered, each of the plurality of secondary users desiring to use the data in the user data database and the measurement data database and being different from the user as a primary user of the data in the user data database and the measurement data database;

a secondary user data requesting receiving unit configured to receive a request made from the terminal of the secondary user to acquire the secondary user ID and the data registered in the user data database or the measurement data database;

a secondary user data providing unit configured to check the secondary user ID received by the secondary user data requesting receiving unit with the secondary user database, extract, from the user data database and the measurement data database, the measurement data as data in chronological order of the user specified by the request of the secondary user received by the secondary user data requesting receiving unit, and the accompanying information excluding the personal information from the user data, and transmit the extracted data to the terminal of the secondary user.

36. The data management server according to claim 35, wherein in the measurement data database, the analysis result data received from the analysis result outputting unit and the client ID are registered to correlate with one another as data in chronological order based on the acquisition time of the measurement data.

37. A data management server according to claim 36, wherein the data management server includes:

a measurement data browsing requesting receiving unit configured to receive, from the terminal of the user, a transmission request of the measurement data or the analysis result data registered as chronological order information correlated to the client ID of the user in the measurement data database; and a data transmitting unit for measurement data browsing configured to transmit, to the terminal of the user, data registered to the measurement data database and also correlated to the client ID corresponded to the terminal of the user, based on the transmission request of the user received by the measurement data browsing requesting receiving unit.

38. A data management server according to claim 37, wherein the data transmitting unit for measurement data browsing is configured to extract, based on a transmission request received by the measurement data browsing requesting receiving unit, a plurality of the measurement data or the analysis result data of different acquisition times or at least one of past measurement data or the past analysis result data from the measurement data database and to transmit the extracted data to the terminal of the user.

39. A data management server according to claim 36, wherein in the user data database, cosmetic data that is input from the terminal of the user and also specifying the cosmetic used by the user of the skin condition measuring device is registered to correlate with the use time of the cosmetic and the client ID as the accompanying information; and the secondary user data providing unit is configured to transmit the analysis result data of the acquisition time corresponding to the use time correlated to the cosmetic data together with the cosmetic data to the terminal of the secondary user.

40. A data management server according to claim 36, wherein in the user data database, cosmetic data that is input from the terminal of the user and specifies the cosmetic used by the user of the skin condition measuring device is registered to correlate with the use time of the cosmetic and the client ID input from the terminal of the user as the accompanying information; and the analysis result data and the cosmetic data correlated to the client ID received from the terminal of the user are searched in the measurement data database and the user data database, in conformity with the acquisition time of the analysis result data and the use time of the cosmetic, in response to the request from the terminal of the user, and the searched analysis result data, correlated to the acquisition time, and the cosmetic data, correlated to the use time that is same as the acquisition time, are transmitted to the terminal of the user.

41. A data management server according to claim 36, wherein the secondary user data providing unit is configured to extract, from the user data database and the measurement data database, the measurement data and the analysis result data as data in chronological order of the user specified by the request of the secondary user received by the secondary user data requesting receiving unit and the accompanying information excluding the personal information from the user data, and to transmit the extracted data to the terminal of the secondary user.

42. A data management server according to claim 35, wherein in the secondary user database, access information indicating the range of the measurement data and the accompanying information that can be provided to the secondary user are registered to correlate with to the secondary user ID, and the secondary user data providing unit is configured to transmit, to the terminal of the secondary user, the measurement data as chronological order information of the user and the accompanying information from among the user data within a range indicated in the access information correlated to the secondary user ID received from the secondary user data requesting receiving unit in the secondary user database.

43. A data management server according to claim 35, wherein the secondary user data providing unit includes a personal information modifying unit configured to modify the personal information leading to specification of an individual when a request is made from the terminal of the secondary user to acquire data of the personal information registered in the user data database.

44. A data management server, comprising:

a user data receiving unit configured to receive user data including personal information leading to specification of individual of a user of a skin condition measuring device and accompanying information excluding personal information of the user, and correlated to a unique and non-duplicative client ID for each user;

a measurement data receiving unit configured to receive measurement data measured using the skin condition measuring device by the user and correlated to the client ID of the user, an analysis result outputting unit configured to output the analysis result data of the skin condition obtained by analyzing the measurement data displayable on the terminal of the user;

a user data database configured to register user data including the personal information and the accompanying information received by the user data receiving unit and correlated to the client ID;

a measurement data database in which analysis result data of the skin condition obtained by analyzing the measurement data and the client ID are registered to correlate with one another, and the analysis result data is registered as data in chronological order based on an acquisition time of the measurement data;

a secondary user database in which a secondary user ID set for each of secondary users is registered, each secondary user desiring to use the data in the user data database and the measurement data database and being different from the user as a primary user of the data in the user data database and the measurement data database;

a secondary user data requesting receiving unit configured to receive a request made from the terminal of the secondary user to acquire the secondary user ID and the data registered in the user data database or the measurement data database; and a secondary user data providing unit configured to
check the secondary user ID received by the secondary user data requesting receiving unit with the secondary user database,
extract, from the user data database and the measurement data database, analysis result data as data in chronological order of the user specified by the request of the secondary user received by the secondary user data requesting receiving unit, and the accompanying information excluding the personal information from the user data, and
enable transmission of the extracted data to the terminal of the secondary user.

45. A data management server according to claim 44, wherein
in the measurement data database, the measurement data received by the measurement data receiving unit and the client ID are registered to correlate with one another, as data in chronological order based on an acquisition time of the measurement data.

* * * * *